US 7,713,544 B2

(12) United States Patent
Chaikof et al.

(10) Patent No.: US 7,713,544 B2
(45) Date of Patent: *May 11, 2010

(54) BIOLOGICAL COMPONENT COMPRISING ARTIFICIAL MEMBRANE

(75) Inventors: Elliot L. Chaikof, Atlanta, GA (US); June Feng, Duluth, GA (US); Janine M. Orban, Warsaw, IN (US); Hongbo Liu, Hillsborough, NJ (US); Xue Long Sun, Atlanta, GA (US); Keith M. Faucher, Athens, GA (US)

(73) Assignee: Emory University, Atlanta, GA (US)

( * ) Notice: Subject to any disclaimer, the term of this patent is extended or adjusted under 35 U.S.C. 154(b) by 1278 days.

This patent is subject to a terminal disclaimer.

(21) Appl. No.: 10/343,408

(22) PCT Filed: Jul. 30, 2001

(86) PCT No.: PCT/US01/24020
§ 371 (c)(1),
(2), (4) Date: Jul. 22, 2003

(87) PCT Pub. No.: WO02/09647
PCT Pub. Date: Feb. 7, 2002

(65) Prior Publication Data
US 2004/0063200 A1    Apr. 1, 2004

Related U.S. Application Data

(60) Provisional application No. 60/221,828, filed on Jul. 28, 2000, provisional application No. 60/221,618, filed on Jul. 28, 2000, provisional application No. 60/221,655, filed on Jul. 28, 2000.

(51) Int. Cl.
*A61L 27/00* (2006.01)
*A61F 13/00* (2006.01)
*A61K 9/127* (2006.01)

(52) U.S. Cl. ............ 424/450; 623/1.49; 623/2.42; 623/11.11; 427/2.28; 427/2.3; 427/2.31; 424/422; 424/423

(58) Field of Classification Search .......... 424/450, 424/422, 423; 427/2.24, 2.25, 2.3; 623/1.49, 623/2.42, 11.11
See application file for complete search history.

(56) References Cited

U.S. PATENT DOCUMENTS
4,485,045 A   11/1984   Regen ............ 260/403
(Continued)

FOREIGN PATENT DOCUMENTS
WO    WO 96/21469    7/1996
(Continued)

OTHER PUBLICATIONS
C. J. Weber et al., "Long-term survival of poly-L-lysine-alginate microencapsulated rat, rabbit, and pig islet xenografts in spontaneously diabetic NOD mice," Chapter 11, pp. 117-137, In: Kuhtreiber W.M., Lanza R, Chick, W., ed., *Cell Encapsulation Technology and Therapeutics*, Jun. 1999; New York: Springer-Verlag.
(Continued)

*Primary Examiner*—Gollamudi S Kishore
(74) *Attorney, Agent, or Firm*—Greenlee, Winner and Sullivan, P.C.

(57) ABSTRACT

A biocompatible biological component is provided comprising a membrane-mimetic surface film covering a substrate. Suitable substrates include hydrated substrates, e.g. hydrogels which may contain drugs for delivery to a patient through the membrane-mimetic film, or may be made up of cells, such as islet cells, for transplantation. The surface may present exposed bioactive molecules or moieties for binding to target molecules in vivo, for modulating host response when implanted into a patient (e.g. the surface may be antithrombogenic or antiinflammatory) and the surface may have pores of selected sizes to facilitate transport of substances therethrough. An optional hydrophilic cushion or spacer between the substrate and the membrane-mimetic surface allows transmembrane proteins to extend from the surface through the hydrophilic cushion, mimicking the structure of naturally-occurring cells. An alkylated layer directly beneath the membrane-mimetic surface facilates bonding of the surface to the remainder of the biological component. Alkyl chains may extend entirely through the hydrophilic cushion when present. To facilitate binding, the substrate may optionally be treated with a polyelectrolyte or alternating layers of oppositely-charged polyelectrolytes to facilitate charged binding of the membrane-mimetic film or alkylated layer beneath the membrane-mimetic film to the substrate. The membrane-mimetic film is preferably made by in situ polymerization of phospholipid vesicles.

59 Claims, 19 Drawing Sheets

U.S. PATENT DOCUMENTS

| | | | | |
|---|---|---|---|---|
| 4,522,803 | A | 6/1985 | Lenk et al. | 424/1.1 |
| 4,560,599 | A | 12/1985 | Regen | 428/36 |
| 4,880,883 | A | 11/1989 | Grasel et al. | 535/454 |
| 4,885,172 | A * | 12/1989 | Bally et al. | 424/417 |
| 4,906,465 | A | 3/1990 | Chaikof et al. | 424/78 |
| 5,071,532 | A | 12/1991 | Taillet et al. | 204/229 |
| 5,288,517 | A | 2/1994 | Kanno et al. | 427/244 |
| 5,399,331 | A | 3/1995 | Loughrey et al. | 424/450 |
| 5,417,969 | A | 5/1995 | Hsu et al. | 424/78 |
| 5,429,618 | A | 7/1995 | Keogh | 604/266 |
| 5,695,964 | A * | 12/1997 | Nii et al. | 435/69.6 |
| 5,741,325 | A | 4/1998 | Chaikof et al. | 623/1 |
| 5,755,788 | A | 5/1998 | Strauss | 623/1 |
| 5,911,942 | A | 6/1999 | Fofonoff et al. | 264/444 |
| 6,071,532 | A | 6/2000 | Chaikof et al. | 424/450 |
| 6,171,614 | B1 | 1/2001 | Chaikof et al. | 424/450 |
| 6,461,385 | B1 * | 10/2002 | Gayer et al. | 623/23.51 |
| 6,537,977 | B1 * | 3/2003 | Kyogashima et al. | 514/54 |
| 6,583,251 | B1 | 6/2003 | Chaikof et al. | 526/277 |
| 6,699,952 | B2 * | 3/2004 | Chaikof et al. | 526/277 |
| 6,936,298 | B2 * | 8/2005 | Chaikof et al. | 427/2.24 |
| 2001/0016772 | A1 * | 8/2001 | Lee et al. | 623/14.12 |

FOREIGN PATENT DOCUMENTS

| | | |
|---|---|---|
| WO | WO 98/16198 | 4/1998 |
| WO | WO 00/00239 | 1/2000 |
| WO | WO 01/78800 | 4/2001 |
| WO | WO 01/80921 | 4/2001 |
| WO | WO 02/09647 | 7/2001 |
| WO | WO 02/055021 | 1/2002 |

OTHER PUBLICATIONS

U.S. Appl. No. 10/257,805, filed Apr. 13, 2002, Chaikof et al.
U.S. Appl. No. 10/258,207, filed Oct. 18, 2002, Chaikof et al.
U.S. Appl. No. 10/343,408, filed Jul. 22, 2003, Chaikof et al.
U.S. Appl. No. 10/451,011, filed Jun. 19, 2003, Chaikof et al.
U.S. Appl. No. 10/452,997, filed Jun. 2, 2003, Chaikof et al.
U.S. Appl. No. 10/720,025, filed Nov. 21, 2003, Chaikof et al.
Akagawa, M. and Suyama, K., "Mechanism of formation of elastin crosslinks," (2000) Connect. Tissue Res. 41(2):131-141.
Akita, K. et al., Effect of FK506 and anti-CD4 therapy on fetal pig pancreas xenografts and host lymphoid cells in NOD/Lt, CBA, and BALB/c mice, (1994) Cell Transplantation 3(1):61-73.
Anderson et al., "Bioactive silk-like protein polymer films on silicon devices," Alper, M., Bayby, H., Kaplan, D. and Navia, M., ed.; Materials Research Society Symp Proc.: Pittsburgh, PA; 1994, 330:171-177.
Andree, H.A.M. et al., "Transport rate limited catalysis on macroscopic surfaces: the activation of factor X in a continuous flow enzyme reactor," (1994) Biochemistry 33(14):4368-4374.
Aoi, K. et al., "Glycopeptide synthesis by an α-amino acid N-carboxyanhydride (NCA) method: ring-opening polymerization of a sugar-substituted NCA," (1994) Macromolecules 27:875-877.
Aoi, K. et al., "Architectural control of sugar-containing polymers by living polymerization: ring-opening polymerization of 2-oxazolines initiated with carbohydrate derivatives," (1992) Macromolecules 25:7073-7075.
Arnander, C. and Olsson, P., "Influence of blood flow and the effect of protamine on the thromboresistant properties of a covalently bonded heparin surface," (1988) J. Biomed. Mater. Res. 22(10):859-868.
Balachander, N. and Sukenik, C.N., "Monolayer transformation by nucleophilic substitution: applications to the creation of new monolayer assemblies," (1990) Langmuir 6(11):1621-1627.
Basmadjian, D. et al., "Coagulation on biomaterials in flowing blood: some theoretical considerations," (1997) Biomaterials 17(23):1511-1522.
Basmadjian, D. and Sefton, M.V., "Relationship between release rate and surface concentration for heparinized materials," (1983) Journal of Biomedical Materials Research 17(3):509-518.

Beyer, D. et al., "Covalently attached polymer mono- and multilayers on silanized glass substrates," (1996) Thin Solid Films 285:825-828.
Bierbaum, K. et al., "A near edge X-ray absorption fine structure spectroscopy and X-ray photoelectron spectroscopy study of the film properties of self-assembled monolayers of organosilanes on oxidized Si(100)," (1995) Langmuir 11:512-518.
Biessen, E.A.L. et al., "Synthesis of cluster galactosides with high affinity for the hepatic asialoglycoprotein receptor," (1995) J. Med. Chem. 38:1538-1546.
Billy, D. et al., "Prothrombin activation by prothrombinase in a tubular flow reactor," (1995) J. Biol. Chem. 270(3):1029-1034.
Biro, S. et al., "Expression and subcellular distribution of basic fibroblast growth factor are regulated during migration of endothelial cells," (1994) Circ. Res. 74:485-494.
Bitomsky, W. and Wade, R.C., "Docking of glycosaminoglycans to heparin-binding proteins: validation for aFGF, bFGF, and antithrombin and application to IL-8," (1999) J. Am. Chem. Soc. 121:3004-3103.
Björquist, P. et al., "Determination of the inetic constants of tissue factor/factor VII/factor VIIA and antithrombin/heparin using surface plasmon resonance," (1997) Thromb. Res. 85(3):225-236.
Blezer, R. et al., "Initiation and propagation of blood coagulation at artificial surfaces studied in a capillary flow reactor," (1998) Thromb. Haemostasis 79(2):296-301.
Blezer, R. et al., "Activation of blood coagulation at heparin-coated surfaces," (1997) J. Biomedical Materials Research 37(1):108-113.
Bon, S.A.F. and Haddleton, D.M., "Amphiphilic copolymers by atom transfer polymerization with carbohydrate-based initiators and monomers," (1999) Polym. Prepr. (Am. Chem. Soc., Div. Polym. Chem.) 40(2):248-249.
Bourin, M.C. and Lindahl, U., "Glycosaminoglycans and the regulation of blood coagulation," (1993) Biochemical J. 289(Pt2):313-330.
Brittain, H.A. et al., "Sickle erythrocyte adherence to large vessel and microvascular endothelium under physiologic flow is qualitatively different," (1992) J. Lab. Clin. Med. 112:538-545.
Broch, H. et al., "Quantum molecular modeling of the elastinic tetrapeptide Val-Pro-Gly-Gly," (1998) J. Biomol. Struct. & Dyn. 15: 1073-1091.
Brown, D.F.M., "Treatment options for deep venous thrombosis," (Nov. 2001) Emergency Medicine Clinics of North America 19(4):913-923.
Brummel, .E. et al., "An integrated study of fibrinogen during blood coagulation," (1999) J. Biol. Chem. 274(32):22862-22870.
Buller, C.E. et al., "Primary stenting versus balloon angioplasty in occluded coronary arteries," (1999) Circulation 100(3):236-242.
Byun, Y. et al., "Binding of antithrombin III and thrombin to immobilized heparin under flow conditions," (1996) Biotechnology Progress 12(2):217-225.
Byun, Y. et al., "Mechanism of thrombin inactivation by immobilized heparin," (1996) J. Biomed. Mater. Res. 30:423-427.
Cai, W.Z. et al., "A solid-state n.m.r. study of microphase structure and segmental dynamics of poly(styrene-b-methylphenylsiloxane) diblock copolymers," (1993) Polymer 34:267-276.
Campbell, E.J. et al., "Biocompatible surfaces using methacryloylphosphorylcholine laurylmethacrylate copolymer," (1994) ASAIO J. 40(3):M853-M857.
Calistri-Yeh, M. et al., "Thermal stability of self-assembled monolayers from alkylchlorosilanes," (1996) Langmuir 12:2747.
Cao, Q. et al., "Sequence of abductin, the molluscan 'rubber' protein," (1997) Curr. Biol. 7:R677-678.
Chaikof, E.L., "Biomaterials that imitate cell microenvironments," (1996) Chemtech. 26:17-24.
Chaikof, E.L. et al., "PEO enhancement of platelet deposition, fibrinogen deposition, and complement C3 activation," (1992) J. Biomed. Mater. Res. 26:1163-1168.
Chang, D.K. et al., "Nuclear overhauser effect and computational characterization of the β-spiral of the polypentapeptide of elastin," (1989) J. Biomol. Struct. Dyn. 6(5):851-858.
Chang, D.K. and Urry, D.W., "Molecular dynamics calculations on relaxed and extended states of the polypentapeptide of elastin," (1988) Chem. Phys. Lett. 147:395-400.

Chapman, D., "Biomembranes and new hemocompatible materials," (1993) *Langmuir* 9:39-45.

Chen, C. et al., "Phosphorylcholine coating of ePTFE grafts reduces neointimal hyperplasia in canine model," (1997) *Ann. Vasc. Surg.* 11(1):74-79.

Chen, T-M et al., "Studies on the synthesis and properties of novel phospholipid analogous polymers," (1996) *J. Appl. Polym. Sci.* 60:455-464.

Cheung, J. H. et al., "Molecular self-assembly of conducting polymers," (1994) *Thin Solid Films* 244:985-989.

Chon, J.H. et al., "Cytomimetic biomaterials. 3. Preparation and transport studies of an alginate/amphiphilic copolymer/polymerized phospholipid film," (1999) *J. Biomater. Sci. Polymer. Ed.* 10:95-107.

Chon, J.H. et al., "α4β1 and α5β1 control cell migration on fibronectin by differentially regulating cell speed and motile cell phenotype," (1998) *Ann. Biomed. Eng.* 26:1091-1101.

Chon, J.H. et al., "Role of fibronectin and sulfated proteoglycans in endothelial cell migration on a cultured smooth muscle layer," (1997) *J. Surg. Res.* 72:53-59.

Christianson, S. et al., "Adoptive transfer of diabetes into immunodeficient NOD-*scid/scid* mice: relative contributions of CD4+ and CD8+ T-cells from diabetic versus prediabetic NOD. NON-*Thy-1$^a$* donors," (1993) *Diabetes* 42:44-55.

Cima, L.G. and Lopina, S.T., "Network structures of radiation-cross-linked star polymer gels," (1995) *Macromolecules* 28:6787-6794.

Clowes, AW et al., "Mechanisms of arterial graft failure. II. Chronic endothelial and smooth muscle cell proliferation in healing polytetrafluoroethylene prostheses," (1986) *J. Vasc. Surg.* 3:877-884.

Clowes, A.W. et al., "Mechanism of arterial graft failure. 1. Role of cellular proliferation in early healing of PTFE prostheses," (1985) *Am. J. Pathol.* 118 1 :44-54.

Clowes, A.W. and Karnovsky, M.J., "Suppression by heparin of smooth muscle cell proliferation in injured arteries," (1977) *Nature* 625-626.

Colton, C.K., "The engineering of xenogeneic islet transplantation by immunoisolation," (1992) *Diab. Nutr. Metabol.* 5:145-149.

Colton, C. and Avgoustiniatos, E. "Bioengineering in the development of the hybrid artificial pancreas I" (1991) *Biochem. Eng.* 113:152-70.

Contino, P.B. et al., "Use of an oriented transmembrane protein to probe the assembly of a supported phospholipid bilayer," (1994) *Biophys. J.* 67:1113-1116.

Crooks, C.A., et al., "Microencapsulation of mammalian cells in a HEMA-MMA copolymer: effects on capsule morphology and permeability,"(1990) *J. Biomed. Mater. Res.* 24: 1241-1262.

Cruise, G.M. et al., "A sensitivity study of the key parameters in the interfacial photopolymerization of poly(ethylene glycol) diacrylate upon porcine islets," (1998) *Biotechnol. Bioeng.* 57: 655-65.

Daugherty, D. L. and Gellman, S. H., "A fluorescence assay for leucine zipper dimerization: avoiding unintended consequences of fluorophore attachment," (1999) *J. Am. Chem. Soc.* 121:4325-4333.

Dautzenberg, H. et al., Polyelectrolyte complex formation at the interface of solutions, (1996), *Polym. Sci.* 101:149-156.

Debelle, L. and Tamburro, A.M., "Elastin: molecular description and function," (1999) *Internat. J. Biochem. & Cell Biol.* 31:261-272.

Decher, G., "Fuzzy nanoassemblies: toward layered polymeric multicomposites," (1997) *Science* 277:1232-1237.

Defrees, S.A. et al., "Sialyl lewis x liposomes as a multivalent ligand and inhibitor of E-selectin mediated cellular adhesion," (1996) *J. Am. Chem. Soc.* 118:6101-6104.

Deming, T. J., "Mussel byssus and biomolecular materials," (1999) *Curr. Opin. Chem. Biol.* 3: 100-5.

Dixon, W. T., "Spinning-sideband-free and spinning-sideband-only NMR spectra in spinning samples," (1982) *J. Chem. Phys.* 77:1800-1809.

Dixon, W.T., "Total suppression of sidebands in CPMAS C-13 NMR," (1982) *J. Magn. Reson.* 49:341-345.

Dluhy, R.A., "Quantitative external reflection infrared spectroscopic analysis of insoluble monolayers spread at the air-water interface," (1986) *J. Phys. Chem.* 90:1373-1379.

Dodson, G.G. et al., "molecular recognition in insulin assembly," (1993) *Biochem. Soc. Trans.* 21:609-614.

Doshi, J. and Reneker, D.H., "Electrospinning process and applications of electrospun fibers," (1995) *J. Electrostatics* 35: 151-160.

Eaton, D. F., "Dye sensitized photo polymerization," (1986) *Advances in Photochemistry* 13:427-487.

Egger, N. et al., "Solid state NM investigation of cationic polymerized epoxy resins," (1992) *J. Appl. Poly. Sci.* 44:289-295.

Einaga, Y. et al., "Photofunctional vesicles containing Prussian blue and azobenzene," (1999) *J. Am. Chem. Soc.* 121:3745-3750.

Eitzman, D.T. et al., "Heparin neutralization by platelet-rich thrombi," (1994) *Circulation* 89(4):1523-1529.

Ejaz, M. et al. (2000) *Macromolecules* 33:2870.

Elbert, D. L. et al., "Thin polymer layers formed by polyelectrolyte multilayer techniques on biological surfaces," (1999) *Langmuir* 15:5355-5362.

Elender, G. et al., "Functionalisation of Si/SiO$_2$ and glass surfaces with ultrathin dextran films and deposition of lipid bilayers," (1996) *E. Biosensors Bioelectronics* 11:565-577.

Elliott, J. T. and Prestwich, G. D., "Maleimide-functionalized lipids that anchor polypeptides to lipid bilayers and membranes," (2000) *Bioconjugate Chem.* 11:832-841.

Esmon, C.T. et al., "Regulation and functions of the protein C anticoagulant pathway," (1999) *Haematologica* 84(4):363-368.

Esmon, C.T. et al., "The protein C pathway: new insights," (1997) *Thromb. Haemostasis* 78(1):70-74.

Esmon, C.T., "Thrombomodulin as a model of molecular mechanisms that modulate protease specificity and function at the vessel surface," (1995) *FASEB Journal* 9(10):946-955.

Esmon, C.T. and Owen, W.G., "Identification of an endothelial cell cofactor for thrombin-catalyzed activation of protein C," (1981) *Proc. Natl. Acad. Sci. USA* 78(4):2249-2252.

Esmon, N.L. et al., "Proteolytic formation and properties of γ-carboxyglutamic acid-domainless protein C," (1983) *J. Biol. Chem.* 258:(9):5548-5553.

Esmon, N.L. et al., "Thrombomodulin blocks the ability of thrombin to activate platelets," (1983) *J. Biol. Chem.* 258(20):12238-12242.

Esmon, N.L. et al., "Isolation of a membrane-bound cofactor for thrombin-catalyzed activation of protein C," (1982) *J. Biol. Chem.* 257(2):859-864.

España, F. et al., "In vivo and in vitro complexes of activated protein C with two inhibitors in baboons," (1991) *Blood* 77(8):1754-1760.

Faham, S. et al. "Heparin structure and interactions with basic fibroblast growth factor," (1996) *Science* 271:1116-1120.

Feingold, H.M. et al., "Coagulation assays and platelet aggregation patterns in human, baboon, and canine blood," (1986) *Am. J. Vet. Res.* 47:2197-2199.

Feng, J. and Chaikof, E.L., "Reconstitution of thrombomodulin into polymerizable phospholipid vesicles," (2000) *Polymer Preprints* 41(2):1653-1654.

Flitsch, S.L., "Chemical and enzymatic synthesis of glycopolymers," (Dec. 2000) *Current Opinion in Chem. Biol.* 4(6):619-625.

Florin, E.L. and Gaub, H.E., "Painted supported lipid membranes," (1993) *Biophys J.* 64:375-383.

Fong, H. et al., "Beaded nanofibers formed during electrospinning," (1999) *Polymer* 40: 4585-4592.

Foster, J.A. et al., "Isolation and amino acid sequences of tropoelastin peptides," (1973) *J. Biol. Chem.* 24:2876-2879.

Frank, M. and Ries, L.F., "The role of complement in inflammation and phagocytosis," (1991) *Immunol. Today* 12:322-326.

Franzblau, C. et al., "Role of crosslinking in fiber formation," (1977) *Adv. Exp. Med. Biol.* 79:313-327.

Galvin, J.B. et al., "Reconstitution of rabbit thrombomodulin into phospholipid vesicles," (1987) *J. Biol. Chem.* 262(5):2199-2205.

Gemmell, C.H. et al., "The effects of shear rate on the enzymatic activity of the tissue factor-factor VIIa complex," (1990) *Microvasc. Res.* 40(30):327-340.

Gemmell, C.H. et al., "Utilization of a continuous flow reactor to study the lipoprotein-associated coagulation inhibitor (LACI) that inhibits tissue factor," (1990) *Blood* 76(11):2266-2271.

Gentry, R. et al., "Surface-mediated enzymatic reactions: simulations of tissue factor activation of factor X on a lipid surface," (1995) *Biophys. J.* 69(2):362-371.

Gerling, I. et al., "Multiple low-dose streptozocin-induced diabetes in NOD-*scid/scid* mice in the absence of functional lymphocytes," (1994) *Diabetes* 43:433-440.

Gill, R.G. et al., "CD4[+] T cells are both necessary and sufficient for islet xenograft rejection," (1994), *Transplantation Proceedings* 26:1203.

Gir, S. et al., "A numerical analysis of factor X activation in the presence of tissue factor-factor VIIa complex in a flow reactor," (1996) *Ann. Biomed. Eng.* 24(3):394-399.

Gnanou, Y et al., "Synthesis of star-shaped poly(ethylene oxide)," (1998) *Makromol. Chem.* 189:2885-2892.

Goeden-Wood, N.L. et al., "Improved assembly of multimeric genes for the biosynthetic production of protein polymers," (Jul.-Aug. 2002) *Biomacromolecules*. 3(4):874-879.

Golden, M.A., "Healing of polytetrafluoroethylene arterial grafts is influenced by graft porosity," (1990) *J. Vascular Surgery* 11(6):838-844.

Goldsmith, H.L. and Turitto, V.T., "Rheological aspects of thrombosis and haemostasis: basic principles and applications," (1986) *Thromb. Haemostasis* 55(3):415-435.

Goosen, M.F.A. (1985), Optimization of microencapsulation parameters: semipermeable microcapsules as a bioartificial pancreas, *Biotech. Bioeng.* 27:146-150.

Goosen, M.F.A. et al., "Inactivation of thrombin by antithrombin III on a heparinized biomaterial," (1980) *Thrombosis Research* 20(⅝):543-554.

Grande, D. et al., "Glycosaminoglycan mimetic biomaterials. 2. Alkene- and acrylate-derivatized glycopolymers via cyanoxyl-mediated free-radical polymerization," (2001) *Macromolecules* 34:1640-1646 (tentatively published on Web Feb. 13, 2001).

Grande, D. et al., "Glycosaminoglycan mimetic biomaterials. 1. Nonsulfated and sulfated glycopolymers by cyanoxyl-mediated free-radical polymerization," (2000) *Macromolecules* 33:1123-1125.

Grande, D. et al., "Synthesis of non-sulfated and sulfated glycopolymers," (2000) *Polymer Preprints* 41(1):1000-1001.

Gray, W.R. et al., "Molecular model for elastin structure and function," (1973) *Nature* 246:461-466.

Gruber, A. et al., "Antithrombotic effects of combining activated protein C and urokinase in nonhuman primates," (1991) *Circulation* 84(6):2454-2462.

Gruber, A et al., "Inhibition of thrombus formation by activated recombinant protein C in a primate model of arterial thrombosis," (1990) *Circulation* 82(2):578-585.

Gruber, A. et al., "Inhibition of platelet-dependent thrombus formation by human activated protein C in a primate model," (1989) *Blood* 73(3):639-742.

Hall et al., "Factor Xa generation at the surface of cultured rat vascular smooth muscle cells in an in vitro flow system," (1998) *J. Biomech. Eng.* 120(4):484-490.

Hall, B. et al., "Biomembranes as models for polymer surfaces," (1989) *Biomaterials* 10(4):219-224.

Halle I., et al. (1993) "Protection of islets of Langerhans from antibodies by microencapsulation with alginate-poly-L-lysine membranes," *Transplantation*, 44:350-4.

Hanson, S.R. et al., "Blood flow and antithrombotic drug effects," (1998) *Am. Heart Journal* 135(5 Pt 2 Su):S132-145.

Hanson, S.R. et al., "Antithrombotic effects of thrombin-induced activation of endogenous protein C in primates," (1993) *J. Clin. Invest.* 92(4):2003-2012.

Hanson, S.R. et al., "Effects of angiotensin converting enzyme inhibition with cilazapril on intimal hyperplasia in injured arteries and vascular grafts in the baboon," (1991) *Hypertension* 18(4Suppl):II-70-II-76.

Hanson, S.R. et al., "Platelet interactions with Dacron vascular grafts; a model of acute thrombosis in baboons," (1985) *Arteriosclerosis* 5(6):595-603.

Harker, L.A. et al., "Effects of megakaryocyte growth and development factor on platelet production, platelet life span, and platelet function in healthy human volunteers," (Apr. 2000) *Blood* 95(8):2514-2522.

Hasegawa, T. et al., "Quantitative analysis of uniaxial molecular orientation in Langmuir-Blodgett films by infrared relection spectroscopy," (1995) *Langmuir* 11:1236-1243.

Haskins, K. and McDuffe, M. (1990), "Acceleration of diabetes in young NOD mice with CD4[+] islet-specific T cell clone," *Science* 249:1433-1436.

Hayashi, C.Y. et al., "Hypotheses that correlate the sequence, structure, and mechanical properties of spider silk proteins," (1999) *Int. J. Biol. Macromol.* 24:271-275.

Hayashi, C. Y. and Lewis, R. V., "Evidence from flagelliform silk cDNA for the structural basis of elasticity and modular nature of spider silks," (1998) *J. Mol. Biol.* 275: 773-84.

Hayward, J.A. et al., "Biomembranes as models for polymer surfaces," (1986) *Biomaterials* 7:252-258.

Hayward, J.A. and Chapman, D., "Biomembrane surfaces as models for polymer design: the potential for haemocompatibility,"(1984) *Biomaterials* 5:135-142.

Hayzer, D.J. et al., "cDNAs encoding the baboon thrombin receptor indicate a primate transcription start site upstream of putative sites reported for the human gene," (1999) *Throm. Res.* 98:195-201.

Hayzer, D.J. et al., "Characterization of a cDNA encoding the β-chain of baboon receptor glycoprotein BPIb," (1993) *Gene* 127:271-272.

Hébert, N. et al., "A new reagent for the removal of the 4-methozybenzyl ether: application to the synthesis of unusual macrocyclic and bolaform phosphatidylcholines," (1992) *J. Org. Chem.* 57:1777-1783.

Helm, C.A. et al., "Measurement of ligand-receptor interactions," (1991) *Proc. Natl. Acad. Sci. USA* 88:8169-8173.

Hergenrother, P.J. et al., "Small-molecule microarrays: covalent attachment and screening of alcohol-containing small molecules on glass slides," (2000) *J. Am. Chem. Soc.*122:7849-7850.

Heroguez, V. et al., "Novel amphiphilic architectures by ring-opening metathesis polymerization of macromonomers," (1997) *Macromolecules* 30:4791-4798.

Huang, L. et al., "Generation of synthetic elastin-mimetic small diameter fibers and fiber networks," (2000) *Macromolecules* 33: 2989-2997 (published on Web Mar. 24, 2000).

Hubbell, J.A. et al., "Endothelial cell-selective materials for tissue engineering in the vascular graft via a new receptor," (1991) *Bio/Technology* 9:568-572.

Hudson, S.M., "The spinning of silk-like proteins into fibers," *Protein-Based Materials*, McGrath, K. and Kaplan, D., Ed.: Birkhauser: Boston, 1997, pp. 313-337.

Ishihara, K., "Novel polymeric materials for obtaining blood-compatible surfaces," (1997) *Trip* 5(12):401-407.

Ishihara, K. et al., "Synthesis of phospholipid polymers having a urethane bond in the side chain as coating material on segmented polyurethane and their platelet adhesion-resistant properties," (1995) *Biomaterials* 16:873-879.

Ishihara, K. et al., "Hemocompatibility on graft copolymers composed of poly(2-methacryloyloxyethyl phosphorylcholine) side chain and poly(*n*-butyl methacrylate) backbone," (1994) *J. Biomed. Mater. Res.* 28:225-232.

Ishihara, K. et al., "Hemocompatibility of human whole blood on polymers with a phospholipid polar group and its mechanism," (1992) *J. Biomed Mat. Res.* 26:1543-1552.

Ishihara, K. et al., "Reduced thrombogenicity of polymers having phospholipid polar groups," (1990) *J. Biomed. Mat. Res.* 24:1069-1077.

Ito Y., Section/Chapter 5.2, "Cell growth factor immobilized materials," p. 285-310; in Imanishi, Y. 1992. Synthesis of Biocomposite Materials: Chemical and Biological Modified Natural Polymers. Boca Raton, FL, CRC Press, 314 p. ISBN 0849367719.

Jackson, R.L. et al., "Glycosaminoglycans: molecular properties, protein interactions, and role in physiological processes," (1991) *Physiol. Rev.* 71(2):481-539.

Janeway, C. and Bottomly, K., "Signals and signs for lymphocyte responses," (1994) *Cell* 76:275-285.

Jarpe, A.J. et al., "Flow cytometric enumeration of mononuclear cell populations infiltrating the islets of Langerhans in prediabetic NOD mice: Development of model of autoimmune insulinitis for Type I diabetes," (1990) *Regional Immunology* 3:305-317.

Kagan, H.M. et al., "Repeat polypeptide models of elastin as substrates for lysyl oxidase," (1980) *J. Biol. Chem.* 255:3656-3659.

Kalafatis, M. et al., "Regulation and regulatory role of γ-carboxyglutamic acid containing clotting factors," (1996) *Critical Reviews in Eukaryotic Gene Expression* 6(1):87-101.

Kalafatis, M. et al., "The regulation of clotting factors," (1997) *Crit. Rev. Eukaryotic Gene Expression* 7(3):241-280.

Kawamoto et al., "Reconstituted collagen is not capable of activating factor XII but causes intrinsic coagulation by activating platelets," (1992) *Blood Coagulation & Fibrinolysis* 3(4):371-379.

Ke, Y. et al., "Ovalbumin injected with complete Freund's adjuvant stimulates cytolytic responses," (1995) *Eur. J. Immunol.* 1995:549-553.

Khaled, Md. A. et al., "Proton magnetic resonance and conformational energy calculations of repeat peptides of tropoelastin: the tetrapeptide," (1976) *J. Am. Chem. Soc.* 98: 7547-7553.

Kim, D.H. et al., "The influence of tiered layers of surface-grafted poly(ethylene glycol) on receptor-ligand-mediated adhesion between phospholipid monolayer-stabilized microbubbles and coated glass beads," (2000) *Langmuir* 16:2808-2817.

Kim, H.S. et al., "Characterizing structural changes in point-bonded nonwoven fabrics during load-deformation experiments," (Feb. 2001) *Textile Res. J.* 71(2):157-164.

Kimura, T. et al., "High-resolution solid-state $^{13}C$ nuclear magnetic resonance study of the combined process of $^1H$ spin diffusion and $^1H$ spin-lattice relaxation in semicrystalline polymers," (1992) *Polymer* 33(3):493-497.

King, G.A. et al (1987), "Alginate-polylysine microcapsules of controlled membrane molecular weight cutoff for mammalian cell culture engineering," *Biotech Progress* 3:231-240.

Kishida, A. et al., "In vivo and ex vivo evaluation of the antithrombogenecity of human thrombomodulin immobilized biomaterials," (1995) *ASAIO Journal* 41:M369-374.

Kishida, A. et al., "Immobilization of human thrombomodulin onto biomaterials," (1994) *ASAIO Journal* 40(3):M840-845.

Kishida, A. et al., "Immobilization of human thrombomodulin on biomaterials: evaluation of the activity of immobilized human thrombomodulin," (1994) *Biomaterials* 15(14):1170-1174.

Kishida, A. et al., "Immobilization of human thrombomodulin onto poly(ether urethane urea) for developing antithrombogenic blood-contacting materials," (1994) *Biomaterials* 15(10):848-852.

Kobayashi, T. et al., "Theory of the kinetics of reactions catalyzed by enzymes attached to membranes," (1974) *Biotech. Bioeng.* 16(1):77-97.

Kobayashi, T. et al., "Theory of the kinetics of reactions catalyzed by enzymes attached to the interior surfaces of tubes," (1974) *Biotech. Bioeng.* 16(1):99-118.

Köhler, A.S. et al., "Platelet adhesion to novel phospholipid materials: modified phosphatidylcholine covalently immobilized to silica, polypropylene, and PTFE materials," (1996) *J. Biomed. Mat. Res.* 32:237-242.

Kojima, M. et al., "Interaction between phospholipids and biocompatible polymers containing a phosphorylcholine moiety," (1991) *Biomaterials* 12:121-124.

Korbutt, G.S. et al., "Large scale isolation, growth, and function of porcine neonatal islet cells," (1996) *J. Clin. Invest.* 97(9):2119-2129.

Korbutt, G.S. et al., "Porcine islet cell antigens are recognized by xenoreactive natural human antibodies of both IgG and IgM subtypes," (1995) *Transplantation Proceedings* 28:821-823.

Korbutt, G.S. et al., "Successful reversal of diabetes in nude mice by transplantation of microencapsulated porcine neonatal islet cell aggregates," (1995) *Transplantation Proceedings* 27:3212.

Krejchi, M.T. et al., "Chemical sequence control of β-sheet assembly in macromolecular crystals of periodic polypeptides," (1994) *Science* 265:1427-1432.

Krych, M. et al., "Complement receptors," (1992) *Curr. Opin. Immunol.* 4:8-13.

Kuhlenschmidt, T.B. and Lee, Y.C., "Specificity of chicken liver carbohydrate binding protein," (1983) *Biochem.* 23(16):3569-3575.

Kühner, M. et al., "Lipid mono- and bilayer supported on polymer films: composite polymer-lipid films on solid substrates," (1994) *E. Biophys. J.* 67:217-226.

Lamparski et al. (1993) *J. Am. Chem. Soc.* 11:8096-8102.

Lamparski, H. et al., "Photoinduced destabilization of liposomes," (1992) *Biochemistry* 31:685-694.

Laster, J. and Silver, D., "Heparin-coated catheters and heparin-induced thrombocytopenia," (1988) *J. Vasc. Surg.* 7(5):667-672.

Lee, T.A.T. et al., "Thermo-reversible self-assembly of nanoparticles derived from elastin-mimetic polypeptides," (Aug. 2000) *Advanced Materials* 12(15):1105-1110.

Lenschow, D. et al. (1992), "Long-term survival of xenogeneic pancreatic islet grafts induced by CTLA4Ig," *Science* 257:789-795.

Lim, F. and Sun, A.M. (1980), Microencapsulated islets as a bioartificial endocrine pancreas, *Science* 210:908-910.

Lindhout, T. et al., "Antithrombin activity of surface-bound heparin studied under flow conditions," (1995) *J. Biomed. Mater. Res.* 29(10):1255-1266.

Lindner, V. et al., "Basic fibroblast growth factor stimulates endothelial regrowth and proliferation in denuded arteries," (1990) *J. Clin. Invest.* 85:2004-2008.

Loudovaris, T. et al. (1992), "The role of T cells in the destruction of xenografts within cell impermeable membranes," *Transplantation Proceedings* 24:2938.

Loykulnant, S. and Hirao, A., "Protection and polymerization of functional monomers. 30. Anionic living polymerization of 4-alkylstyrenes containing acetal-protected monosaccharide residues," (2000), *Macromolecules* 33:4757-4764.

Loykulnant, S. et al., "Protection and polymerization of functional monomers. 28. Anionic living polymerization of styrene derivatives containing acetal-protected monosaccharide residues," (1998) *Macromolecules* 31:9121-9126.

Lu, D. et al., "Comparison of activated protein C/protein S-mediated inactivation of human facor VIII and factor V," (1996) *Blood* 87(11):4708-4717.

Lvov, Y. et al., "Assembly, structural characterization, and thermal behavior of layer-by-layer deposited ultrathin films of poly(vinyl sulfate) and poly(allylamine)," (1993) *Langmuir* 9:481-486.

MacDonald, R.C. et al., "Small-volume extrusion apparatus for preparation of large, unilamellar vesicles," (1991) *Biochim. Biophys. Acta* 1061:297-303.

Mann, K.G. et al., "Cofactor proteins in the assembly and expression of blood clotting enzyme complexes," (1988) *Ann. Rev. Biochemistry* 57:915-956.

Mao, G., et al., "Interactions, structure, and stability of photoreactive bolaform amphiphile multilayers," (1995) *Langmuir* 11:942-952.

Maoz et al. (1984) "On the formation and structure of self-assembling monolayers," *J. Colloid Interface Sci.* 100(2):456.

Markovich, R.J. et al., "Silica subsurface amine effect on the chemical stability and chromatographic properties of end-capped immobilized artificial membrane surfaces," (1991) *Anal. Chem.* 63:1851-1860.

Marra, K.G. et al., "Cytomimetic biomaterials. 1. In-Situ polymerization of phospholipids on an alkylated surface," (1997) *Macromolecules* 30:6483-6488.

Marra, K.G. et al., "Cytomimetic biomaterials. 2. In-Situ polymerization of phospholipids on a polymer surface," (1997) *Langmuir* 13:5697-5701.

Marra, K.G. et al., "Stabilized phosphatidylcholine surfaces via in-situ polymerization at a solid-liquid interface," (1997) *Polymer Preprints* 38(2):682-683.

Marsh, A. et al., "Atom transfer polymerization: use of uridine and adenosine derivatized monomers and initiators," (1999) *J. Macromolecules* 32:8725-8731.

Martin, D.C. et al., "Processing and Characterization of Protein Polymers," *Protein-Based Materials*, McGrath, K. and Kaplan, D., Eds.; Birkhauser: Boston, 1997, pp. 339-370.

Martin, S.F. et al., "General method for the synthesis of phospholipid derivatives of 1,2-*O*-diacyl-*sn*-glycerols," (1994) *J. Org. Chem.* 59:4805-4820.

Massia, S.P. and Hubbell, J.A., "Vascular endothelial cell adhesion and spreading promoted by the peptide REDV of the IIICS region of plasma fibronectin is mediated by integrin $α_2β_1$," (1992) *J. Biol. Chem.* 267:14019-14026.

Matthew, H.W. et al (1993) "Complex coacervate microcapsules for mammalian cell culture and artificial organ development," *Biotechnol. Prog.* 9:510-519.

Mauk, A.W. et al., "Structural characterization of self-assembled lipid monolayers by NπT simulation," (1998) *Langmuir* 14:5255-5266.

Mauk, M.R. et al., "Vesicle targeting: timed release and specificity for leukocytes in mice by subcutaneous injection," (1980) *Science* 207:309-311.

McLean, L.R. et al., "Preparation of stable polar surfaces using polymerizable long-chain diacetylene molecules," (1983) *Thin Solid Films* 99:127-131.

McMillan R.A. and Conticello, R. P., "Synthesis and characterization of elastin-mimetic protein gels derived from a well-defined polypeptide precursor," (2000) *Macromolecules* 33:4809-4821.

McMillan, R.A. et al., "High-resolution topographic imaging of environmentally responsive, elastin-mimetic hydrogels," (1999) *Macromolecules* 32:9067-9070.

McMillan, R.A. et al., "Rapid assembly of synthetic genes encoding protein polymers," (1999) *Macromolecules* 32: 3643-3648.

McPherson, D.T. et al., "Product purification by reversible phase transition following *Eschericia coli* expression of genes encoding up to 251 repeats of the elastomeric pentapeptide GVGVP," (1996) *Protein Expression Purification* 7: 51-57.

McPherson, D.T. et al., "Production and purification of a recombinant elastomeric polypeptide, G-(VPGVG)$_{19}$-VPGV, from *Escherichia coli*," (1992) *Biotechnology Progress* 8:347-352.

Merrill, E.W. et al., "Polyvinyl alcohol-heparin hydrogel 'G'," (1970) *J. Applied Physiology* 29(5):723-730.

Meuse, C. W. et al., "Hybrid bilayer membranes in air and water: infrared spectroscopy and neutron reflectivity studies," (1998) *Biophys J.* 74:1388-1398.

Mielczarski, J.A. and Yoon, R.H., "Fourier transform infrared external reflection study of molecular orientation in spontaneously adsorbed layers on low-absorption substrates," (1989) *J. Phys. Chem.* 93:2034-2038.

Miller, B. et al., "Both the Lyt-2+ and L3T4+ T cell subsets are required for the transfer of diabetes in nonobese diabetic mice" (1988) *J. Immunol.* 140:52-8.

Minoda, M. et al. "Synthesis of functional polymers bearing pendant mono- and oligo- saccharide residues," *Macromol. Symp.* 99:169-177 (1995).

Miyata, T. and Nakamae, K., "Polymers with pendent saccharides—'glycopolymers'," (1997) *Trends Polym. Sci.* 5:198-206.

Miyoshi, M. et al., "A rapid formation of lysine-derived crosslinks by chick embryo aorta," (1976) *J. Biochem.* (Tokyo) 79: 235-1243.

Monshipouri, M. and Rudolph, A.S., "Liposome-encapsulated alginate: controlled hydrogel particle formation and release," (1995) *J. Microencapsulation* 12(2):117-127.

Moore et al., (1983) *Macromolecules* 16:335-338.

Moses, R. et al. (1990), "Xenogeneic proliferation and lymphokine production are dependent upon CD4+ helper T cells and self antigen-presenting cells in the mouse. I," *Exp. Med.* 172:567-75.

Moya, S. et al., "Lipid coating on polyelectrolyte surface modified colloidal particles and polyelectrolyte capsules," (2000) *Macromolecules* 33:4538-4544.

Müller-Eberhard, H.I., "Molecular organization and function of the complement system," (1988) *Ann. Rev. Biochem.* 57:321-347.

Nagahori, N. and Nishimura, S-I., "Tailored glycopolymers: controlling the carbohydrate-protein interaction based on template effect," (2001) *Biomacromolecules* 2:22-24 (published on Web Dec. 28, 2000).

Nagle, J.F. et al., "X-ray structure determination of fully hydrated L$_\alpha$ phase dipalmitoylphosphatidylcholine bilayers," (1996) *Biophys. J.* 70:1419-1431.

Nah, J-W et al., "Polymeric micelle formation of multiblock copolymer composed of poly(γ-benzyl ∠-glutamate) and poly(ethylene oxide)," (2000) *Bull. Korean Chem. Soc.* 21(4):383-388.

Nah, J-W et al., Drug-delivery system based on core-shell-type nanoparticles composed of poly(γ-benzyl ∠-glutamate) and poly-(ethylene oxide), (2000) *J. App. Polymer Sci.* 75:115-1126.

Nemerson, Y. and Turitto, V.T., "The effect of flow on hemostasis and thrombosis," (1991)*Thromb. Haemostasis* 66(3):272-276.

Nickerson, P. et al., "Analysis of cytokine transcripts in pancreatic islet cell allografts during rejection and tolerance induction," (1993) *Transplantation Proceedings* 25:984-985.

Nojiri, C. et al., "Can heparin immobilized surfaces maintain nonthrombogenic activity during in Vivo long-term implantation?" (1996) *ASAIO Journal* 42(5):M468-475.

Nojiri, C. et al., "In vivo nonthrombogenicity of heparin immobilized polymer surfaces," (1990) *ASAIO Transactions* 36(3):M168-172.

Nomura, K. and Schrock, R.R., "Preparation of 'sugar-coated' homopolymers and multiblock ROMP copolymers," (1996) *Macromolecules* 29:540.

O'Brien, D.F. et al., "Polymerization of preformed self-organized assemblies," (1998) *Acc. Chem. Res.* 31:861-868.

O'Connell, P.J. et al., "Unmodified pancreatic islet allograft rejection results in the preferential expression of certain T cell activation transcripts," (1993) *J. Immunol.* 150:1093-1104.

O'Donnell, J. H. and Whittaker, A. K., "Radiation degradation of linear low density polyethylene: determination of lamellae thickness, crystallinity and crosslinking by solid-state $^{13}$C NMR and DSC," (1992) *Radiat. Phys. Chem.* 36(20:209-214.

O'Donnell, J. H. and Whittaker, A. K., "A solid-state $^{13}$C-NMR study of crosslinking in polybutadiene by γ radiation: effect of microstructure and dose," (1992) *J. Polym. Chem. Ed.* 30:185-195.

Ohno, K. et al., "Nitroxide-controlled free radical polymerization of a sugar-carrying acryloyl monomer," (1999) *Macromol. Chem. Phys.* 200:1619-1625.

Ohno, K. et al., "Synthesis of a well-defined glycopolymer by nitroxide-controlled free radical polymerization," (1998) *Macromolecules* 31:1064.

Ohno, K. et al., "Synthesis of a well-defined glycopolymer by atom transfer radical polymerization," (1998) *J. Polym. Sci., Part A: Polym. Chem.* 36:2473-2481.

Ohno, K. et al., "Free radical polymerization of a sugar residue-carrying styryl monomer with a lipophilic alkoxyamine initiator: synthesis of a well-defined novel glycolipid," (1998) *Macromol. Chem. Phys.* 199:2193-2197.

Ohno, H. et al., "Polymerization of liposomes composed of diene-containing lipids by UV and radical initiators: evidence for the different chemical environment of diene groups on 1- and 2-acyl chains," (1987) *Macromol.* 20:929-933.

Ohno et al., "Polymerization of liposomes composed of diene-containing lipids by radical initiators. II. Polymerization of monodiene-type lipids as liposomes," (1987) *J. Polym. Sci.: Part A: Polym. Chem.* 25:2737-2746.

Orban, J.M. et al., "Cytomimetic biomaterials. 4. In-situ photo polymerization of phospholipids on an alkylated surface," (2000) *Macromolecules* 33:4205-4212 (published on Web May 6, 2000).

Ornitz, D.M. et al., "FGF binding and FGF receptor activation by synthetic heparan-derived di- and trisaccharides," (1995) *Science* 268:432-434.

Otani et al., "Rapidly curable biological glue composed of gelatin and poly(L-glutamic acid)," (1996) *Biomaterials* 17(14):1387-1391.

Owen, W.G. and Esmon, C.T., "Functional properties of an endothelial cell cofactor for thrombin-catalyzed activation of protein C," (1981) *J. Biol. Chem.* 256(11):5532-5535.

Packer, K. J. et al., "The effects of morphology on $^1$H NMR spectra and relaxation in semicrystalline polyolefins," (1984) *J. Polym. Sci.: Polym. Phys.* 22:589-616.

Panitch, A. et al., "Design and biosynthesis of elastin-like artificial extracellular matrix proteins containing periodically spaced fibronectin CS5 domains," (1999) *Macromolecules* 32:1701-1703.

Parikh, A.N. et al., "An intrinsic relationship between molecular structure in self-assembled *n*-alkysiloxane monolayers and deposition temperature," (1994) *J. Phys. Chem.* 98:7577.

Parker, W. et al., "Transplantation of discordant xenografts: a challenge revisited," (1996) *Immunology Today* 17:373-378.

Pasquali-Ronchetti et al., "Study of elastic fiber organization by scanning force microscopy," (1998) *Matrix Biology* 17:75-83.

Pasquali-Ronchetti et al., "Ultrastructure of elastin," (1995) *Ciba Foundation Symposium* 192:31-50.

Pearce, K.H. et al., "Comparison of the membrane binding kinetics of bovine prothrombin and its fragment 1," (1993) *J. Biol. Chem.* 268:22984-22991.

Peterson, I.D., and Haskins, K. (1996), "Transfer of diabetes in the NOD-*scid* mouse by CD4 T-cell clones: differential requirement for CD8 T-cells," *Diabetes* 45:328-36.

Petka, W.A. et al., "Reversible hydrogels from self-assembling artificial proteins," (1998) *Science* 281:389-392.

Petitou, M. et al., "Synthesis of thrombin-inhibiting heparin mimetics without side effects," (1999) *Nature* 398:417-422.

Petitou, M. et al., "First synthetic carbohydrates with the full anticoagulant properties of heparin," (1998), *Chem. Int. Ed.* 37:3009-3014.

Pierson, R. et al. (1989), "CD4$^+$ lymphocytes play a dominant role in murine xenogeneic responses," *Transplantation Proceedings* 21:519.

Plant, A.L. et al., "Phospholipid/alkanethiol bilayers for cell-surface receptor studies by surface plasmon resonance," (1995) *Anal. Biochem.* 226:342-348.

Plant, A. L., "Self-assembled phospholipid/alkanethiol biomimetic bilayers on gold," (1993) *Langmuir* 9: 2764-2767.

Plant, A.L. et al., "Generic liposome reagent for immunoassays," (1989) *Anal. Biochem.* 176:420-426.

Ponpipom, M.M. and Bugianesi, R.L., "Isolation of 1,3-distearoyl-glycero-2- phosphocholine (β-lecithin) from commercial 1,2-distearoyl-*sn*-glycero-3-phosphocholine," (1980) *Lipid Res.* 21:136-139.

Pourdeyhimi, B. et al., "Measuring fiber diameter distribution in nonwovens," (1999) *Textile Res. J.* 69:233-236.

Qiu, Z-H. and Leslie, C.C., "Protein kinase C-dependent and -independent pathways of mitogen-activated protein kinase activation in macrophages by stimuli that activate phospholipase $A_2$," (1994) *J. Biol. Chem.* 269:19480-19487.

Rand, M.D. et al., "Blood clotting in minimally altered whole blood," (1996) *Blood* 88(9):3432-3445.

Rapaka, R.S. et al., "Non-elastomeric polypeptide models of elastin," (1978) *Int. J. Pept. Protein Res.* 11:109-127.

Regen, S.L. et al., "Polymer-supported membranes. A new approach for modifying polymer surfaces," (1983) *Macromolecules* 16:335-338.

Reneker, D.H. and Chun, I., "Nanometre diameter fibres of polymer, produced by electrospinning," (1996) *Nanotechnology* 7: 216-223.

Reneker, D.H. and Srinivasan, G., "Electrospun polyaramid fibers: structure and morphology," (1995) *Bull Am. Phys. Soc.* 40:351.

Rifkin, D.B. and Moscatelli, D., "Recent developments in the cell biology of basic fibroblast growth factor," (1989) *J. Cell. Biol.* 109:1-6.

Ringsdorf et al., "Molecular architecture and function of polymeric oriented systems: models for the study of organization, surface recognition, and dynamics of biomembranes," (1988) *Angew. Chem. Int. Ed. Engl.* 27:113-158.

Roach, M.R. and Burton A.C., "The reason for the shape of the distensibility curves of arteries," (1957) *Can. J. Biochem. Physiol.* 35:681-690.

Roberts, I. et al. (1996), "Dopamine secretion by PC12 cells microencapsulated in a hydroxymethyl methacrylate-methyl methacrylate copolymer," *Biomaterials* 17:267-275.

Robins, S. P., "Analysis of the crosslinking components in collagen and elastin," (1982) *Methods Biochem. Anal.* 28:329-379.

Rosen, E.M. et al., "Regulation of motility in bovine brain endothelial cells," (1991) *J. Cell Physiol.* 146:325-35.

Roy, B.C. et al., "Synthesis and fluorescence properties of new fluorescent, polymerizable, metal-chelating lipids," (2000) *J. Org. Chem.* 65:3644-3651.

Roy, R., "Recent developments in the rational design of multivalent glycoconjugates," (1997) *Topics in Current Chem.* 187:241-274.

Roy, R., "Syntheses and some applications of chemically defined multivalent glycoconjugates," (1996) *Current Opinion in Structural Biology* 6:692-702.

Sabatani, E. and Rubinstein, I., "Organized self-assembling monolayers on electrodes. 2. Monolayer-based ultramicroelectrodes for the study of very rapid electrode kinetics," (1987) *J. Phys. Chem.* 91:6663-6669.

Sackmann, E. and Tanaka, M., Supported membranes on soft polymer cushions: fabrication, characterization and applications, (2000) *Trans Biotechnol.* 18:58-64.

Sadler, J.E., "Thrombomodulin structure and function," (1997) *Thromb. Haemostasis* 78(1):392-395.

Sakai, H. and Umemura, J., "Molecular orientation in Langmuir films of 12-hydroxystearic acid studied by infrared external-reflection spectroscopy," (1998) *Langmuir* 14:6249-6255.

Sakata, Y., et al., "Activated protein C stimulates the fibrinolytic activity of cultured endothelial cells and decreases antiactivator activity," (1985) *Proc. Natl. Acad. Sci. USA* 82(4):1121-1125.

Sandberg, L.B. et al., "Elastin covalent structure as determined by solid phase amino acid sequencing," (1985) *Pathol. Biol.* 33:266-274.

Sandberg, L.B. et al., "Elastin structure, biosynthesis, and relation to disease states," (1981) *N. Engl. J. Med.* 304:566-579.

Sandberg, L.B. et al., "Primary structure of porcine tropoelastin," (1977) *J. Adv. Exp. Med. Biol.* 79:277-284.

Santin, M. et al., "Synthesis and characterization of a new interpenetrated poly(2-hydroxyethylmethacrylate)-gelatin composite polymer," (1996) *Biomaterials* 17(15):1459-1467.

Sato, Y. and Rifkin, D.B., "Autocrine activities of basic fibroblast growth factor: regulation of endothelial cell movement, plasminogen activator synthesis, and DNA synthesis," (1988) *J. Cell. Biol.* 107:1199-1205.

Schmidt, R.R., "Recent developments in the synthesis of glycoconjugates," (1989) *Pure Appl. Chem.* 61(7):1257-70.

Sefton, M.V., (1989), *Can. J. Chem. Eng.* 67:705-712.

Seifert, K. et al., "Charge transport by ion translocating membrane proteins on solid supported membranes," (1993) *Biophys. J.* 64:384-391.

Seitz, M. et al., "Formation of tethered supported bilayers via membrane-inserting reactive lipids," (1998) *Thin Solid Films* 329:767-771.

Sells, T.D. & O'Brien, D.F., "Two-dimensional polymerization of lipid bilayers: degree of polymerization of acryloyl lipids," (1994) *Macromolecules* 27:226-233.

Serruys, P.W. et al., "Randomised comparison of implantation of heparin-coated stents with balloon angioplasty in selected patients with coronary artery disease (Benestent II)," (1998) *Lancet* 352:673-681.

Shen, W. W. et al., "Polymer-supported lipid bilayers on benzophenone-modified substrates," (2001) *Biomacromolecules* 2:70-79.

Shi, X. and Caruso, F., "Release behavior of thin-walled microcapsules composed of polyelectrolyte multilayers," (2001) *Langmuir* 17:2036-2042.

Shoji, M. et al., "Human and baboon integrin $\beta_5$ subunit-encoding mRNAs have alternative polyadenylation sites," (1993) *Gene* 133:307-308.

Shultz, L. et al., "Multiple defects in innate and adaptive immunologic function in NOD/LtSz-*scid* mice," (1995) *J. Immunology* 154:180-191.

Siedlecki, C.A. et al., "Interactions of human von Willebrand factor with a hydrophobic self-assembled monolayer studied by atomic force microscopy," (1994) *Biomed. Mater. Res.* 28:971.

Slack, S.M. et al., "The effects of flow on blood coagulation and thrombosis," (1993) *Thromb. Haemostasis* 70(1):129-134.

Slack, S.M. and Turitto, V.T., "Flow chambers and their standardization for use in studies of thrombosis," (1994) *Thromb. Haemostasis* 72(5):777-781.

Smirnov, M.D. et al., "The effect of membrane composition on the hemostatic balance," (1999) *Biochemistry* 38(12):3591-3598.

Smirnov, M.D. and Esmon, C.T., "Phosphatidylethanolamine incorporation into vesicles selectively enhances factor Va inactivation by activated protein C," (1994) *J. Biol. Chem.* 269(2):816-819.

Snyder, R.G. et al., "Vibrational spectra in the C—H stretching region and the structure of the polymethylene chain," (1978) *Spectrochim. Acta, Part A* 34A:395-406.

Solletti, J.M. et al., "Elaboration and characterization of phospholipid Langmuir-Blodgett films," (1996) *Langmuir* 1:5379-5386.

Spinke, J. et al., "Polymer-supported bilayer on a solid substrate," (1992) *Biophys. J.* 63:1667-1671.

Stoll, M.S. et al., "Improved procedure for the construction of neoglycolipids having antigenic and lectin-binding activities, from reducing oligosaccharides," (1988) *Biochemical J.* 256:661-664.

Sun, F. et al., "Ultrathin self-assembled polymeric films on solid surfaces. 2. Formation of 11-(n-pentyldithio)undecanoate-bearing polyacrylate monolayers on gold," (1993) *Langmuir* 9:3200-3207.

Sun, F. et al., "Spontaneous polymer thin film assembly and organization using mutually immiscible side chains," (1996) *J. Am. Chem. Soc.* 118:1856-1866.

Sun, F. et al., "Ultrathin self-assembled polymeric films on solid surfaces. III. Influence of acrylate dithioalkyl side chain length on polymeric monolayer formation on gold," (1994) *J. Vac. Sci. Technol.* 12:2499.

Sun, L. and Chaikof, E.L., "The synthesis of neoglycophospholipid conjugates via reductive amination of ω-oxoalkylglycosides and phosphatidylethanolamines," (1998) *Carbohydrate Res.* 370:77-81.

Sun, L. and Chaikof, E.L., "Neoglycophospholipids with alkyl spacers: synthesis via an improved reductive amination and monolayer properties," (1997) *Bioconjugate Chem.* 8:567-571.

Sun, Y. et al. (1996), "Normalization of diabetes in spontaneously diabetic cynomologus monkeys by xenografts of microencapsulated porcine islets without immunosuppression," *J. Clin. Invest.* 98:1417-1422.

Takeuchi, T. et al. (1992), "Heart allografts in murine systems: The differential activation of Th2-like effector cells in peripheral tolerance," *Transplantation* 53:1281-1294.

Tasumi, M.S. and Miyaza, T.J., "Normal vibrations and force constants of polymethylene chain," (1962) *J. Mol. Spectrosc.* 9:261-287.

Tendian, S.W. et al., "Evidence from total internal reflection fluorescence microscopy for calcium-independent binding of prothrombin to negatively charged planar phospholipid membranes," (1991) *Biochemistry* 30:10991-10999.

Terranova, V.P. et al., "Human endothelial cells are chemotactic to endothelial cell growth factor and heparin," (1985) *Cell Biol.* 101:2330-2334.

Thomas, G.J. and Prescott, B., "Raman amide bands of type-II β-turns in cyclo-(VPGVG)$_3$ and poly-(VPGVG), and implications for protein secondary-structure analysis," (1987) *Biopolymers* 26:921-934.

Toshima, K. and Tatsuta, K., "Recent progress on O-glycosylation methods and its application to natural products synthesis," (1993) *Chem. Rev.* 93:1503-1531.

Turitto, V.T. and Hall, C.L., "Mechanical factors affecting hemostasis and thrombosis," (1998) *Thromb. Res.* 92(6 Suppl.2):S25-310.

Ueda, T. et al., "Preparation of 2-methacryloyloxyethyl phosphorylcholine copolymers with alkyl methacrylates and their blood compatibility," (1992) *Polym. J.* 24(11):1259-1269.

Uludag, H. and Sefton, M.V., "Metabolic activity and proliferation of CHO cells in hydroxyethyl methacrylate-methyl methacrylate (HEMA-MMA) microcapsules," (1993) *Cell Transplantation* 2:175-182.

Urry, D.W. et al., "Protein-based materials with a profound range of properties and applications: the elastin $\Delta T_t$ hydrophobic paradigm," K. McGrath and D. Kaplan, Ed., Birkhauser: Boston, (1997), pp. 133-177.

Urry, D.W. et al., "Molecular biophysics of elastin structure, function and pathology," (1995) *Ciba Foundation Symposium* 192:4-30.

Urry, D.W., "Molecular machines: how motion and other functions of living organisms can result from reversible chemical changes," (1993) *Angew. Chem. Int. Ed. Engl.* 32:819-841.

Urry, D.W. et al., "Two-dimensional proton NMR studies on poly(VPGVG) and its cyclic conformational correlate, cyclo(VPGVG)$_3$," (1989) *Biopolymers* 28:819-833.

Urry, D.W., "Entropic elastic processes in protein mechanisms. I. Elastic structure due to an inverse temperature transition and elasticity due to internal chain dynamics," (1988) *J. Prot. Chem.* 7(1):1-34.

Urry, D.W. et al., "Polytetrapeptide of elastin," (1986) *Int. J. Pept. Protein Res.* 28:649-660.

Urry, D.W. et al., "Polypentapeptide of elastin: temperature dependence of ellipticity and correlation with elastomeric force," (1985) *Biochem. Biophys. Res. Commun.* 130:50-57.

Urry, D.W. et al., "Phase-structure transitions of the elastin polypentapeptide-water system within the framework of composition-temperature studies," (1985) *Biopolymers* 24:2345-2356.

Urry, D.W. et al., "Studies on the conformation and interactions of elastin secondary structure of synthetic repeat hexapeptides," (1975) *Biochim. Biophys. Acta* 393:296-306.

Urry, D.W. et al., "Studies on the conformation and interactions of elastin. Proton magnetic resonance of the repeating pentapeptide," (1974) *Biochemistry* 13:609-616;.

van Ackern, F. et al., Ultrathin membranes for gas separation and pervaporation prepared upon electrostatic self-assembly of polyelectrolytes, (998) *Thin Solid Films* 329:762-766.

Van Boeckel, C.A.A. et al., "The unique antithrombin III binding domain of heparin: a lead to new synthetic antithrombotics," (1993) *Chem. Int. Ed. Engl.* 32(12):1671-1690.

Van Den Bulcke, A.I. et al., "Structural and rheological properties of methacrylamide modified gelatin hydrogels," (2000) *Biomacromolecules* 1:31-38.

Vanderhart, D. L., "Proton spin diffusion as a tool for characterizing polymer blends," (1990) *Makromol. Chem., Macromol. Symp.* 34:125-159.

van't Veer, C. et al., "Inhibitory mechanism of the protein C pathway on tissue factor-induced thrombin generation," (1997) *J. Biol. Chem.* 272(12):7983-7984.

Vasilets, V.N. et al., "Microwave $CO_2$ plasma-initiated vapour phase graft polymerization of acrylic acid onto polytetrafluoroethylene for immobilization of human thrombomodulin," (1997) *Biomaterials* 18(17):1139-1145.

Viitala, T. et al., "Protein immobilization to a partially cross-linked organic monolayer," (2000) *Langmuir* 16:4953-4961.

Wall, R.T. et al., "Human endothelial cell migration: stimulation by a released platelet factor," (1978) *Lab Invest.* 39(5):523-529.

Wang, P. et al., "Synthesis of phospholipid-inhibitor conjugates by enzymatic transphosphatidylation with phospholipase D," (1993) *J. Am. Chem. Soc.* 115:10487-10491.

Wasserman, Z.R. and Salemme, F.R., "A molecular dynamics investigation of the elastomeric restoring force in elastin," (1990) *Biopolymers* 29:1613-1631.

Wasserman, S.R. et al., "The structure of self-assembled monolayers of alkylsiloxanes on silicon: a comparison of results from ellipsometry and low-angle X-ray reflectivity," (1989) *J. Am. Chem. Soc.* 111:5852-5861.

Weber, C.J. et al., "CTLA4-Ig prolongs survival of microencapsulated neonatal porcine islet xenografts in diabetic NOD mice," (1997) *Cell Transplantation* 6(5):505-508.

Weber, C.J. et al.,"Encapsulated islet iso-, allo-, and xenografts in diabetic NOD mice," (1995) *Transplantation Proceedings* 27:3308-3311.

Weber, C. et al. (1994), "NOD mouse peritoneal cellular response to poly-L-lysine-alginate microencapsulated rat islets," *Transplantation Proceedings* 26: 1116-1119.

Weber, C. et al. (1990), "Microencapsulated dog and rat islet xenografts into streptozotocin-diabetic and NOD mice," *Horm. Metab. Res.* 35:219-226.

Weber, C.I. et al. (1990), "The role of CD4+ helper T cells in destruction of microencapsulated islet xenografts in NOD mice," *Transplantation* 49(2):396-404.

Weiner, A.L. et al., (1985), "Liposome-collagen gel matrix: a novel sustained drug delivery system," *J. Pharm. Sci.* 74(9):922-925.

Welsh, E. R. and Tirrell, D. A., "Engineering the extracellular matrix: A novel approach to polymeric biomaterials. I. Control of the physical properties of artificial protein matrices designed to support adhesion of vascular endothelial cells," (2000) *Biomacromolecules* 1:23-30.

Westerduin, P. et al., "Synthesis of tailor-made glycoconjugates showing AT III-mediated inhibition of blood coagulation factors Xa and thrombin," (1996) *Chem. Int. Ed. Engl.* 35:331-333.

Westman, J. et al., "Synthesis and fibroblast growth factor binding of oligosaccharides related to heparin and heparan sulphate," (1995) *J. Carbohydr. Chem.* 14:95-113.

Wick et al., "Unusually large von Willebrand factor multimers increase adhesion of sickle erythrocytes to human endothelial cells under controlled flow," (1987) *J. Clin. Invest.* 80:905-910.

Wilbur, D.S. et al., "Biotin reagents for antibody pretargeting. 4. Selection of biotin conjugates for in vivo application based on their dissociation rate from avidin and streptavidin," (2000) *Bioconjugate Chem.* 11:569-583.

Winger, T.M. et al., "Formation and stability of complex membrane-mimetic monolayers on solid supports," (1999) *Langmuir* 15:3866-3874.

Winger, T.M. and Chaikof, E.L., "Synthesis and characterization of supported phospholipid monolayers: a correlative investigation by radiochemical titration and atomic force microscopy," (1998) *Langmuir* 14:4148-4155.

Winger, T.M. and Chaikof, E.L., "Synthesis and characterization of supported bioactive lipid membranes," In: *Materials Science of the Cell*, A. Plant and V. Vogel (Ed.), MRS Publications, Pittsburgh (1998), pp. 113-118.

Winger T.M. et al., "Behavior of lipid-modified peptides in membrane-mimetic monolayers at the air/water interface," (1997) *Langmuir* 13:3256-3259.

Winger T.M. et al., Lipopeptide conjugates: Biomolecular building blocks for receptor activating membrane-mimetic structures. (1996) *Biomaterials* 17:443-449.

Winger, T.M. et al., "A convenient route to thiol terminated peptides for conjugation and surface functionalization strategies," (1995) *Bioconjug. Chem.* 6:323-326.

Winger, T.M. et al., Purification of synthetic lipopeptide conjugates by liquid chromatography, (1995) *J. Liquid Chromatogr.* 18:4117-4125.

Winger, T.M. et al. (1995) *Biomaterials* 16:443-449.

Wong, J.S. & Yen, Y.S., "Intriguing absorption band behavior of IR reflectance spectra of silicon dioxide on silicon," (1988) *Appl. Spectrosc.* 42(4):598-604.

Wright, E.R. and Conticello, V.P., "Self-assembly of block copolymers derived from elastin-mimetic polypeptide sequences," (Oct. 2002) *Adv. Drug Deliv. Rev.* 54(8):1057-1073.

Wright, E.R. et al., "Thermoplastic elastomer hydrogels via self-assembly of an elastin-mimetic triblock polypeptide," (Feb. 2002) *Adv. Fund. Mater.* 12:149-154.

Xiao, X-D et al., "Preparation, structure, and mechanical stability of alkylsilane monolayers on mica," (1995) *Langmuir* 11(5):1600-1604.

Yamada, K. et al., "Controlled synthesis of amphiphilic block copolymers with pendant N-acetyl-D-glucosamine residues by living cationic polymerization and their interaction with WGA lectin," (1999) *Macromolecules* 32:3553.

Yamada, K. et al., "Controlled synthesis of glycopolymers with pendant D-glucosamine residues by living cationic polymerization," (1997) *J. Polym. Sci. Part A: Polym. Chem.* 35:751-757.

Yen, Y.-S. and Wong, J. (1989) J. Phys. Chem. 93:7208-7216.

Yoshioko, T. et al., "Encapsulation of mammalian cell with chitosan-CMC capsule," (1990) *Biotechnol. Bioeng.* 35:66-72.

Yu, S.M. et al., "Smectic ordering in solutions and films of a rod-like polymer owing to monodispersity of chain length," (1997) *Nature* 389:167-170.

Zhang, H. et al., "Synthesis of 4% glu-containing Val$^1$ and Ile$^1$-polypentapeptides: model protein systems for demonstrating mechanochemical coupling," (1989) *J. Protein Chem.* 8:173-182.

Zierler et al., "Accuracy of duplex scanning for measurement of arterial volume flow," (1992) *J. Vasc. Surg.* 16(4):520-526.

US 5,556,632, 09/1996, Kohler et al. (withdrawn)

* cited by examiner

BIOLOGICAL COMPONENT COMPRISING ARTIFICIAL MEMBRANE

CROSS-REFERENCE TO RELATED APPLICATIONS

This application claims priority to PCT Application PCT/US01/24020 filed July 30, 2001, which claims benefit of U.S. provisional application Ser. Nos. 60/221,828, 60/221,618, and 60/221,655, all filed on July 28, 2000.

STATEMENT REGARDING FEDERALLY SPONSORED RESEARCH OR DEVELOPMENT

This invention was made with government support under NIH Contract No. RR14190 awarded by the National Institutes of Health. The government has certain rights in the invention.

BACKGROUND OF THE INVENTION

Several approaches have been proposed for improving the biocompatibility of biomaterials useful in medical applications. For example, modifying the biomaterial surface to provide either low polarity or ionic charge or coating the surface with biological substances such as cells, proteins, enzymes, etc., has been used to prevent undesirable protein adhesion. Another approach involves the incorporation of an anticoagulant into the biomaterial, rendering the biomaterial antithrombogenic. A further approach involves the incorporation of various phospholipids into the biomaterial. An additional approach involves the binding of a heparin-quaternary amine complex, or other antithrombotic agent, to the biomaterial surface However, many of these methods have the disadvantage of being nonpermanent systems in that the surface coating is eventually stripped off or leached away. For example, heparin, which is complexed to the biomaterial surface, is not only gradually lost from the polymer surface into the surrounding medium but also has limited bioactivity due to catabolism and its inherent instability under physiological conditions.

Membranes, as self-organizing noncovalent aggregates, offer a model for molecular engineering in which the constituent members can be controlled, modified, precisely defined, and easily assembled. During the past decade, phospholipids differing in chemical composition, saturation, and size have been utilized as building blocks in the design of a variety of structures of complex geometry. Lipid-based cylinders, cubes, and spheres have found applications in both drug delivery and as templates for composite molecularly engineered structures. Surface-coupled bilayers for biosensor applications have also been produced by assembling a layer of closely packed hydrocarbon chains onto an underlying substrate followed by exposure to either a dilute solution of emulsified lipids or unilamellar lipid vesicles (Spinke et al. [1992] *Biophys. J.* 63:1667-1671; Seifert et al. [1993] *Biophys. J.* 64:384-393; and Florin et al. [1993] *Biophys. J.* 64:375-383). In addition, Langmuir-Blodgett techniques have been used as an alternate strategy to construct supported bilayers via a process of controlled dipping of a substrate through an organic amphiphilic monolayer (Ulman, A. [1991] "An Introduction to Ultrathin Organic Films from Langmuir-Blodgett to Self-assembly," New York, Academic Press). Remarkably, these noncovalent molecular assemblies exhibit a high degree of stability. A force of 26 kT is required to remove a double chained C-16 phosphatidylcholine molecule from a bilayer into water (Cecv, G. and Marsh, D. [1987] "Phospholipid Bilayers," New York, Wiley; and Helm et al. [1991] *Proc. Natl. Acad. Sci. USA* 88:8169-8173). This nearly approximates the biotin-streptavidin bond energy of 35 kT and is several orders of magnitude greater than the strength of typical monoclonal antibody-antigen interactions. Thus, the significance of the methodologies of the present invention lies in the ability to engineer relatively robust materials with an unparalleled level of reproducibility and molecular control over surface order and chemistry.

In order to create robust surface structures, most membrane-mimetic systems for blood-contacting applications have been designed as copolymers containing the phosphorylcholine functional group in either side chains or, less frequently, the polymer backbone (Kojima et al. [1991] *Biomaterials* 12:121; Ueda, T. et al., [1992]*Polym. J.* 24:1259; Ishihara, K. et al. [1995] Biomaterials 16:873; Campbell et al. [1994] *ASAIO J.* 40(3):M853; Chen et al. [1996] *J. Appl. Polym. Sci.* 60:455; and Yamada et al. [1995] *JMS Pure Appl. Chem.* A32:1723). While these materials have improved stability and promising blood-contacting properties have been reported, a number of limitations exist. In particular, the ability to engineer surface properties on a molecular level, by taking advantage of the principal of self-organization intrinsic to amphiphilic molecules, is lost. In addition, the ability to early incorporate diverse biomolecular functional groups into the membrane-mimetic surface is also lost.

A significant limitation in the widespread use of supported biomembranes is their limited stability for most applications outside of a laboratory environment. In order to generate more robust systems, strategies have been developed to tether membranes to an underlying substrate, such as gold or glass with or without an intervening flexible spacer or polymer cushion (Spinke, J. Y. et al. (1992) *Biophys. J.* 63:1667-1671; Florin, E.-L. and Gaub, H. E. (1993) Biophys. J 64:375-383; Meuse, C. W. et al, (1998) *Biophys J* 74:1388-1398; Seitz, M. et al. (1998) *Thin Solid Films* 329:767-771; Beyer, D. et al. (1996) Thin Solid Films 285, 825-828; Shen, W. W. et al. (2001) *Biomacromolecules* 2:70-79). While membrane fluidity is critical for many of the functional responses of biological membranes, certain applications lend themselves to compromise in which a substantial increase in membrane stability may be achieved by in situ polymerization of the planar lipid assembly. The capacity to design surfaces with a high degree of molecular control over the assembly of diverse lipid and other membrane-associated constituents is retained. In this regard, applicants and colleagues have previously reported the in situ polymerization of phospholipids on self-assembled monolayers of octadecyl mercaptan bound to gold (Marra, K. G., et al. (1997) *Langmuir* 13: 5697-5701.), octadecyl trichlorosilane on glass (Marra, K. G., et al. (1997) *Macromolecules* 30:6483-6488; Orban, J. M. et al. (2000) *Macromolecules* 33:4205-4212.), and on an amphiphilic polymer cushion (Chon, I. H. et al. (1999) *J. Biomat. Sci. Polymer Ed.* 10:95-108).

Recently, polyelectrolyte multilayers (PEM) have been studied as bioinert films to reduce cell and protein adhesion (Elbert, D. L. et al. [1999*] Langmuir* 15:5355-5362) and as coatings to modulate interfacial molecular transport in drug delivery and immunoisolation systems (Moya, S. et al. [2000)] *Macromolecules* 33:4538-4544; Shi, X. and -Caruso, F. [2001*] Langmuir* 17:2036-2042). Other potential applications for these materials include their use as ultrafiltration membranes (van Ackern, F. et al. [998*] Thin Solid Films* 329:762-766) and in the assembly of optoelectronic devices (Cheung, J. H. et al. (1994) *Thin Solid Films* 244:985).

Membrane-mimetic systems have also had a direct impact on efforts aimed at understanding the mechanisms of blood coagulation at sites of vascular wall injury and on artificial surfaces. One of the most intriguing developments in the past decade has been the recognition that membrane mimetic systems having a phosphorylcholine component limit the induction of surface-associated blood clot formation. This biological property has been attributed to the large amount of surface bound water due to the zwitterion structure of the phosphorylcholine head group. It has also been suggested that specific plasma proteins which inhibit the blood clotting process are selectively adsorbed to this head group (Chapman [1993] Langmuir 9:39).

In a series of investigations using planar membrane models, Thompson and colleagues (Pearce et al. [1993] J. Biol. Chem. 268:22984-22991; and Tendian et al. [1991] Biochemistry 30:10991-10999) have characterized the molecular requirements for prothrombin binding to phospholipid membranes. It has been observed that the phosphorylcholine head group appears to limit the induction of blood clot formation on synthetic surfaces (Ishihara et al. [1994] J. Biomed. Mater. Res. 28:225-232; Hayward et al. [1984] Biomaterials 5:135-142; and Hall et al. [1989] Biomaterials 10[4]:219-224). It has been proposed that this biological property is related to the large amount of water bound to this zwitterionic head group, or conceivably, the selective adsorption to phosphorylcholine of specific plasma protein(s) that inhibit the blood clotting process (Chapman, D. [1993] Langmuir 9:39-45).

Several investigators have described the direct immobilization of thrombomodulin onto polymeric surfaces in order to generate thromboresistant materials for blood contacting applications. Kishida et al. (1994) Biomaterials 15(10):848-852; Kishida et al. (1994) Biomaterials 15(14):1170-1174; and Kishida et al. (1994) ASAIO Journal 40(3):M840-845 have conjugated TM to both aminated and carboxylated surfaces, including poly(vinyl amine) and poly(acrylic acid) surface-grafted polyethylene and a surface-hydrolyzed poly (ether urethaneurea). Vasilets et al. (1997) Biomaterials 18(17):1139-1145, have reported the immobilization of TM onto poly(acrylic acid) surface-grafted PORE. In all cases, the conjugation scheme utilized a carbodiimide based coupling reaction to link TM to the substrate via freely available amino or carboxyl functionalities on the protein surface. In vitro studies demonstrated that both clotting time and protein C activation were enhanced, and this activity appeared to be directly proportional to TM surface density, as determined by a ninhydrin assay. However, the ability to control TM surface concentration was substrate dependent, with reported TM densities ranging between 0.15 and 0.45 $\mu g/cm^2$, and TM bioactivity was significantly reduced after surface coupling, as evident by protein C activation rates which were increased only 5 to 10-fold as compared with an observed 20,000-fold enhancement when TM is evaluated as a component of either lipid vesicles or the endothelial cell surface. The loss of cofactor activity is believed attributable to the protein immobilization procedure, which is driven by random-site reactions to any accessible functional group on the TM surface, including those within the thrombin binding site. The impact of local flow conditions on the effectiveness of this strategy was not reported.

Although these studies confirm that substrate-bound thrombomodulin has the potential to limit thrombus formation on synthetic surfaces that are otherwise thrombogenic, the observed reduction in thrombomodulin bioactivity emphasizes that thrombomodulin's biological properties are intimately tied to a variety of structural features which can be lost upon direct covalent coupling to a biomaterial surface. For example, thrombomodulin's ability accelerate the thrombin-dependent activation of protein C requires three tandemly repeated EGF-like domains that serve as a thrombin binding site; a serine/threonine-rich 65 A spacer between the EFT-like domains and the transmembrane domain which optimally align thrombin's active site with the critical scissile bond in protein C; and a covalently associated chondroitin supine moiety that increases the affinity of thrombin binding to thrombomodulin by 10- to 20-fold and catalyzes ATIII inactivation of thrombin (Sadler, J. E. [1997] Thromb. Haemostasis 78[1]:392-395; and Esmon, C. T. [1995] FASEB Journal 9[10]:946-955). While some activity is retained even after the solubilization of thrombomodulin with detergents, membrane association significantly accelerates protein C activation by thrombomodulin. This is mediated, in part, by the ability of the membrane to locally concentrate and coordinate the approximate alignment of reacting cofactors and substrates with thrombomodulin (Galvin et al. [1987] J. Biol. Chem. 262[5]:2199-2205). For example, protein C has a C-terminal 4-carboxyglutamic acid (Gla) domain which binds to the cell membrane and presumably increases its local concentration by confining it to the two-dimensional plane of the lipid bilayer (Esmon et al. [1983] J. Biol. Chem. 258:[9]: 5548-5553; Mann et al. [1988] Ann. Rev. Biochemistry 57:915-956; Kalafatis et al. [1996] Critical Reviews in Eukaryotic Gene Expression 6[1]:87-101). In addition, the binding of protein C to the plasma membrane may also induce conformational changes that help align the protein C cleavage site with thrombin's proteolytically active domain. Both electrostatic and hydrophobic interactions may be involved in the association of protein C with the cell membrane. In this regard, recent studies suggest that protein C prefers to bind to and function on membranes that contain both phosphatidylcholine and phosphatidylethanolamine lipids. Protein C may also directly interact with fatty acid side chains within the membrane bilayer (Smirnov et al. [1999] Biochemistry 38[12]:3591-3598). It is surprising that the nature of the phospholipid headgroup may contribute to the subsequent catalytic and binding efficiency of activated protein C. For example, Smirnov et al. (1999 supra); and Smirnov et al. (1994) J. Biol. Chem. 269(2):816-819, have demonstrated that both the PE headgroup and phospholipid polyunsaturation contribute to factor Va inactivation by the activated protein C complex Thus, the lipid bilayer serves as an essential 'cofactor,' that in concert with thrombomodulin, accelerates protein C activation and subsequently optimizes APC anticoagulant activity.

Atherosclerosis remains a serious source of morbidity and death despite advances in preventive measures and pharmacological therapeutics. Nearly 700,000 vascular surgical procedures are performed annually in the United States along with several hundred thousand peripheral and coronary angioplasties (1). Prosthetic bypass grafts and, more recently, arterial stents and other endovascular prostheses have been utilized in association with these reconstructive procedures. Although large diameter vascular grafts (6 mm internal diameter) have been successfully developed from polymers such as polytetrafluoroethylene (PTFE) and polyethylene terephthalate, the fabrication of a durable small diameter prosthesis (<6 mm internal diameter) remains unsolved. Furthermore, while prosthetic bypass grafting performed in the infra inguinal position with reasonable short-term success, within 5 years 30% to 60% of these grafts will fail (Winger T. M. et al. (1996), "Lipopeptide conjugates: Biomolecular building blocks for receptor activating membrane-mimetic structures. Biomaterials 17:443-449). Likewise, restenosis and/or occlusion occur in as many as 50% of all patients within 6 months of stent placement depending upon the site and the extent of the disease (Winger T. M. et al. [(1997]), "Behavior of lipid-modified peptides in membrane-mimetic monolayers at the air/water interface," *Langmuir* 13:3256-3259).

It is recognized that the adverse events leading to the failure of many vascular prostheses are related to maladaptive biological reactions at the blood-material and tissue-material interface. In response to these problems, and particularly thrombosis of the small caliber prosthesis, grafts and stents have been coated with albumin, heparin, or prostacyclin analogues, which inhibit the clotting cascade and platelet reactivity, or with relatively inert materials, such as polyethylene oxide (Marra, K. G. et al. [(1997]), "In-Situ polymerization of phospholipids on an alkylated surface," *Macromolecules* 30:6483-6487). An alternate approach has been to design materials which support the in situ regeneration of an endothelial cell lining in order to create a functional arterial substitute with a durable thromboresistant interface (Marra, K. G. et al. [1997], "Stabilized phosphatidylcholine surfaces via in-situ polymerization at a solid-liquid interface," *Polymer Preprints* 38(2):682-683; Winger, T. M. and Chaikof, E. L. [1998] "Synthesis and characterization of supported bioactive lipid membranes. In: "Materials Science of the Cell," Eds. A. Plant and V. Vogel, MRS Publications, Pittsburgh, 1998.) However, strategies based upon the coating or derivation of a prosthetic surface with matrix proteins or integrin-selective peptide sequences that promote endothelial cell growth have been unable to overcome the capacity of these substrates to activate platelets and the coagulation cascade. Thus, in the period prior to complete endothelial regeneration, the surface of a small caliber prosthesis remains at increased risk for thrombus formation.

There is a need in the art for effective antithrombogenic treatments for blood-contacting implants and treatment devices.

Whole organ pancreatic allografts using current immunosuppressive protocols have an expected graft survival as high as 86% at one year and 74% at five years after transplantation. Despite these encouraging results, the risk of major perioperative morbidity, the associated complications of chronic immunosuppressive therapy and the persistent shortage of donor organ tissue remain significant limitations of this approach. As a consequence, in the 1990s pancreas transplantation continues to have a limited role in the management of diabetes. The utilization of xenogeneic organs should provide a solution to the chronic shortage of donor tissue. Nonetheless, the prevention of tissue rejection following cross-species transplantation remains unsolved. It has been postulated that cell based therapy, using xenogeneic islets or insulin producing cell lines in association with an immunoisolation barrier, provides a rational strategy to circumvent the vigorous humoral and cellular response of the host while increasing the supply of non-human donor tissue (Sun, Y. et al. [1996], "Normalization of diabetes in spontaneously diabetic cynomologus monkeys by xenografts of microencapsulated porcine islets without immunosuppression," *J. Clin. Invest.* 98:1417; Halle I., et al. [1993] "Protection of islets of Langerhans from antibodies by microencapsulation with alginate-poly-L-lysine membranes," *Transplantation,* 44:350-4; Colton, C. and Avgoustiniatos, E. [1991] "Bioengineering in the development of the hybrid artificial pancreas I" *Biochem. Eng.* 113:152-70; Colton, C. K. [1992], "The engineering of xenogeneic islet transplantation by immunoisolation," *Diab. Nutr. Metabol.* 5:145-9).

Cell based therapy, using xenogeneic islets or insulin-producing cell lines in association with an immunoisolation barrier is thus an important step in the successful treatment of insulin-dependent diabetes mellitus (DDM). A critical component of this approach is the maintenance of long-term graft survival by protecting or isolating donor cells from immunological processes in the recipient which lead to islet cell construction. Enhanced control of both transport properties and surface physiochemical characteristics is required for providing the effective immunoisolation barrier crucial to the success of pancreatic islet cell transplantation.

Current approaches for microencapsulation tailor transport properties by controlling the distribution of pore sizes generated by thermodynamically driven physical processes. Typically, semipermeable membranes for cell encapsulation can be formulated by one of three physical processes. The most common methodology is based upon the principle of phase inversion whereby polymer precipitation time, polymer-diluent compatibility, and diluent concentration influence phase separation, and as a consequence, membrane porosity (Crooks, C. A., Douglas, I. A, Broughton, R. L., Sefton, M. V., "Microencapsulation of mammalian cells in a HEMAMMA copolymer: Effects on capsule morphology and permeability," *J. Biomed. Mater. Res.* [1990] 24:1241-1262; Sefton, M. V. [1989], *Can. I. Chem. Eng.* 67:705; Uludag, H. and Sefton, M. V. [1993], "Metabolic activity and proliferation of CEO cells in hydroxymethyl methacrylate methyl methacrylate (KEA-M.A.)," *Cell Transplantation* 2:175-82; Roberts, I. et al. [1996], "Dopamine secretion by PC12 cells microencapsulated in a hydroxymethyl methacrylate-methyl methacrylate copolymer," *Biomaterials* 17:267-75). Using phase inversion techniques, the outer membrane surface morphology can range in pore size from nanometers to microns. As a second approach, barriers can be created by a polyelectrolyte coacervation reaction and molecular weight cutoff (MWCO) modulated by osmotic conditions, diluents, and the molecular weight distribution of the polycationic species (Matthew, H. W. et al [1993] "Complex coacervate microcapsules for mammalian cell culture and artificial organ development," *Biotechnol. Prog.* 9:510-519; Yoshioko, T. et al [1990], "Encapsulation of mammalian cell with chitosan-CMC capsule," *Biotechol. Bioeng.* 35:66-72; Dautzenberg, H. et al. [1996], *Polym. Sci.* 101:149). The utilization of multicomponent polycationic polymer blends and the diffusion time of oligocationic species through precast blends of polyanionic polymers have also been shown to be important variables in the control of MWCO when membranes are produced in this fashion. Alginate-calcium chloride systems represent a third technique for generating semipermeable capsules and have been used to produce monodisperse, spherical, transparent beads at a high production rate (Lim, F. and Sun, A. M. [1980], "Microencapsulated islets as a bioartificial endocrine pancreas, *Science* 210:908; King, G. A. et al [1987], "Alginate-polylysine microcapsules of controlled membrane molecular weight cutoff for mammalian cell culture engineering," *Biotech Progress* 3:231-240; Goosen, M. F. A. [1985], "Optimization of microencapsulation parameters: semipermeable microcapsules as a bioartificial pancreas, *Biotech Bioeng* 27:146-150). As a cell-compatible polysaccharide, alginate is an appealing polymer and, in addition, facilitates cryopreservation of the encapsulated cell (Rajotte, R. et al. [1995], "Adult islet cryopreservation. In: Ricordi, C., ed. "Methods in Cell Transplantation," Austin: R. Landes, 17-24). Control of transport properties, however, requires post-coating of the alginate with a poly(amino acid), typically, poly-L-lysine or a derivative thereof. In all of these strategies, membrane strength may be increased by altering the composition, structure, and dimensions of the membrane. This often has a secondary effect on diffusive transport. Therefore, in most systems, membrane strength and mass transport properties are interdependent membrane characteristics. It is also significant that the criteria for molecular exclusion is determined, in all of these systems, by the relatively broad distribution of pore sizes and/or dimensional characteristics of non-uniform pores. The inability to precisely control the transport characteristics of currently available encapsulation barriers has lead to their inevitable failure regardless of the chosen membrane formulation.

Recent data suggests that the rejection of pancreatic islet xenografts occurs by an immunological pathway which is distinct from that associated with either the autoimmune destruction of isogeneic islets or rejection of allogeneic grafts. In the latter two cases, islet damage appears to be mediated by a primary "Th1" immune response in which the dominant effector cell is a cytotoxic CD8 T cell (Peterson, I. D., and Haskins, K. [1996], "Transfer of diabetes in the NOD-scid mouse by CD4 T-cell clones: differential requirement for CD8 T-cells," *Diabetes* 45:328-36; Haskins, K. and McDuffe, M. [1990], "Acceleration of diabetes in young NOD mice with CD4+ islet-specific T cell clone," *Science* 249:1433-6; Jarpe, A. et al. [1990], "Flow cytometric enumeration of mononuclear cell populations infiltrating the islets of Langerhans in prediabetic NOD mice: Development of model of autoimmune insulinitis for Type I diabetes," *Regional Immunology* 3:305-17; Miller, B. et al. [1988], "Both the Lyt-2+ and L3T4+ T cell subsets are required for the transfer of diabetes in nonobese diabetic mice I" *Immunol.* 140:52-8). In contrast, the rejection of islet xenografts is characterized by a 'Th2' response in which CD4 helper T cells, but not CD8 cells, play a major role (Weber, C. et al. [1990], "Microencapsulated dog and rat islet xenografts into streptozotocin diabetic and NOD mice," *Horm. Metab. Res.* 35:219-226; Akita, K. et al. [1994], "Effect of FK506 and anti-CD4 therapy on fetal pig pancreas xenografts and host lymphoid cells in NOD/Lt, CBA, and BALB/c mice, *Cell Transplantation* 3:61-73; Gill, R. et al. [1994], "CD4+ T cells are both necessary and sufficient for islet xenograft rejection," *Transplantation Proceedings* 26:1203-4; Loudovaris, T. et al. (1992), "The role of T cells in the destruction of xenografts within cell impermeable membranes," *Transplantation Proceedings* 24:2938-9; Pierson, R. et al. [1989], "CD-4 positive lymphocytes play a dominant role in murine xenogeneic responses," *Transplantation Proceedings* 21:519-21; Parker, W. et al. [1996], "Transplantation of discordant xenografts: a challenge revisited," *Immunology Today* 17:373-8). That is, there is considerable evidence that xeno-recognition, unlike allorecognition or autoimmune destruction, primarily occurs via an "indirect" antigen presentation pathway in which host antigen presenting cells (APCs) display peptides scavenged from donor proteins to host helper T cells (Takeuchi, T. et al. [1992], "Heart allografts in murine systems," *Transplantation* 53:1281-94; Moses, R. et al. [1990], "Xenogeneic proliferation and lymphokine production are dependent upon CD4+ helper T cells and self antigen-presenting cells in the mouse. I," *Exp. Med.* 172:567-75; Lenschow, D. et al. [1992], "Long-term survival of xenogeneic pancreatic islet grafts induced by CTLA4Ig," *Science* 257:789-95). Presumably, xenogenic antigens are either released by the occasional broken capsule or diffuse across an intact capsule membrane after having been shed from the cell surface or liberated from necrotic or apoptotic cells. APCs process these antigenic cellular constituents and activate CD4+ T cells which develop into Th2 cells. In turn, Th2 cells stimulate the matron of B cells, which uniquely express the processed foreign peptide, into plasma cells that secrete xenoantigen specific antibodies. Investigators now suspect that it is the generation of immune complexes either by the binding of newly-formed antibodies to xenoantigens or preexisting autoantibodies to islet antigens that leads to inevitable islet cell destruction even in the presence of a barrier which directly excludes their entry. (Weber, C. I. et al. [1998], "Long-term survival of poly-L-lysine-alginate microencapsulated rat, rabbit, and pig islet xenografts in spontaneously diabetic NOD mice," In: Lanza R, Chick, W., ed. "Handbook of Cell Encapsulation Technology and Therapeutics" [New York: Springer-Verlag]). Antigen-antibody complexes efficiently bind to Fc receptors expressed on the surface of macrophages which leads to their activation and the subsequent secretion of a variety of low molecular weight cytotoxic mediators including cytokines and free radicals, such as interleukin-1 and nitric oxide, respectively (Ke, Y. et al. [1995], "Ovalbumin injected with complete Freund's adjuvant stimulates cytolytic responses," *Eur. J. Immunol.* 1995:549-53). It is also likely that activation of the complement cascade by generated antigen-antibody complexes is a significant factor in potentiating islet destruction (Müller-Eberhard, H. I. [1988], "Molecular organization and function of the complement system," *Ann Rev Biochem* 57:321-47). The production and association of C3b with circulating immune complexes could enhance the binding of these complexes to macrophages via the cell surface C3b receptor (Krych, M. et al. [1992], Complement receptors," *Curr. Opin. Immunol.* 4:8-13). In addition, concomitant release of C3a induces a local neutrophil response with the release of soluble factors, thereby, further potentiating the activation and recruitment of macrophages (Frank, M. [1991], "The role of complement in inflammation and phagocytosis," *Immunol. Today* 12:322-6). Notably, at the time of islet rejection an intense pericapsular cellular response is observed which is dominated by the presence of macrophages and B cells (Weber, C. et al. [1994], "NOD mouse peritoneal cellular response to poly-L-lysine-alginate microencapsulated rat islets," *Transplantation Proceedings* 26: 1116-1119; Weber, C. I. et al. [1990], "The role of CD4+ helper T cells in destruction of microencapsulated islet xenografts in NOD mice," *Transplantation* 49:396-404).

Prior work by inventors hereof includes U.S. patent application Ser. No. 09/149,098 filed Sep. 8, 1998, provisional application No. 60/058,194 filed Sep. 8, 1997, provisional application Nos. 60/091,399 and 60/101,252 filed Jun. 30, 1998 and Sep. 21, 1998, respectively, provisional application No. 60/197,072 filed Apr. 13, 2000, provisional application 60/221,618 filed Jul. 28, 2000, provisional application No. 60/198,792 filed Apr. 20, 2000 and 60/221,828 filed Jul. 28, 2000, PCT application US01/12094 filed Apr. 13, 2001, and PCT application No. US01/12918 filed Apr. 20, 2001, PCT application 97/16080 filed Apr. 11, 1997, application Ser. No. 08/729,928 filed Oct. 15, 1996, Ser. No. 09/342,922 filed Jun. 30, 1999, Ser. No. 09/149,098 filed Sep. 8, 1998, U.S. Pat. No. 6,171,614 issued Jan. 9, 2001, U.S. Pat. No. 6,071,532 issued Jun. 6, 2000, U.S. Pat. No. 5,741,325 issued Apr. 21, 1998, and U.S. Pat. No. 4,906,465 issued Mar. 6, 1990.

All publications referred to herein are incorporated by reference to the extent not inconsistent herewith.

SUMMARY OF THE INVENTION

The present invention provides a biocompatible biomaterial (or biological component) comprising a membrane-mimetic surface (also referred to herein as a membrane-mimetic film) covering a substrate. In a preferred embodiment, the substrate is a hydrated substrate such as a hydrogel. The hydrated substrate may contain drugs for delivery to a patient through the membrane-mimetic film or may be made up of cells, such as islet cells for transplantation. The surface may have bioactive molecules or moieties exposed thereon for binding to target molecules in vivo, for modulating host response when implanted into a patient, e.g. the surface may be antithrombogenic or anti-inflammatory, and the surface may have pores of selected sizes to facilitate transport of substances therethrough. There may be an optional hydrophilic cushion or spacer between the substrate and the membrane-mimetic surface so that transmembrane proteins may extend from the surface through the hydrophilic cushion, mimicking the structure of cells which are naturally equipped with transmembrane proteins. The biological component of this invention preferably provides an alkylated layer directly beneath the membrane-mimetic surface to facilitate bonding of the sure. Alkyl chains may extend entirely through the hydrophilic cushion when present. The substrate may optionally be treated with a polyelectrolyte or alternating layers of oppositely-charged polyelectrolytes to facilitate charged binding of the membrane-mimetic film or alkylated layer beneath the membrane-mimetic film to the substrate.

In one embodiment, this invention provides a biological component comprising a hydrated substrate coated with a stable, alkylated surface by the steps of: complexing a polyelectrolyte onto the hydrated substrate, and coating the surface of the polyelectrolyte with an oppositely charged amphiphilic polymer containing long-chain alkanes. Preferably, thereafter, a membrane-mimetic spice is formed on the alkylated surface. The portion of the biological component overlying the substrate is referred to herein as an "artificial membrane."

The polyelectrolyte may be coated or complexed on to the hydrated substrate, followed by coating of an oppositely charged polyelectrolyte. Several alternating layers of oppositely-charged polyelectrolytes may be built up in this way.

The term "biological component" refers to a manufactured object of this invention designed for medical use as a prosthetic implant, artificial organ or tissue, drug delivery device, or other object designed for placement into a human or animal body or an in vivo treatment device in contact with living cells, tissues, or organs of a patient.

The term "hydrated substrate" refers to a substance such as a hydrogel having a high moisture content and a hydrophilic surface. The hydrated substrate may comprise a natural or synthetic collagen, gelatin, alginate, chitosan, polyhema, hydroxyethylmethacrylate, polyacrylamide, recombinant collagen protein, protein-mimetic polypeptide polymer, cell, tissue, organ, microorganism, or polysaccharide or protein carrying a charge and capable of complexing with the polyelectrolytes of this invention. The hydrated substrate may also consist of another material such as metal or plastic coated with a hydrated layer. Any hydrated material known to the art for insertion into a human or animal body may be used in this invention. In a preferred embodiment, alginate microbeads or cells encased in the artificial membrane of this invention. The hydrated substrates of this invention are capable of attaching to the substrate by charge-charge bonding, as to a polyelectrolyte-coated substrate, or by covalent bonding when the substrate inherently provides, or has been treated to provide, sites for covalent bonding.

In a preferred embodiment, the substrate comprises cells to be implanted into the host. Such cells include islet cells, hepatocytes, parathyroid cells, thyroid cells, neurons, sertoli cells and genetically-engineered cells designed to secrete bioactive compounds, e.g. for the treatment of disorders such as neurodegenerative, endocrine deficiency, autoimmune, inflammatory, and malignant conditions.

The term "coated" with respect to the polyelectrolyte coating the hydrated substance, means that at least a portion of the surface of said substrate is overlaid with polyelectrolyte, such that said polyelectrolyte is attached to said surface by ionic or covalent bonds The term "stable" with respect to the alkylated surface means able to withstand shear forces encountered in use. In a preferred embodiment, the term "stable with respect to the membrane-mimetic spice means requiring a force greater than that typically required to remove bound antigens from monoclonal antibodies, preferably at least about 26 kT, and more preferably able to withstand shear forces of at least about a wall shear rate of 2000 sec-$^1$.

"Amphiphilic polymers" useful in this invention include any polymer which can be attached via ionic or covalent bonding to both a hydrophilic underlayer and a lipophilic outer membrane-mimetic layer.

Preferred amphiphilic polymers include diallyl-containing polymers which comprise a component containing alkyl groups and a component providing a hydrophilic cushion. The amphiphilic polymer may also contain a component providing stable attachment to the substrate. A preferred terpolymer is 2-hydroxymethyl acrylate (HEA) and 2-(methylthio) ethyl methacrylate (MTEM), with a third monomer, 3-acryloyl-3-oxapropyl-3-(N,N-dioctadecylcarbamoyl)-propionate (AOD), at a statistical composition of 6:3:1 HEA: AOD:MTEM The sulfur-containing monomer binds to the substrate as an anchor, whereas the hydrophobic monomer AOD migrates to the surface, exposing an ordered layer of alkyl chains for vesicle fusion. The hydrophilic HEA component acts as a "cushion" which facilitates the self-assembly of the alkylated chains at the solid-aqueous interface. Fusion of the lipid vesicles may then be executed by means known to the art, such as that of Plant (1993) Langmuir 9:2764; Lamparski at al. (1993) *J. Am. Chem. Soc.* 115:8096, etc. In another embodiment, the terpolymer comprises 2-hydroxymethyl acrylate (HEA), 3-acryloyl-3-oxapropyl-3-(N,N-dioctadecylcarbamoyl)-propionate (AOD), and styrene sulfonate in a molar ratio of 6:3:1. Copolymers of HEA and AOD without an anchoring component are also useful for casting onto a hydrogel substrate, preferably at a 1:1 ratio. When the copolymer is used with an alginate or other hydrogel substrate, the polyelectrolyte may be dispensed with.

An "alkylated surface" is one in which alkyl chains (with or without substituents) are covalently or ionically bonded to said surface. The alkylated surface may comprise charged substituents to facilitate ionic or covalent bonding of further elements of the biological component of this invention, such as the membrane-mimetic surface and/or any biologically active moieties associated therewith. Alternatively, or in addition, the alkylated surface may present a spaghetti-like mass in which surface components or moieties may be entangled.

The term "long-chain" refers to alkyl or acyl chains having at least about 6 or at least about 8 carbons, more preferably about 14 to about 24, and most preferably about 16 to about 22. The terms "alkylation," "alkylated," and "alkyl chains" include the use of acyl and other substituted alkyl chains. Such chains may be straight or branched, and may contain additional substituents such as those containing halogen, amino, oxygen, sulfur, phosphorus and others common to compounds found in human or animal cells and tissue.

The term "polyelectrolyte" means a positively or negatively charged polymeric substance such as alginate which is negatively charged or poly-L-lysine which is positively charged.

A "membrane-mimetic surface" of this invention is the outer layer of an artificial membrane of this invention.

An "artificial membrane" of this invention may be a lipid surface, preferably a phospholipid surface, covering a substrate. Preferably the artificial membrane comprises a membrane-mimetic surface overlying an amphiphilic polymer presenting an alkylated surface to facilitate attachment of the outer lipid surface.

The term "membrane-mimetic" with respect to an artificial membrane or surface means that the artificial membrane or surface has at least one property enabling said membrane or surface to modulate interactions between a cell, tissue, blood, organ or other living material and said membrane, surface, or a substrate on which said membrane or surface has been placed. Such modulations include reduction of thrombogenicity, reduction of inflammatory response, selective transport of molecules such as drugs, sequestering of particles from the host into which the membrane-mimetic surface has been placed by receptor-like moieties on, in or attached to the surface, and other modulatory effects of naturally-occurring membranes.

Membrane-mimetic surfaces of this invention may be formed of lipids, preferably phospholipids. Preferred phospholipids are phosphatidylcholine, phosphatidylethanolamine, phosphatidylglycerol, a boloamphiphile such as single-chain ester or ether-linked phospholipids, double-chain ester or ether-linked phospholipids, cyclic ester or ether-linked phospholipids, for example, ether-based phospholipids such as dialkyl (C10-C20), ether-linked phospholipids, mono or dialkenyl (C10-C20) ether-linked phospholipids, such as phosphatidylcoline, phosphatidyl ethanolamine, phosphatidic acid, lipopeptide conjugates such as those described in International Patent Published Application WO 00/000239 and U.S. Pat. No. 6,171,614, synthetic, recombinant, or native peptides conjugated to a lipid group, where peptides are selected on the basis of their biological activity; for example, cell adhesion sites, anti-thrombotic or anti-inflammatory characteristics, glycolipid conjugates such as synthetic or native oligosaccharides, polysaccharides, glycosaminegly-cans, including derivatives of heparan sulfate, chondroitin sulfate, dermatan sulfate, keratan sulfate, and hyaluronan conjugated to a lipid group, where the glyco-group is selected on the basis of its biological activity, for example, cell adhesion sites, anti-thrombotic or anti-inflammatory characteristics. The term "phospholipid" includes phospholipids derivatized to comprise polymerizable moieties, preferably only one polymerizable moiety per phospholipid molecule, and/or derivatized with alkylamino groups such as choline or ethanolamine.

Suitable polymerizable moieties for derivatizing the phospholipid are acryloyloxy, methacryloyl, dienoyl, sorbyl, styryl, acrylamide, acrylonitrile, N-vinyl pyrrolidone.

Preferred phospholipids are phosphatidylcholine phospholipids.

In one embodiment the phospholipid has the structure (I):

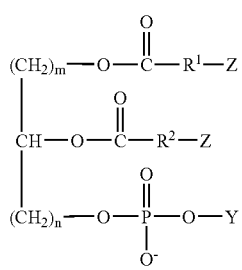

wherein
$R^1$ is a ($C_1$-$C_{30}$) alkyl group;
$R^2$ is a ($C_1$-$C_{30}$) alkyl group;
m is 1-4;
n is 1-4;
Y is an alkylamino group; and
Z is —H or a polymerizable monomeric group such that if $R^1$ is attached to Z=—H, then $R^2$ is attached to Z=a polymerizable monomeric group, and if $R^1$ is attached to Z=a polymerizable monomeric group, then $R^2$ is attached to Z=—H.

More preferably, the biocompatible biomaterial has the structure (I) wherein $R^1$ is a ($C_{12}$-$C_{30}$) alkyl group; $R^2$ is a ($C_8$-$C_{14}$) alkyl group; m is 1 and n is 1. In a preferred exemplification, the biocompatible material is 1-palmitoyl-2[12-(acryloyloxy)dodecanoyl]-sn-glycero-3-phosphorylcholine. The acrylate groups of the lipid molecules polymerize, forming a surface network in a two-dimensional plane.

The phospholipid may also comprise a mire of polymerizable phospholipids and non-polymerizable phospholipids so that non-polymerized domains are generated for optimization of thrombomodulin activity or optimization of activity of membrane-bound receptors whose activity is dependent on their capacity or the capacity of its substrate or cofactors to move and/or assemble within the membrane-mimetic film.

Preferably, the membrane-mimetic surface is formed by synthesis of unilamellar vesicles therefrom by extrusion through a porous membrane. The vesicles are then fused onto a surface alkylated with long chains, and polymerization is carried out in situ, e.g. by photopolymerization, and/or with a polymerization initiator known to the art.

The membrane-mimetic surface may be covalently linked with the underlying alkylated surface, such as by crosslinking of the lipid molecules to functionalities such as amine or acyl groups on the alkyl chains extending from the underlying surface.

The membrane-mimetic spice may also be non-covalently linked to the underlying alkylated surface, such as by ionic bonding or entanglement of alkyl chains on the lipid molecules with alkyl chains extending from the underlying surface.

The following table shows some preferred types of linkages between the lipid and underlying alkylated surface:

| Table of Supported Lipid Bilayer | | |
|---|---|---|
| Lipid | Alkylated Surface | Interaction |
| alkyl | alkyl | noncovalent: hydrophobic |
| polymeric alkyl | alkyl | noncovalent: hydrophobic |
| alkyl amine | alkyl amine | covalent: acylation |
| alkyl active ester | alkyl amine | covalent: acylation |
| alkyl acrylate | alkyl amine | covalent: Michael addition |

The membrane-mimetic surface of this invention preferably comprises two levels of attachment or cross reaction, i.e., (a) within the plane of phospholipid molecules, e.g., linking together of different phospholipid alkyl chains, and (b) between planes, e.g., interdigitating chains between phospholipid monolayers and the substrate surface.

Alternatively, the membrane-mimetic surface may be formed of a synthetic self-assembling amphiphile which comprises a boloamphiphile having phospholipid head groups on top and at the bottom, separated by alkyl chains, which allows the surface including a hydrophilic cushion to be formed without in situ polymerization of vesicles.

The membrane-mimetic surface may be formed to comprise pores of a selected size in order to permit transport of molecules below a selected size. For example, in one embodiment, molecules having a molecular weight greater than about 70 kD were unable to pass through the surface. Preferred size ranges are: about 20 to 50 Å, 50 to 100 Å, 20 to 50 Å and 100 to 250 Å, plus or minus about ten percent.

The pores may be formed by means known to the art. In preferred embodiments, the pores are formed by templating the membrane with polymerizable host particles by means known to the art whereby such particles may leach out of the membrane after formation thereof or may be retained within the membrane to function as sieve-like inserts. Such particles may be selected from the group consisting of albumin, nanospheres and dendrimers of a selected size and shape, such as polyethylene oxide, polyacrylamide, poly(hydroxymethyl acrylate) (poly(HEA)), poly(hydroxymethyl methacrylate) (poly(HEMA)), poly(vinylpyrollidone), polyacrylic acid, polystyrene and block copolymers thereof. Preferably each arm of the dendrimer is terminated with a moiety which can be crosslinked (covalently linked) or non-covalently linked to a portion of the biological component of this invention, preferably to the membrane-mimetic surface (i.e. to the lipid molecule) or to the substrate.

Bioactive molecules comprising various functional groups (e.g., lipid, peptide, sugar, etc.) may be incorporated into or appended to the substrate on which the membrane-mimetic surface is polymerized, thereby contributing new or specified biochemical characteristics to the polymerized surface. By first attaching a desired modular unit to a substrate (e.g., a polymer or a metal or derivatives thereof) and then carrying out in situ polymerization, the invention overcomes the disadvantages of unstable, non-permanent systems while providing the desired specificity of surface properties and biofunctionality in membrane-mimetic systems.

The term "bioactive molecule" as used herein includes the plural (bioactive molecules) and truncated molecules comprising active portions thereof and refers to any molecule or portion thereof which has a measurable effect on a living organism, e.g. enhancing viability or function, or minimizing pathological conditions.

The term "bioactive substance" as used herein, includes drugs for administration to a patient to correct a pathogenic condition.

Devices for implantation into a patient include any type of prosthesis, artificial organ, cell, drug delivery device, or therapeutic device. Such devices include, without limitation, dialysis tubing, dialysis membranes, hollow fibers, membrane oxygenators, artificial blood vessels, artificial heart valves, left ventricular assist devices, artificial hearts, artificial lungs, artificial kidneys, artificial livers, vascular grafts, artificial heart valves, artificial joints, catheters, synthetic and intraocular lenses, electrodes, artificial cartilage, ligaments, tendons, bones and bone grafts, tissue reinforcements, tissue scaffolds including tissue scaffolds comprising cells and/or tissues, cell-containing capsules, intraluminal stents for use within blood vessels, biliary system or other hollow organs. Such devices may be constructed of or coated with polymers, glass, metal, or any substance known to the art, and may be porous or non-porous.

Hydrated substrates of this invention may also be incorporated into openings in implanted devices, to fill such openings or coat inner surfaces of tubes, conduits and the like. Preferred conduits of the present invention include porous expanded polytetrafluoroethylene (ePTFE), or Dacron prosthesis impregnated with gelatin or alginate, followed by sequential coating with alginate and poly-L-lysine. However, the conduit can be made of any synthetic polymer (PTFE, polyethylene terephthalate (PET), polyester urethane (PEU) or appropriately processed native biomacromolecules (such as collagen or polysaccharides). Methods for making such devices are described in PCT application PCT/US01/12094 filed Apr. 13, 2001, incorporated herein by reference to the extent not inconsistent herewith.

The term "biocompatible" as used with respect to a biological component of this invention means that the component does not trigger inflammatory reactions after implantation in or contact with human or animal tissue and/or does not provide a surface which is prone to thromboses.

The membrane-mimetic surface may be formed to be antithrombogenic. For example, phospholipid head groups have when assembled on the membrane-mimetic surfaces of this invention have antithrombogenic properties. Further the membrane-mimetic surface may incorporate an antithrombogenic moiety into the surface as described hereinafter. The antithrombogenic moiety may be comprised in any antithrombogenic molecule known to the art, including antithrombotic, antiplatelet, and profibrinolytic agents. The antithrombogenic moiety may be selected from the group consisting of thrombomodulin, endothelial cell protein C receptor, vascular ATP diphosphohydrolase, albumin, heparin, prostacyclin, hirudin, lysine, and analogs thereof and other antithrombogenic moieties known to the art. The protein fragment can be coupled to a lipid or other membrane-inserting hydrophobic group either before the formation a polymerized membrane-mimetic surface (i.e., to be inserted with other membrane components during the formation of the membrane-mimetic surface) or coupled to a lipid or other membrane-bound group after the formation of the membrane-mimetic surface (i.e., to further functionalize the formed surface). Preferably it is added to the phospholipid prior to polymerization in situ, and the polymerization is conducted in such a way as not to destroy the biological activity of the antithrombogenic molecule as described in the Examples hereof. A lipid thrombomodulin mutant may be used such as thrombomodulin fragment generated enzymatically, synthetically, or by recombinant methods, that contains any or all of the extracellular domain which includes EGF repeats 4-6. (Sadler, J. E. [1997] *Thromb. Haemostasis* 78[1]: 392-395; and Esmon, C. T. [1995] *FASEB Journal* 9[10]:946-955.) Such lipid-modified thrombomodulins may be prepared by expressing an extracytoplasmic domain of the thrombomodulin molecule in a suitable host.

The amount of antithrombogenic moiety to be used is sufficient to cause a measure antithrombogenic response compared with implants not comprising the membrane-mimetic surface of this invention. Preferably the amount of surface coverage of the membrane-mimetic surface is between about 10 and about 100%.

The presence of at least one of a phosphatidylethanolamine and a phosphatidylcholine group on the artificial surface significantly improves the biological activity of thrombomodulin or a truncated thrombomodulin derivative in terms of minimizing thrombogenesis via activation of the endogenous protein C activation anticoagulant pathway, and similarly, improves biocompatibility for the implanted medical materials.

The membrane-mimetic surface may be formed to be anti-inflammatory, e.g. for use in avoiding host rejection of implanted materials such as polymers and artificial tissues, cells and organs. An anti-inflammatory moiety such as thrombomodulin, endothelial cell protein C receptor, vascular ATP diphosphohydrolase, hirudin, annexin, or HLA-G, IL-10, hyaluronan, heparan sulfate, heparin, chondroitin sulfate, keratan sulfate, dermatan sulfate or anti-inflammatory analogs and derivatives thereof may be incorporated into the membrane. Natural glycosaminoglycan such as heparin, heparan sulfate, chondroitin sulfate, dermatan sulfate, keratan sulfate and hyaluronan may be used to form an anti-inflammatory neoglycocalyx on the membrane-mimetic surface.

The amount of anti-inflammatory moiety to be used is sufficient to cause a measurable anti-inflammatory response compared with implants not comprising the membrane-mimetic surface of this invention. Preferably the amount of surface coverage of the membrane-mimetic surface is between about 10 and about 100%.

The biological component of this invention may also have a targeting moiety linked thereto for the purpose of binding to particles in the host into which the biological component has been implanted. Useful targeting moieties are known to the art and include biotin, maleimide, maleimidocaproyl (EMC), carbohydrate and ligands for various antibodies and proteins. The particles to be attracted include avidin, streptavidin, thiol-containing proteins, polypeptides, peptides, polysaccharides, lectin, enzymes, and antibodies. The following table indicates preferred lipid linkers, moieties which may be incorporated or attached to the membrane-mimetic surface, and the type of bonding involved:

| Table of Targeting Linkers | | |
| --- | --- | --- |
| Lipid linker (on membrane) | Particle Targeted | Interaction |
| biotin | avidin, streptavidin | noncovalent: hydrogen bond |
| maleimide | thiol-containing proteins, | covalent: thioester |
| maleimidocaproyl (EMC) | polypeptides, peptides, polsaccharides | |
| carbohydrate | lectin, enzymes | noncovalent: hydrogen bond |
| ligand | antibody, proteins | noncovalent |

The term "patient" means a human or animal, preferably a mammal.

The biological components of this invention may be used for drug delivery by incorporating a drug therein. The drug may be incorporated into the membrane-mimetic surface, or into any underlying portions of the biological component, such as a hydrated substrate.

In a preferred embodiment, the present invention provides a biomaterial comprising as part of a membrane mimetic surface a phospholipid or phospholipid derivative with a polymerizable monomeric group, i.e. a single polymerizable group (e.g., acryloyloxy, methacryloyl, dienoyl, sorbyl, styryl, acrylamide, acrylonitrile, N-vinyl pyrrolidone, mono or bis acrylates (acryloyl, methacryloyl and sorbyl), mono or bis-dienes, mono or bis-diacetylene, mono or bis-styryl groups, mono or bis-thiols, mono or bis-disulfides, etc.). Useful moieties are depicted below:

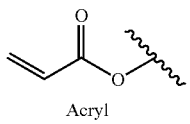
Acryl

Sorbyl

-continued

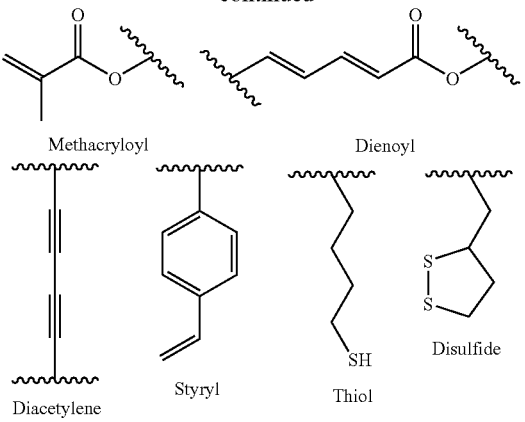

Such biomaterial phospholipid molecules form self-assembled monolayers that attach or absorb (e.g., through hydrophobic interactions, etc.) to a substrate whereon the polymerizable monomeric groups of the biomaterial phospholipid moieties are photopolymerized in situ. The biomaterial of the invention comprises at least two levels of attachment or cross reaction, i.e., within the plane of phospholipid molecules, e.g., linking together of different phospholipid alkyl chains, and between planes, e.g., interdigitating chains between phospholipid monolayers and the substrate surface. The vesicle fusion and photopolymerization conditions provided herein are less harsh than polymerization conditions previously used, thus mediating less inactivation of biologically active molecules, e.g. thrombomodulin.

The artificial cell membrane of this invention provides an immunoisolation barrier with improved performance characteristics because of its capacity to control interfacial transport by the presence of channels, transporters, and pores, as well as through its ability to act as a template for more complex composite structures with other immunoregulatory macromolecules. In a preferred embodiment of this invention, a membrane-mimetic glycocalyx is provided comprised of a stable, lipid membrane-like bilayer supported on a hydrated islet encapsulating alginate substrate. Transport properties are tailored by the insertion of poly(ethylene oxide) dendritic polymers, to create artificial molecular pores and channels, and maladaptive inflammatory responses are modulated by the incorporation of glycosaminoglycan (GAG) neoglycolipids, as a barrier to complement activation and macrophage adhesion. Heparin and chondroitin sulfate are used as pendent groups on the polymerizable phospholipid macromolecules to minimize adhesion. As an illustration of this invention, porcine islets are encapsulated as described herein. The donor pancreatic islet grafts show good survivability, capsule stability biocompatibility, and euglycemia is maintained.

The artificial cell membranes of this invention have enhanced surface and mass transport properties. Such microencapsulated pancreatic islet xenografts are an effective strategy for restoring euglycemia in the treatment of insulin-dependent diabetes mellitus. Glycosaminoglycan neoglycolipids and well-defined molecular pores, as components of a membrane-mimetic barrier, protect encapsulated islets from adverse host immune responses.

DETAILED DESCRIPTION OF THE INVENTION

Figure 1:
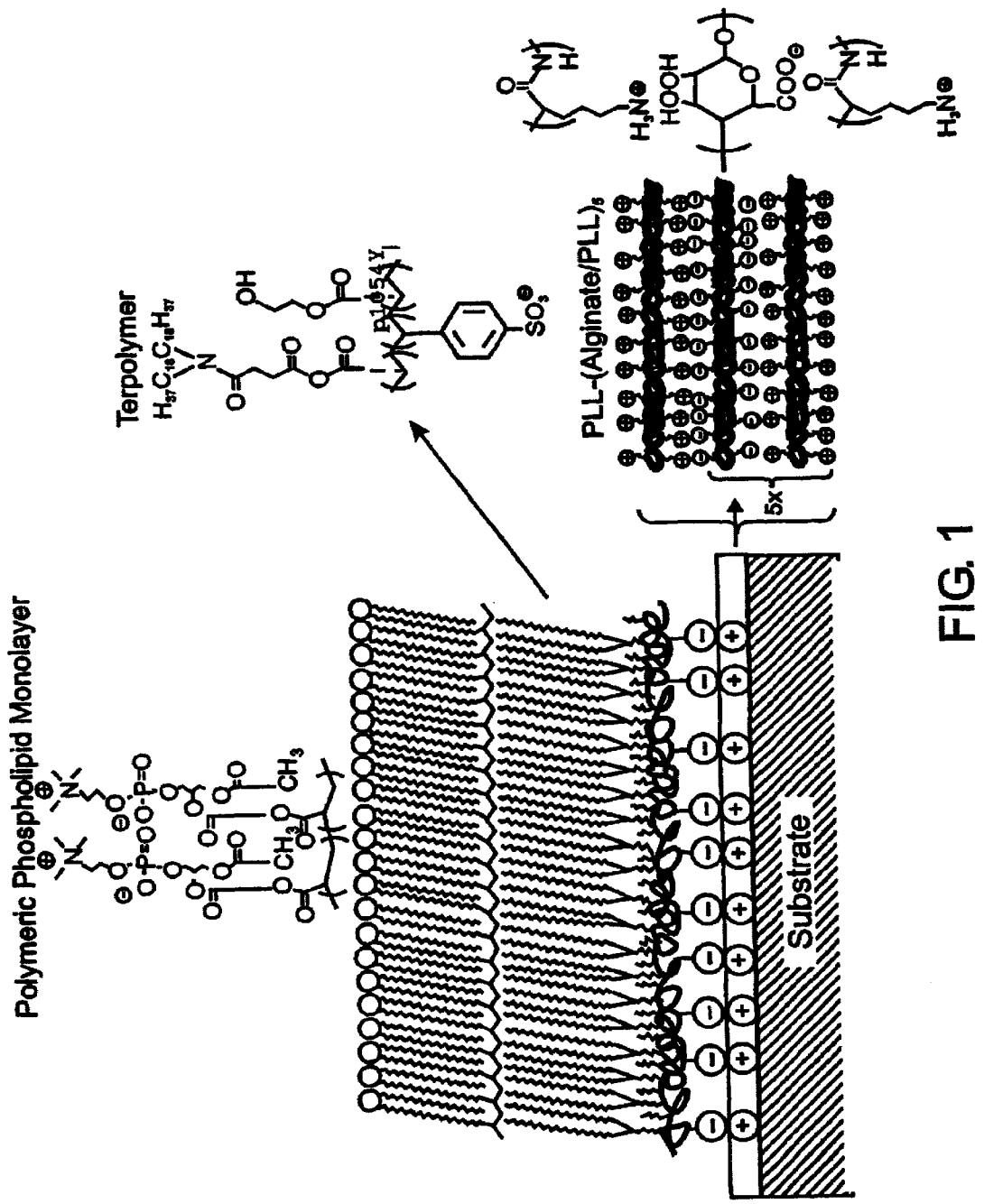
FIG. 1 depicts a polymeric phospholipid monolayer supported by a polyelectrolyte multilayer.

In a preferred embodiment, an artificial membrane comprising an amphiphilic polymer with anionic anchoring groups providing a convenient means for surface alkylation with an intervening polymer cushion is provided. Following the formation of a surface-supported assembly of mono-acrylated lipids, photoinitiated polymerization is performed to stabilize the membrane. This artificial membrane is stable in a high shear rate environment, and can modulate interfacial molecular transport. In addition, the system can be used as a cell encapsulation barrier as described in the Examples hereof.

This invention also provides methods for enhancing the clinical durability of small diameter vascular grafts by limiting thrombus formation and restenosis by local activation of the endogenous protein C anticoagulant pathway. The incorporation of thrombomodulin into a membrane-mimetic assembly of this invention generates an actively antithrombogenic arterial bioprosthesis based upon a physiologically dominant anticoagulant mechanism. The invention was made possible by identifying and incorporating into the artificial membrane system of this invention actively antithrombogenic mechanisms that are operative at the blood-material interface under a range of hemodynamic conditions. For example, a membrane-mimetic assembly that contains thrombomodulin (TM) as an activator of the endogenous protein C anticoagulant pathway is especially useful for this purpose.

The natural cell membrane establishes an important paradigm for the design of an antithrombogenic surface because of its capacity to participate in molecular recognition processes that are physiologically relevant to the control of blood coagulation. Thrombomodulin, as a transmembrane protein formed on the luminal surface of endothelial and smooth muscle cells, is a critical regulator of the protein C pathway and represents the major anticoagulant mechanism that is operative in both normal and injured blood vessels. Significantly, its catalytic efficiency is directly related to its localization within a lipid bilayer. Membrane-mimetic assemblies are provided herein comprising TM integrated into stable, substrate-supported, lipid membrane-like bilayers. These biomimetic materials can activate protein C and regulate the initiation and propagation of coagulation processes under arterial and venous flow conditions in vitro and in vivo.

Specifically, a membrane-mimetic thin film incorporating thrombomodulin as a mediator of an "on-demand" anticoagulant response is provided, and the role of the hemodynamic flow regime in modulating protein C activation and thrombin generation is defined using these membrane-mimetic systems. Thrombomodulin integrated into a membrane-mimetic interface influences both thrombus formation and the development of anastomotic neointimal hyperplasia in vivo.

Small diameter vascular prostheses can be functionalized with TM-containing membrane-mimetic components to form biostable surfaces resistant to platelet and fibrinogen deposit.

Both cell-cell and cell-matrix interactions regulate endothelial regeneration. Biological regulators of endothelial regeneration in vivo serve as a staring point for tissue engineering in which bioprosthesis design is based upon a composite structure composed, in part, of biomimetic materials. Endothelial cells repair denudation injuries by migrating over a complex substrate composed of smooth muscle cell plasma membranes and secreted and/or adsorbed glycoproteins and proteoglycans. Within this environment, intercellular communication is mediated both by a bi-directional exchange of soluble factors and by direct contact mediated interactions. E.g., a smooth muscle cell-surface specialization of particular significance to the process of endothelial migration is the fibronexus; the commonest variant of which has been described as tracklike and is characterized by extracellular fibronectin filaments which diverge from the cell surface and contact other cells or matrix constituents. Fibronectin is secreted by cells as a dimer, may be lipid-modified, and is composed of three types of modular protein units, which are organized into unique functional domains. These domains include binding sites for endothelial cell-surface receptors such as the integrins. Therefore, upregulation of fibronectin synthesis following vascular wall injury yields increased numbers of cell binding sites which act as anchors for cell locomotion during the process of endothelial regeneration. Similarly, a second important regulator of endothelial repair processes are heparan sulfate (HS) proteoglycans, which lie abundantly on the surface of vascular smooth muscle cells and are secreted into the pericellular matrix. Their expression is up-regulated following de-endothelialization injuries; particularly, perlecan in the surrounding matrix and syndecans 1 and 4 on the cell surface. Heparan sulfates influence endothelial motility by acting as a local storage and delivery depot for heparan-binding cytokines. Thus, fibronectin and heparan sulfates, either alone or as a component of a more complex plasma membrane assembly, serve as important adaptive responses for vascular wall healing. Thus, this invention provides arterial bioprostheses based upon a composite structure consisting of membrane- and glycosaminoglycan (GAG)-mimetic components which is sufficiently robust for medical implant applications. The incorporation of appropriate peptide species into these assemblies facilitates in vivo endothelialization.

A number of membrane-based physiological processes are also useful for maintaining a nonthrombogenic environment above and beyond the lipid constituents of the membrane itself. Despite the partial loss of an endothelial lining, intimal repair processes often occur in the absence of overt vessel thrombosis due to physiological responses, which efficiently modulate the coagulation cascade and platelet activation. Admittedly, the release of nitric oxide and prostacycin by the vessel wall limits platelet activation and aggregation. However, the inhibition of blood coagulation is primarily achieved by two alternate mechanisms: serine proteinase inhibitors, also known as "serpins", which act by the formation of stable 1:1 molar complexes with their target enzymes and the protein C pathway that leads to inactivation of coagulation factors Va and VIIIa. Antithrombin III (ATIII) and tissue factor pathway inhibitor are both examples of serpins that inhibit thrombus formation. Sepin-mediated anticoagulation processes are largely confined to the surface of endothelial and smooth muscle cells due to their ability to bid to sulfated glycoasminoglycans, particularly heparan sulfate. Moreover, heparan sulfates on the smooth muscle cell sure, in the ECM, or on neighboring uninjured endothelium actively accelerate these proteinase inhibition reactions. To date, the catalysis of the ATIII-thrombin reaction by heparan sulfate has been the most thoroughly characterized. However, despite the presence of serpin binding sites on heparan sulfates and the well characterized anticoagulant properties of these glycosaminoglycans, the physiological significance of the anticoagulant/antithrombotic functions attributed to heparan sulfates at the vascular cell surface have not been conclusively established. For example, high affinity ATIII binding sites have not been localized to heparan sulfates that are in direct contact with blood. Moreover, the alleged catalytic effect of heparan sulfate on the ATIII-thrombin reaction has not been confirmed. In contrast, there is growing evidence that thrombomodulin (TM), as a critical regulator of the protein C pathway, represents the major anticoagulant mechanism that is operative in both normal and injured blood vessels under physiologic conditions in vivo.

Thrombomodulin generates a physiologic on-demand anticoagulant response by altering thrombin specificity and function. Thrombomodulin provides high affinity binding sites for thrombin at the lumenal surface of the vascular endothelium and on smooth muscle cells. While it is constitutively present on the cell surface, its expression is also upregulated after exposure to thrombin, basic fibroblast growth factor (bFGF), and platelet-derived growth factor (PDGF). TM forms a 1:1 molar complex with thrombin and in the process switches off all known procoagulant/proinflammatory functions of thrombin, and instead channels the catalytic power of the enzyme into complex anticoagulant/antiinflammatory activities. This is accomplished by changing thrombin's mode of action, especially in relation to its macromolecular substrates. TM affects the biological function of thrombin by altering its activity along three distinct substrate dependent anticoagulant pathways. While free thrombin efficiently converts fibrinogen to fibrin, thrombin bound to TM is no longer capable of cleaving fibrinogen, nor is it able to activate factor V or platelets. In addition, TM also enhances the rate of thrombin inactivation by ATIII (about 8-fold), and, perhaps of greatest significance, dramatically accelerates (about 20,000-fold) the ability of thrombin to activate protein C, a vitamin K dependent serine protease. Of note, inactivated thrombin and activated protein C (APC) are released from TM which is then capable of accommodating additional macromolecular substrates. The transfer of fluid phase reactants, such as protein C, thrombin, and ATIII to a catalytic surface and the removal rate of formed products depends upon the kinetics of molecular adsorption and desorption processes, intrinsic rice reaction rate constants, convection by fluid flow, and diffusion within the boundary layer region. Thus, in the presence of competing substrates for a given cofactor and enzyme active site, local flow conditions will have a significant effect on whether thrombin behaves as a pro- or anticoagulant. Surprisingly little information is available regarding the extent to which the flow regime influences the efficiency of TM in vitro or in vivo.

Activated protein C together with its cofactor protein S inactivates two coagulation factors, Va and VIIIa thereby preventing the generation of Xa and thrombin which are critical for the amplification of the coagulation cascade. Activated protein C may promote fibrinolysis. Once generated, APC is one of the slowest of the serine proteases to be inactivated and cleared from the circulation. It may seem somewhat paradoxical that TM promotes the inactivation of thrombin by ATIII since this in turn would limit protein C activation APC generation may proceed only as long as excess thrombin is being generated. Thus, the antithrombin-dependent anticoagulant mechanism of TM ensures that protein C activation is terminated once excess thrombin formation ceases. While local hemodynamic conditions in the arterial and venous circulation are important regulators of APC's capacity to locally inactivate factors Va and VIIIa, this role has not been defined in vivo or in vitro. Nonetheless, it is well-established that patients with protein C or protein S deficiency, as well as those with resistance to APC are prone to develop thromboembolic events. Likewise, mutations in the TM gene may be a risk factor for both venous and arterial thrombosis, including myocardial infarction.

The formation of an effective barrier to the host immune response to transplanted islet cells mandates the exclusion of both cellular and soluble elements. Most current cell encapsulating membranes are capable of isolating the cell transplant from the effects of direct cell-cell interactions, as well as large macromolecules (>100 kD)) such as antibodies or associated immune complexes. However, once an immune response is initiated, the selective exclusion of low molecular weight cytokines and free radicals, while simultaneously permitting the passage of required macromolecules, such as insulin, glucose, or other nutrients, has not heretofore been achieved. Enhancement of current immunoisolation barriers is provided by a capsule design which abrogates the induction of an immune response by inhibiting the release of foreign antigens, minimizing complement activation, and limiting the binding of macrophages to the capsular surface.

Artificial membranes which are porous are provided in this invention. Polyethylene oxide (PEO) dendrimer phase separation was thought to be a potential pitfall in the utilization of this approach to create well defined molecular pores. However, surprisingly, it has been discovered through investigation of lipid/PEO dendrimer mixtures at an air/water interface that PEO dendrimers will readily associate with self-assembled lipid monolayers with relatively little depletion of the dendrimer even at highest surface pressures. PEO dendrimers end-functionalized with dialkyl hydrocarbon chains resemble PEO lipopolymers in which the free ends of the PEO chains now have a common tethered endpoint. X-ray diffraction studies suggest that, at molar concentrations of less than 10 mol %, PEO-lipid conjugates are well mixed with other lipids when examined as multilamellar suspensions supports that end-functionalizing PEO chains with dialkyl groups serves to further compatibilize the dendrimers in a lipid assembly. Fluorescence microscopy studies of lipid/PEO lipopolymer mixtures at an air-water interface confirm that both well mixed and phase-separated regimes can exist depending upon the molecular packing density of the mixture. Nevertheless, even under phase separated conditions, "pure" PEO lipopolymer regimes do not exist. Rather, the assembly most likely consists of PEO-rich and poor regions. Careful selection of the end-terminal dendrimer functionality enhances both component mixing and the ability, even in the presence of a "PEO-rich" phase, of dendrimers to copolymerize with adjacent free lipid monomers rather than homopolymerize with neighboring star molecules. This leads to high regional densities of PEO pores, but, does not alter membrane transport characteristics which are dictated by individual star characteristics and the total number of stars in the membrane. Specifically, end-functionalizing one of the dialkyl chains with a methyl atropate group is useful for this purpose. This functionality is similar in structure to methyl methacrylate, though a phenyl substituent, instead of a methyl group, is present at the alpha carbon position. This polymerizable moiety is unable to homopolymerize, but copolymer with any kind of vinyl unsaturation.

Techniques which facilitate the generation of an ultra-thin, polymeric, membrane-mimetic coating on alginate hydrogels which alter both surface physiochemical characteristics and interfacial transport properties are provided. Specifically, it has been found that diffusivity of BSA through the alginate/aqueous interface was reduced from $3.42 \times 10^{-4}$ cm$^2$/hr to $2.25 \times 10^{-16}$ cm$^2$/hr by the addition of a membrane-mimetic coating. Similarly, the overall mass transfer coefficient for BSA through polymer coated alginate beads was $4.71 \times 10^{-9}$ cm/min which was significantly less than that demonstrated in the prior art for standard poly-L-lysine-alginate capsules ($1.5 \times 10^{-4}$ cm/min) or for microcapsules composed of a hydroxyethylmethacrylate-methyl methacrylate copolymer ($4.21 \times 10^{-6}$ cm/min) (Matthew, H. W. et al. [1993], "Complex coacervate microcapsules for mammalian cell culture and artificial organ development," *Biotechnol. Prog.* 9:510-519; Crooks, C. A. et al. [1990], "Microencapsulation of mammalian cells in a HEMAMMA copolymer: Effects on capsule morphology and permeability. I," *Biomed. Mater. Res.* 24:1241-1262). An ultra-thin, polymeric, membrane-mimetic surface of this invention yields an interface which is impermeable to immunoglobulins. PEO dendrimers can be incorporated into lipid assemblies and individual dendrimers visualized in a filly hydrated environment using cryoelectron microscopy. Microencapsulation reduces host sensitization by limiting the release of islet-associated antigens and capsule-associated macrophages are important in xenograft rejection. Enhancing the permselectivity of the encapsulating barrier, as well as those surface properties which limit the development of host inflammatory response, enhances islet survivability.

This invention applies self-assembly methodology to the design of biomimetic phospholipid-based materials for tissue engineering applications. This approach provides a high level of molecular control over surface order and chemistry and, as a consequence, facilitates the examination of surface molecular determinants which are required for engineering an immunoisolation barrier which achieves an appropriate balance between cell nutrition and protection. The modular nature of this platform provides an enhanced degree of flexibility with respect to the incorporation of additional peptide or carbohydrate lipophilic conjugates or transmembrane pores, transporters (e.g. glucose transporters), or template forming guests for further alteration of surface or transport. The use of dendrimer-based pores allows the artificial membranes of this invention to permit both insulin release and access to nutrients, while excluding potentially cytotoxic mediators of the inflammatory response. The ability to generate molecular sieves of defined size, compacticity, and chemical composition significantly enhances control over membrane permselectivity and provides a useful tool to aid in the identification of soluble factors which lead to islet destruction.

The synthesis of glycocalyx-mimetic membranes comprising membrane-associated heparan and chondroitin sulfite reduces complement and macrophage-mediated xenograft rejection.

Enhanced control of both transport properties and surface physiochemical characteristics are important steps in the development of an effective immunoisolation barrier critical to the success of pancreatic islet cell transplantation. The natural cell membrane establishes an important paradigm for the design of a biomimetic immunoisolation barrier with improved performance characteristics because of its capacity to control interfacial transport by the presence of channels, transporters, and pores, as well as through its ability to act as a template for more complex composite structures with other immunoregulatory macromolecules. A bioactive barrier with highly tailored transport and surface properties incorporating dendritic polymers as synthetic molecular channels, as well as GAG neoglycolipids with anti-inflammatory properties, into a stable, polymeric lipid membrane is provided in order to isolate and preserve donor islets by limiting the induction of maladaptive events generated by the host inflammatory response. The specific design characteristics of the proposed immunoisolation barrier are dictated, in part, by the molecular and cellular mechanisms responsible for the rejection of encapsulated xenogeneic islets.

EXAMPLES

Example 1

Preparation of Membrane-mimetic Film on Microbeads

Reagents. All starting materials and synthetic reagents were purchased from commercial suppliers unless otherwise noted. Poly-L-lysine (PLL; 21-479 kD) was purchased from Sigma. Alginate (ca. 41% guluronic acid) was obtained from ISP alginate (San Diego, Calif.) and used as received. N,N-dioctadecylcarbamoyl-propionic acid (DOD), poly(HEA-DOD)$_{6:3}$, 1-palmitoyl-2-(12-(acryloyloxy)dodecanoyl)-sn-glycero-3-phosphorylcholine (mono-AcrylPC), and 1-palmitoyl-2-(12-(acryloyloxydodecanoyl)-sn-glycero-3-phosphorylethanolamine-fluorescein isothiocyanate (mono-AcrylPE-FITC) were synthesized as previously described. (Marra, K. G., Winger, T. M., Hanson, S. R. & Chaikof, E. L. [1997] *Macromolecules* 30:6483-6488; Chon, J. H., Marra, K. G. & Chaikof, E. L. [1999] *J. Biomat. Sci. Polymer Ed.* 10, 95-108; Sells, T. D. & O'Brien, D. F. [1994] *Macromolecules* 27, 226-233; Sun, X. L., Liu, H., Orban, J. M., Sun, L. & Chaikof, E. L. [2001] Submitted to *Bioconjugate Chemistry*.)

Instrumentation. Ellipsometry data was obtained using a PlasMos ellipsometer, Model SD2300 equipped with a HeNe laser as a light source. The light was incident at an angle of 70° to the surface normal. The organic layer was assumed to have a refractive index n of 1.45.

High-resolution scanning electron micrographs (HR-SEM) were obtained using an in-lens field emission scanning electron microscope (ISI DS-130F Schottky Field Emission SEM) that was operated at 5 kV. Sample-containing silicon chips were mounted onto aluminum specimen stubs with silver paste, degassed for 30 minutes, and coated with a 1 nm chromium (Cr) film.

Infrared Spectroscopy. Spectra were acquired using a Bio-Rad FTS-60 Fourier Transform Infrared (FT-IR) spectrometer equipped with a wide band MCT detector, collected with 1024 scans, triangular apodization, and 4 $cm^{-1}$ resolution. Polarized infrared external reflection spectra were obtained using a Harrick external reflection accessory (600 angle of incidence) (Ossining, N.Y.) with infrared radiation polarized perpendicular or parallel to the surface normal using a Molectron ZnSe wire grid polarizer (Portland, Oreg.).

Fluorescence Microscopy. Fluorescence images were acquired using a Zeiss epifluorescence microscope under 50× magnification, illuminated with a xenon-mercury arc lamp, and a low light level SIT camera detector.

Statistical copolymerization of 2-hydroxymethyl acrylate (HEA) and styrene sulfonate (SSS).HEA (1.15 mL; 10 mmol) and SSS (0.206 g; 1.0 mmol) were dissolved into 20 mL dimethyl sulfoxide. 2,2'-Azobisisobutyronitrile (AIBN; 18 mg; 0.11 mmol) was added, the solution purged with $N_2$ for 30 min, and the reaction mixture placed in a 70° C. oil bath for 20 h. The reaction mixture was slowly added to 400 mL of cold $CH_2Cl_2$ with vigorous stirring. A colorless glue-like precipitate formed and the solid rinsed twice with $CH_2Cl_2$ prior to overnight drying under vacuum. The final product was a white solid that was highly hygroscopic and was referred to as poly(HEA-SSS)$_{10}$. Yield: (1.16 g, 85%). $^1$H NMR (CD$_3$OD), δ: 3.99 (2H, CH$_2$ of HEA), 7.50 and 7.04 (4 H, Ar—H of SSS). $^1$H NMR (DMSO-d6), δ: 7.50 (br, Ar—H); 7.04 (br, Ar—H); 3.99 (br, CH2—O—C═O); 3.54 (br, CH2—OH); 2.54 (br, CH); 2.25 (br, CH2). GPC (LLS): Mn=25,300, PDI=1.75.

Synthesis of an HEA-SSS-DOD terpolymer. Poly(HEA-co-SSS)$_{10:1}$ (0.410 g; 3.0 mmol of HEA mer-unit) was dissolved in 15 mL dimethylformamide (DMF) and later diluted with 10 mL of $CH_2Cl_2$. N,N-dioctadecylcarbamoyl propionic acid (DOD; 0.652 g; 1.05 mmol) in 10 mL of $CH_2Cl_2$ was slowly added to the above solution followed by the addition of p-dimethyl aminopyridine (12.8 mg; 0.11 mmol). A small volume of DMF (ca. 0.5 ml) was added to maintain clarity of the solution, the reaction mixture placed in an ice-water bath, and dicyclohexylcarbodiimide (0.284 g, 1.38 mmol) in 3 mL of $CH_2Cl_2$ was added dropwise. The reaction proceeded overnight under $N_2$. The reaction mixture was then evaporated to dryness and mixed with 20 mL of diethyl ether. The mixture was filtered, the filtrate evaporated to dryness, dissolved in 5 mL of $CH_2Cl_2$, and the polymer precipitated in 100 ml of acetonitrile. The product was a white powder and $^1$H NMR and elemental analysis confirmed a monomer ratio in the terpolymer of HEA:DOD:SSS of 6:3:1. This compound was referred to as poly(HEA$_6$:DOD$_3$:SSS,). Yield: 0.770 g, 73%. $^1$H NMR (CDCl$_3$), δ: 4.27 (br., CH$_2$—O—C═O); 3.76 (br. CH$_2$—OH); 3.22 (br. CH$_2$—N—C═O); 2.62 (br., CH$_2$—C═O, CH—Ar); 2.39 (br., CH$_2$, CH); 1.56 (br., CH$_2$); 1.47 (br., CH$_2$); 1.25 (br., CH$_2$); 0.87 (br., CH$_3$). IR (KBr pellet): 1732 $cm^{-1}$ (O═C—O—), 1649 $cm^{-1}$ (O═C—N). GPC (LLS): Mn=49,800, PDI=1.80. Elemental analysis:

Calculated: 67.83% C, 10.20% H, 18.80% 0, 1.37% N; 1.04% 5; Observed: 67.54% C, 10.28% H, 18.77% 0, 1.80% N, 0.96% S.

Preparation of (PLL-alginate)$_5$-PLL-polymer films on glass. PLL and alginate were prepared at concentrations of 0.10 w/v % and 0.15 w/v % in PBS, respectively. In the generation of a polyelectrolyte multilayer, the contact time was approximately 30 seconds for each solution and surfaces rinsed three times with water between each coating solution. (PLL-alg)$_5$-PLL coated glass slides were exposed to solutions of either poly(HEA-DOD)$_{6:3}$ or poly(HEA-DODS SS)$_{6:3:1}$ in triethylene glycol (TEG) at concentrations of 3 mmol of DOD or 1 mmol SSS, respectively. Contact times ranged from 30 seconds to 20 h, after which slides were briefly rinsed once with TEG and five to ten times with water.

Vesicle fusion. Large unilamellar vesicles (LUV) of 10 mM acrylate-PC in 20 mM sodium phosphate buffer (pH 7.4) were prepared by three successive freeze/thaw/vortex cycles using liquid $N_2$ and a 40° C. water bath. The LUVs were then extruded 21 times each through 2.0 μm and 600 nm polycarbonate filters and the solution diluted to 1.2 mM with 20 mM sodium phosphate buffer (pH 7.4) and 150 mM NaCl. Alkylated substrates were incubated with the vesicle solution at 37° C. for fusion times, as specified.

In situ photopolymerization of a supported lipid film. A stock solution of co-initiators was prepared as 10 mM Eosin Y (EY), 225 mM triethanolamine (TEA), and 37 mM VP in water. A 10:1 (mol/mol) monomer/EY ratio was used for photopolymerization. Thus, 10 μL of initiator was added with stirring to the vial containing 1 mL of vesicle solution and test substrate. The vial was purged with $N_2$ for 15 mm and the test sample irradiated with visible light at a distance of 6.5 cm for 30 mm (50 mW/cm$^2$).

Generation of alginate beads coated with a polymerized lipid film. Microbeads (d~300 μm) were prepared using an electrostatic bead generator (Pronova Biomedical, Inc.). The alginate solution (2.0% w/v, pH 7.4) with or without cells or FITC-labeled dextran was extruded at a flow rate of 0.2 mL/min through a flat end needle with an internal diameter of 0.10 mm into a 1.1% w/v CaCl$_2$ solution. Alginate beads were incubated with PLL (0.10% w/v) for 30 seconds and then rinsed twice with PBS. Beads were then incubated in dilute alginate (0.15% w/v) for 30 seconds followed by two brief saline rinses. This process completed a cycle of forming a single PLL-alginate bilayer and was repeated four times followed by a final 30-second incubation in PLL. The beads were then incubated in a solution containing poly(HEA$_6$:DOD$_3$:SSS,) (0.10 mmol of SSS in 1% DM50) for 30 seconds and subsequently rinsed three times with PBS.

The formation of a supported lipid film was achieved by incubating beads (0.5 mL) in a lipid vesicle solution (1 mL) for 4 h at 37° C. with gentle mixing. At the end of the incubation period, 10 µL of a photoinitiator mixture (10 mM EY, 225 mM TEA, and 37 mM VP in water) was added. The solution was irradiated with visible light (50 mW/cm$^2$) for 30 mm at room temperature. Beads were then rinsed three times in PBS.

Characterization of molecular transport across microbeads coated with polymeric membrane-mimetic barrier. FITC-labeled dextran of various molecular weights (9, 21, 38, 72 kD) were used to study the transport properties of the beads at various stages of polyelectrolyte and lipid membrane coating. Dextran containing beads were incubated at room temperature in saline and aliquots of the bathing solution were anal by UV-VIS absorption spectroscopy at timed intervals.

Viability of CHO K-1 cells within alginate microbeads coated with a membrane-mimetic encapsulation barrier. CHO K-1 cells (ATCC, Inc.) were suspended in alginate solution at a cell density of 4-6×10$^6$ cells/mL and extruded into a calcium chloride bath, as detailed above. The methodology of microbead formation was otherwise similar to that previously described with several modifications to maximize cell viability. Specifically, coating solutions were supplemented with glucose (3.15 g/L), unilamellar vesicles were prepared in Ham's F-12 medium without serum and phenol red, and all procedures performed, where possible, in an incubator at 37° C. and 5% CO$_2$. Cell viability was characterized after bead coating and after in vitro incubation periods of up to 48 hours using the LIVE/DEAD® Cell Viability/Cytotoxicity Kit (L-3224; Molecular Probes, Inc).

Layer-by-layer assembly of a membrane-mimetic film on a charged hydrated substrate. Thin films based upon the assembly of a polyelectrolyte multilayer involve the sequential adsorption of oppositely charged polymers from dilute solution onto a substrate. (Decher, G. [1997] Science 277:1232-1237.) In the process, an interpenetrated multilayer structure is produced where film thickness is dependent upon the charge density and molecular weight of the polyelectrolyte, as well as the total number of deposited layers. (Lvov, Y. et al. [1993] Langmuir 9:481-486; Mao, G., et al. [1995] Langmuir 11:942-952.) In this report, the alginate-poly-L-lysine system was used to generate a PEM. Alginate and poly-L-lysine are negatively and positively charged polyelectrolytes, respectively, and have been the subject of intense study as complex gels, colloidal particles, and multilayers. Poly-L-lysine was always deposited last to produce a positively charged substrate for electrostatic anchoring of the negatively charged amphiphile and subsequent lipid film formation.

Figure 2:
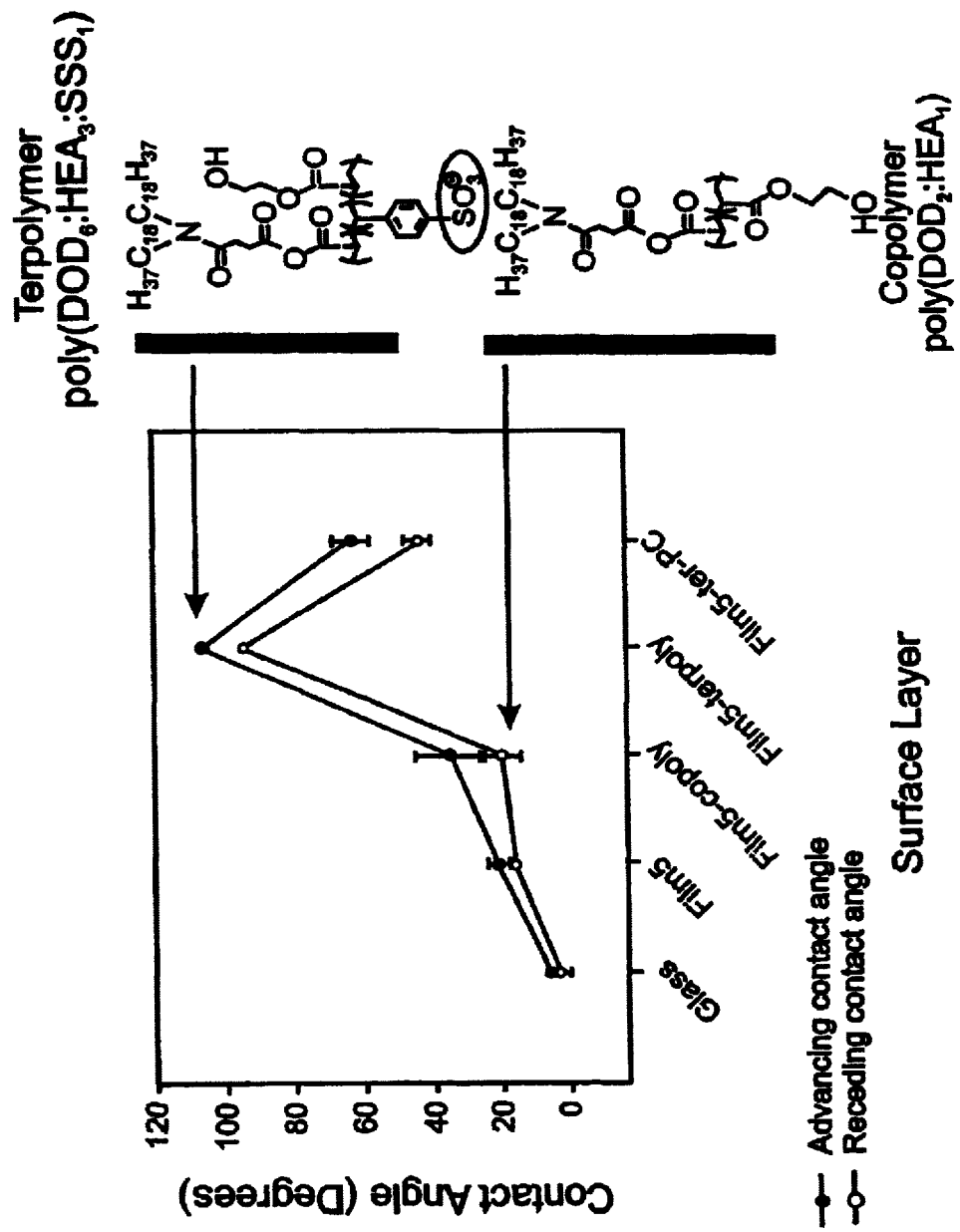
FIG. 2 shows advancing contact angles with successive assembly of terpolymer and lipid films on an alginate/PLL multilayer: (alginate/PLL)5=Film5; (alginate/PLL)5/terpolymer=Film5-terpoly; (alginate/PLL)5/terpolymer/PC=Film5-terpoly-PC. "Copoly" designates a HEA:DOD (2:1) copolymer without sulfonate anchors and demonstrates inability of the polymer to absorb to PLL.

Contact angles were measured at various stages of the film forming process FIG. 2). As anticipated, advancing contact angles were low for successive alginate (~5°) and PLL (~10°-20°) multilayers. After the formation of three PLL/alginate bilayers, contact angles approached constant values for both layers with little change over at least 20 successive bilayers (data not shown). Relatively small differences in advancing and receding contact angles over a range of PLL molecular weights (21-479 kD) were also observed. In all subsequent studies, membrane-mimetic film formation was performed on a multilayer consisting of PLL (479 kD) adsorbed onto five bilayers of PLL/alginate ((PLL/alginate)$_5$-PLL).

The amphiphilic polymer, poly(HEA:DOD:SSS), was coated onto the surface of a (PLL/alginate)$_5$-PLL film with advancing contact angles exceeding 100° after incubation periods as short as 30 seconds. Notably, a 24-hour incubation of the substrate with a copolymer of HEA and DOD, at a similar molar concentration of DOD, did not result in significant copolymer adsorption, as confirmed by an increase in advancing contact angles from 20 to 30 g. Thus, the presence of anionic sulfonate groups are critical for polymer adsorption.

Vesicle fusion was chosen for deposition of a lipid assembly on the alkylated polyelectrolyte multilayer. After in situ photopolymerization of the deposited phospholipid layer an advancing contact angle of ~60° was observed, in good agreement with previous studies. These values are also consistent with prior reports of Hayward et al. (1986) Biomaterials 7:252-258) and Köhler et al. [1996] J. Biomed. Mater. Res. 32:237-242 of phosphorylcholine derivatized glass, as well as our own data in other polymerized lipid systems. Of note, little change in contact angles was observed during a three week incubation period in PBS.

Additional surface sensitive techniques afforded further insight into film properties. High-resolution in-lens FESEM provided a convenient method to examine surface topography over large film areas. While occasional vesicles were noted on the film surface, little overall surface roughness was observed. Ellipsometry was used to measure the hydrated thickness of each film layer and x-ray photoelectron spectroscopy (XPS) to further define atomic level surface properties. A thickness of 28 Å was observed per alginate-PLL bilayer and is consistent with prior reports of this system. The thickness of the adsorbed terpolymer was 52 Å and the thickness of the supported lipid film was 23 Å. This value compares favorably with measurements determined by x-ray diffraction (Nagle, J. F. et al. [1996] Biophys. J. 70:1419-1431) or neutron reflectivity (Meuse, C. W. et al. [1998] Biophys. J. 74:1388-1398) for liquid-crystalline DPPC multilayers and supported monolayers, respectively. XPS confirmed that after the deposition of five or more alginate-PLL bilayers, surface Si was no longer observed. Significantly, sulfur was identified after terpolymer adsorption and phosphorus demonstrated after lipid vesicle fusion and polymerization. (See Tables 1-3.)

Structural characterization of the supported lipid assembly by infrared spectroscopy. Infrared spectra were acquired during each stage of film construction in order to identify functional group characteristics that were unique to each film component, as well as to provide insight into acyl chain orientation. Significantly, this analysis provides both a framework for characterizing film stability under varying environmental conditions and establishes the level of disorder within the supported lipid assembly. This latter feature may have an important impact on film properties, including membrane permeability and the capacity to organize and appropriately orient membrane based proteins. The perpendicular (R$_s$) and parallel (R$_p$) polarized external reflection spectra are presented in FIG. 3.

Notably, the polarized IR spectra of the PLL-alginate multilayer revealed PLL-dependent bands including an amide I stretch and a shoulder containing the N—H stretch of —$NH_3^+$ (1650, 1615 $cm^{-1}$, respectively). The symmetric (1410 $cm^{-1}$) and antisymmetric (1550 $cm^{-1}$) stretching vibrations of the carboxylate ion (COO—) are unique to alginate and could be resolved in the $R_p$ polarized spectra A broad and strong —OH vibration, due to alginate, was observed between 3600-3000 $cm^{-1}$.

Addition of the terpolymer (FIG. 3B) was associated with intense symmetric and antisymmetric methylene stretches, located from 3000-2800 $cm^{-1}$, as well as an ester carbonyl band centered at 1734 $cm^{-1}$. These vibrations can be attributed to DOD and HEA groups, respectively. The spectral intensity of unique PLL (amide I stretch) and alginate (antisymmetric and symmetric COO— stretches) vibrations were reduced, but remain identifiable.

Figure 3A:
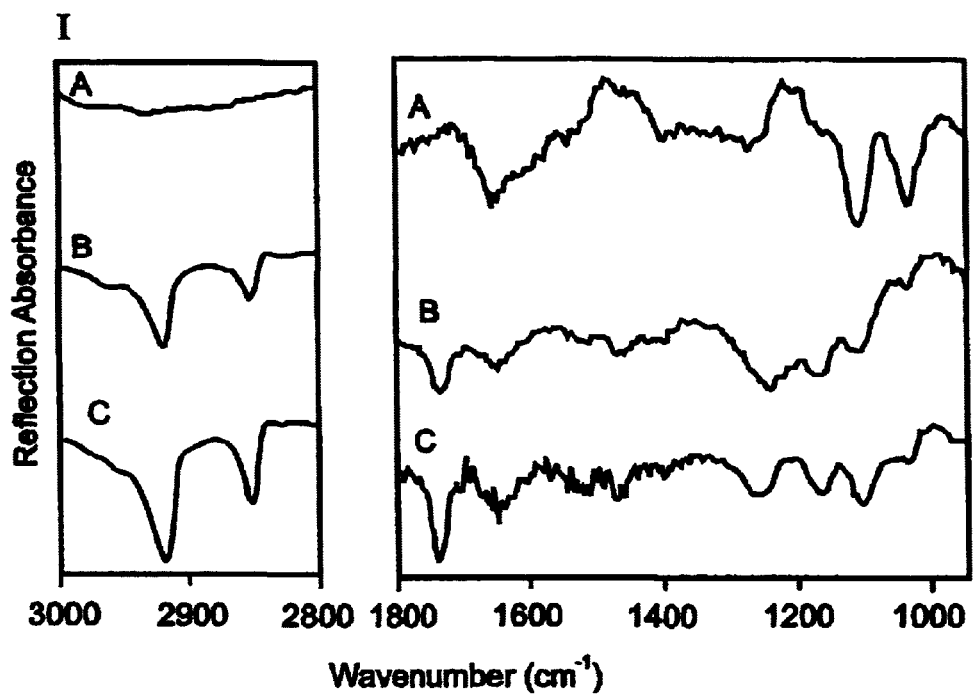
FIG. 3A. shows a perpendicular ($R_s$) polarized external reflection infrared spectra following successive adsorption of A: (PLL/alginate)$_5$-PLL; B: poly(HEA$_6$:AOD$_3$:SSS$_1$); and C: polymerized lipid film.

Dramatic changes in the $R_s$ and $R_p$ polarized IR spectra were seen after fusion and lipid polymerization (FIG. 3C). A band at ~1263 $cm^{-1}$ is noted in the $R_s$ polarized spectrum due to the antisymmetric P═O stretch and intensity increases due to the $v_a$ and $v_s$ $CH_2$, the C═O (ester carbonyl), and C═O—O—C stretching absorption modes (1120-1105 $cm^{-1}$) were also observed in both polarized spectra. The latter absorption modes were present in both lipid and terpolymer components.

The most notable difference, however, occurs in the $v_a$ and $v_s$ $CH_2$ stretching modes of the $R_p$ polarized spectrum where bands shifted from positive to negative intensity after lipid deposition and polymerization (FIG. 3 II, B and C). Positive and negative absorption bands have been theoretically predicted and experimentally observed in studies of monomolecular thin films coated onto silicon and other semiconductor substrates. (Dluhy, R. A. [1986] *J. Phys. Chem.* 90:1373-1379; Wong, J. S. & Yen, Y. S. [1988] *Appl. Spectrosc.* 42:598-604; Mielczarski, J. A. and Yoon, R. H. [1989] *J. Phys. Chem.* 93:2034-2038; Yen, Y. -S. and Wong, J. [1989] *J. Phys. Chem.* 93:7208-7216.) Moreover, this behavior was observed in a recent investigation of a polymeric lipid film deposited on OTS/Si. (Decher, G. [1997] *Science* 277:1232-1237.) Using theoretical reflection-absorption plots generated from Fresnel reflection equations for a three-phase system (Hasegawa, T. et al. [1995] *Langmuir* 11:1236-1243; Sakai, H. and Umemura, J. [1998] *Langmuir* 14:6249-6255), the positive and negative absorption modes were correlated, qualitatively and quantitatively, with the molecular orientation of the alkyl chains of OTS and the supported lipid. (Orban, J. M. et al. [2000] *Macromolecules* 33:4205-4212.)

Figure 3B:
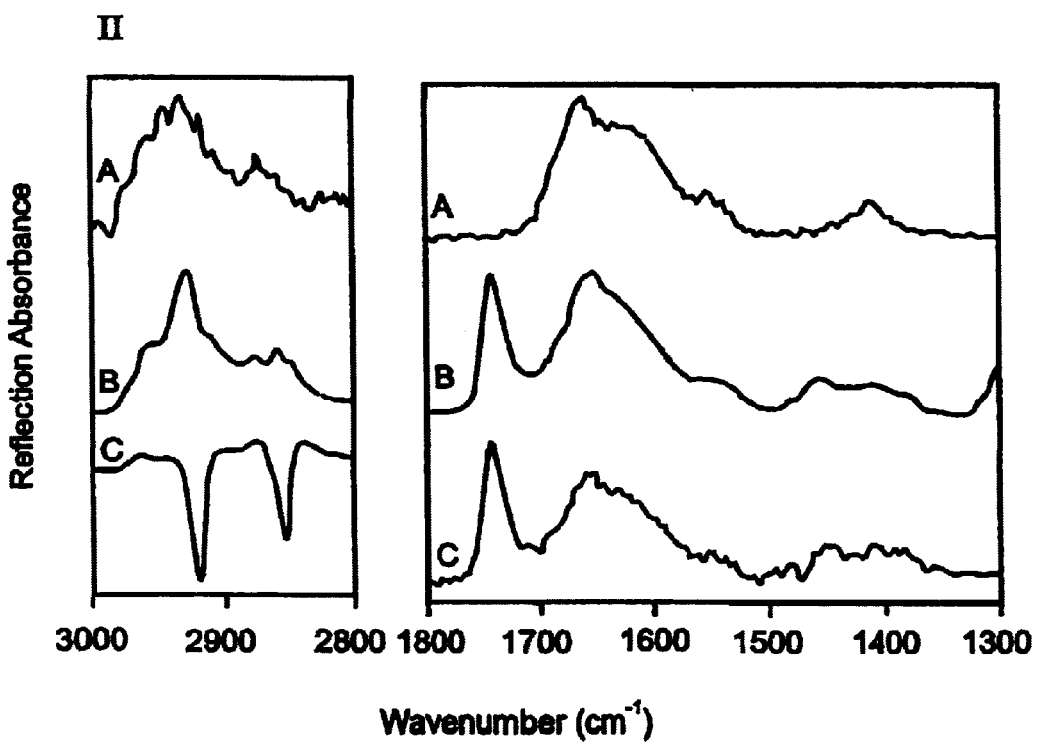
FIG. 3B. shows a parallel ($R_p$) polarized external reflection spectra following successive adsorption of A: (PLL/alginate)$_5$- PLL; B: poly(HEA$_6$:AOD$_3$:SSS$_1$); and C: polymerized lipid film.

The positive methylene absorption bands in the $R_p$ polarized external reflection spectra (FIG. 3B) indicate that the molecular orientation of the terpolymer alkyl chains is random and tilted away from the surface normal. This is also supported by the frequency position of the methylene stretching vibrations, which are indicative of hydrocarbon chain order. Tasumi, M. S. and Miyaza, T. J. [1962] *J. Mol. Spectrosc.* 9:261; Snyder, R. G., Hsu, S. L. & Krimm, S. [1978] *Spectrochim. Acta, Part A* 34A395-406; Painter, P. C. C. et al. [1982] *The Theory of Vibrational Spectroscopy and its Application to Polymeric Materials* [John Wiley & Sons, New York].) Specifically, the average positions of the methylene symmetric ($v_s$, $CH_2$) and antisymmetric ($v_a$ $CH_2$) stretching modes in the $R_s$ polarized spectra are 2854.7 and 2925.3 $cm^1$ (FIG. 3B). These positions imply that the hydrocarbon chains are disordered and possess both trans and gauche conformers. This is not altogether unexpected as the alkyl chains present in the terpolymer are relatively long and may not be tightly packed together due to the HEA spacer groups (FIG. 1).

After fusion and polymerization of the acrylate-PC assembly, the methylene absorption bands reversed in intensity. Qualitatively, this result indicates that the acyl chain tilt is closer to the surface normal. Presumably, the mobile hydrocarbon chains of the terpolymer are now held to a smaller chain tilt due to van der Waal interactions with associated lipid acyl chains. Using a film thickness determined by ellipsometry and a previously described calculation procedure (Orban, J. M. et al. (2000) *Macromolecules* 33, 4205-4212), the average orientation after the addition of the lipid was determined to be 39.5°. This result undoubtedly includes Om orientation of both lipid and terpolymer alkyl chains. The increase in chain order and orientation is also supported by the frequency position of the methylene symmetric and antisymmetric stretching vibrations, which were 2853.9 and 2922.3 $cm^{-1}$, respectively. The addition of the acrylate-PC film is associated with a conformational ordering of the hydrocarbon chains, which coincides with an increase in the hydrocarbon chain tilt. Of note, chain tilts of 34° and 38° have been observed for non-polymerized lipid monolayers of DPPC when produced on a self-assembled monolayer of octadecanethiol on gold by Langmuir-Schaefer or vesicle fusion methods, respectively. (Meuse, C. W. et al. [1998] *Biophys. J.* 74:1388-1398.) Thus, a remarkable degree of acyl chain order can be maintained even after polymerization of the lipid assembly.

Figure 4:
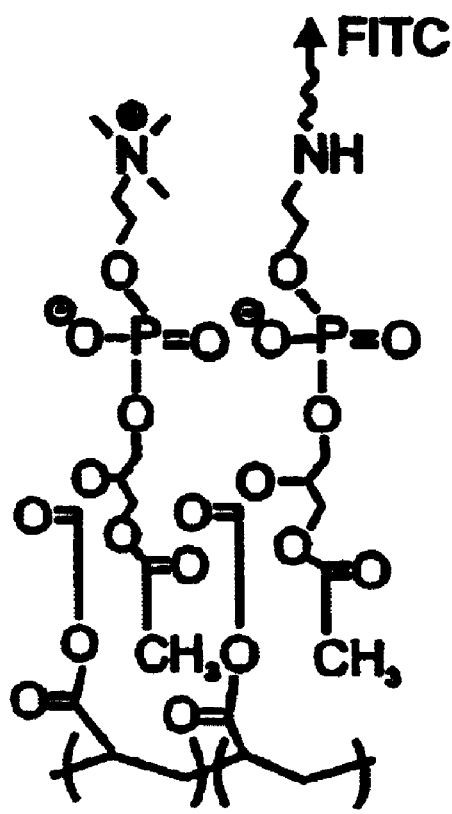
FIG. 4 shows an alginate/PLL/terpolymer coated silicon slide after vesicle fusion and polymerization of a lipid assembly comprised of Acryl-PC and AcrylPE-FITC (1 mol %).

A polymeric lipid film, assembled on a polyelectrolyte multilayer, is stable in a high shear flow environment. At each stage of the coating procure, films were exposed to PBS at a wall shear rate of 2000 $sec^{-1}$ for a two-hour contact period. Polarized IR spectra were unchanged with the exception of the terpolymer-coated sample in which significant chain ordering was induced by exposure to high shear (data not shown). An acrylate functionalized phosphatidylethanolamine, which allowed the introduction of FITC by acylation of the amine group, was designed in order to further enhance the ability to visually monitor film stability (FIG. 4). Thus, vesicles doped with 1 mol % of mono-AcrylPE-FITC were fused onto terpolymer-coated substrates and exposed to flow. No discernable loss of fluorescence signal was observed.

Figure 5A:
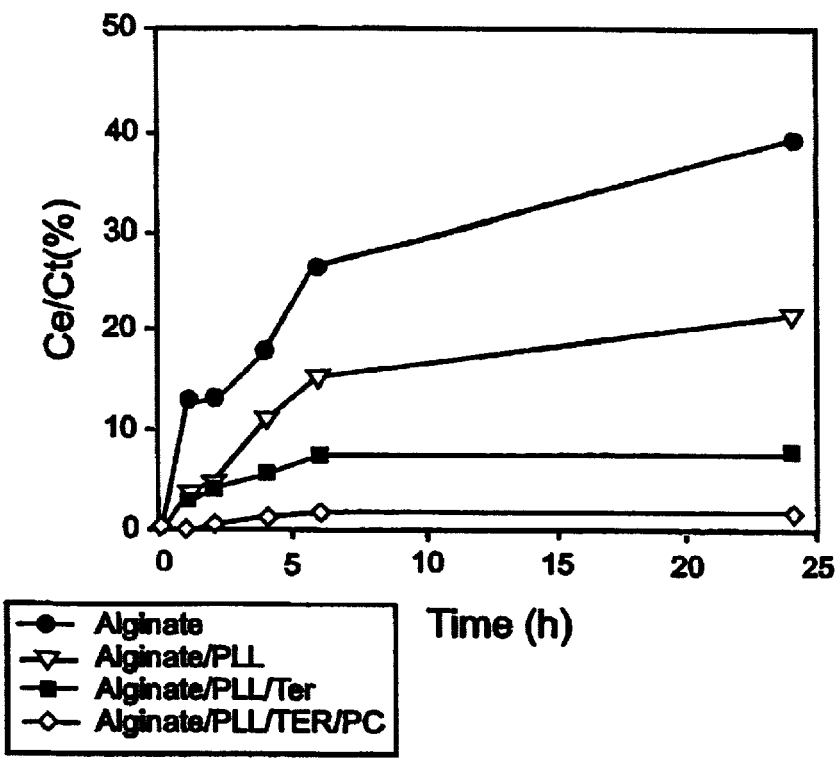
FIG. 5(A) shows the release rates of encapsulated 71 kD FITC-dextran from alginate beads following successive adsorption of (PLL/alginate)$_5$-PLL; poly(HEA$_6$:DOD$_3$:SS$_1$), and a polymerization lipid film.
Figure 5B:
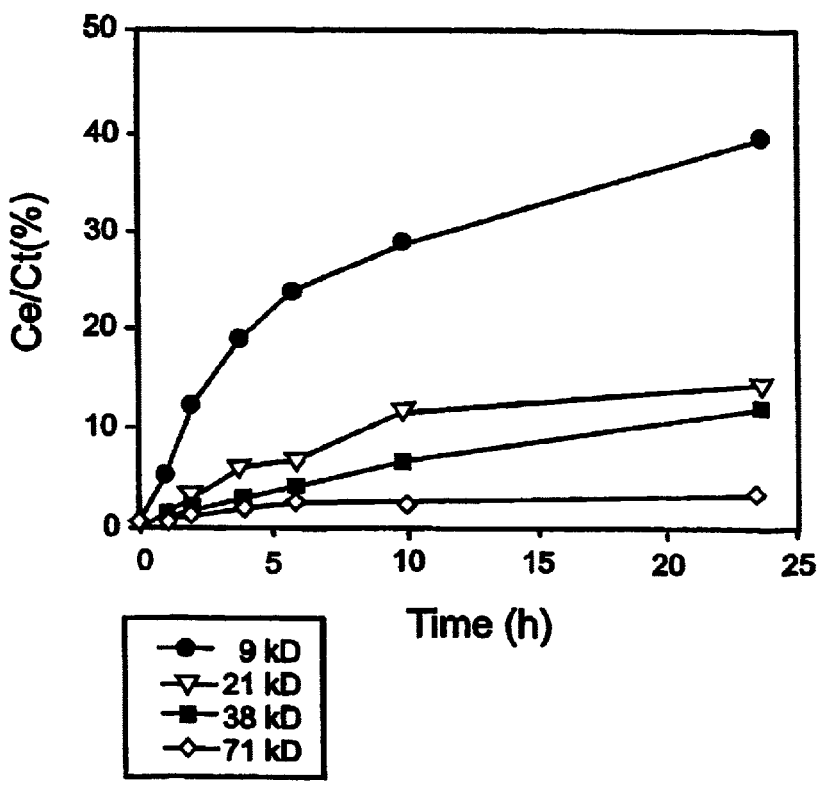
FIG. 5(B) shows release rates of encapsulated FITC-dextrans (MW 9, 21, 38 kD) from alginate-PLL microbeads coated with a photopolymerized membrane-mimetic barrier (T 23° C.).

Barrier permeability of a PEM is modulated by coating with a membrane-mimetic film. The release of encapsulated 71 kD FITC-dextran as related to layer-by-layer deposition of film components is presented in FIG. 5A. A progressive decrease in the rate and magnitude of dextran release was observed with the addition of each successive film layer. While little release of 71 kD dextran was noted following the formation and polymerization of the supported lipid film, the release of lower molecular weight dextrans (9, 21, and 38 kD) was observed (FIG. 5B). These data are indicative of some level of non-uniformity in film coating, however, the membrane-mimetic surface is impermeable to immunoglobulins, which is a critical requirement for designing an effective immunoisolation barrier.

Encapsulated cell viability is maintained during the assembly and polymerization of a membrane-mimetic coating. The impact of materials, procedures, and conditions required for membrane-mimetic film formation on cell viability was analyzed using alginate encapsulated CHO cells. In preliminary studies, approximately 50% of cells survived encapsulation when alginate, PLL, amphiphilic polymer, and lipid vesicles were prepared in PBS alone. To improve cell survival, glucose was added to all PBS, alginate, and PLL solutions and both polymer adsorption and vesicle fusion steps were performed in Ham's F-12 medium without serum and phenol red. In addition, with the exception of vesicle fusion, all coating and rinse procedures were performed using ice-chilled solutions, so as to lower the metabolic demands of the cells. This strategy had no effect on membrane structure or properties. The ability to produce a stable, uniform membrane-mimetic film on bead surfaces was demonstrated through doping of the membrane-mimetic film with a FITC-labeled lipid, transport properties were unchanged, and overall cell viability exceeded 90%.

Conclusions. A stabilized, polymeric membrane-mimetic surface was produced on an alkylated polyelectrolyte multilayer by in situ photopolymerization of a lipid assembly. Molecular characterization confirmed the generation of a well-ordered supported lipid monolayer, which was stable under high shear flow conditions and capable of modulating interfacial molecular transport. In addition, the ability to use this system as a cell encapsulation barrier is illustrated. The addition of a stable, supported lipid membrane provides an additional mechanism for controlling both the physiochemical and biological properties of a polyelectrolyte multilayer, thus making it possible to optimize the clinical performance characteristics of artificial organs and other implanted medical devices.

Example 2

Cytomimetic Biomaterials: Synthesis and Analysis of Bioactive Membrane-Mimetic Structures Synthesis of Lipopeptide and Glycolipid Conjugates Site-specific methods have been developed for the synthesis and purification of lipid-peptide and glycolipid macromolecules in the absence of complex blocking group strategies. (Winger, T. M. et al. [1995] Bioconjug. Chem. 6:323-326; Winger, T. M. et al. [1995] J. Liquid Chromatogr. 18:4117-4125; Winger, T. M. et al. [1995] Biomaterials 16:443-449; Winger, T. M. and Chaikof, E. L. [1997] Langmuir 13:3256-3259; Sun, L. and Chaikof, E. L. [1997] Bioconj. Chem. 8:567-571; Sun, L. and Chaikof, E. L. [1998] Carbohydrate Res. 370: 7-81.) Using these techniques, the orientation of the coupled peptide and carbohydrate has been maintained, which is often required for effective ligand-receptor interactions. The conjugates thus obtained are incorporated into self-assembling systems, such as lipid monolayers for behavioral studies at an air-water interface or as biomembrane-mimicking structures (liposomes or substrate-supported membranes) for bioactivity assays.

The scheme for the formation of lipopeptide conjugates is based on an $SN_2$-type reaction of a thiol-terminated peptide with an N-bromoacetyl derivative of phosphatidylethanolamine (PE). Spacer chain flexibility hydrophobicity, and length can all be easily modified. Integrin and heparan sulfate binding lipopeptide conjugates have been synthesized and analyzed, including mixing properties in membrane-mimetic monolayers and their biological activity as components of membrane-mimetic films. (Winger, T. M. and Chaikof, E. L. [1997] Langmuir 13:3256-3259.) Receptor specificity for lipopeptide conjugates has been demonstrated in vitro by the complete loss of bioactivity upon replacement of all-i amino acid sequences with the corresponding all-d sequence (i.e. the optical isomer of the active peptide).

A "neoglycocalyx" can be created by functionalizing a supported membrane with heparan sulfates or bioactive sequences derived from parent polysaccharides. The generated glycocalyx would serve to limit the activation of the coagulation cascade and act as a molecular sink for heparan sulfate binding endothelial growth factors. While methods have been described for covalently conjugating saccharides to lipids, the reported reaction schemes appear to be inefficient and often involve the destruction of the reducing sugar of the oligosaccharide sequence. Likewise, only limited success has been achieved in incorporating a spacer and for optimizing conjugate bioactivity. (Defrees, S. A. et al. [1996] J. Am. Chem. Soc. 18:6101-6104; Kuhlenschmidt, T. B. and Lee, Y. C. [1983] Biochem. 23:3569; Biessen, E. A. L. et al. [1995] J. Med Chem. 38:1538-46; Wang, P. et al. [1993] J. Am. Chem. Soc. 115:10487; Schmidt, R. R. [1989] Pure Appl. Chem. 61:1257-70; Stall, M. S. et al. [1988] Biochemical J. 256:661-4.) In order to circumvent these limitations, methodology was developed using a spacer arm, which possessed the required carbonyl functionality for conjugation to PE via a reductive amination reaction (Scheme 1). (Sun, L. and Chaikof, E. L. [1997]Bioconj. Chem. 8:567-571.)

Neoglycophospholipids tethered by alkyl chains of 3 to 16 methylene units have been synthesized in good overall yields (40-50%) in four steps. Conjugated monosaccharides have included glucose, mannose, fructose, galactose, and N-acetyl glucosamine. More recently, the reaction procedure has been extended to oligosaccharide ligands. (Sun, L. and Chaikof, E. L. [1997] Bioconj Chem 8:567-571; Sun, L. and Chaikof, E. L. [1998] Carbohydrate Res. 370:77-81; Grande, D. et al. [2000]Macromolecules 33:1123-1125.)

Figure 6:
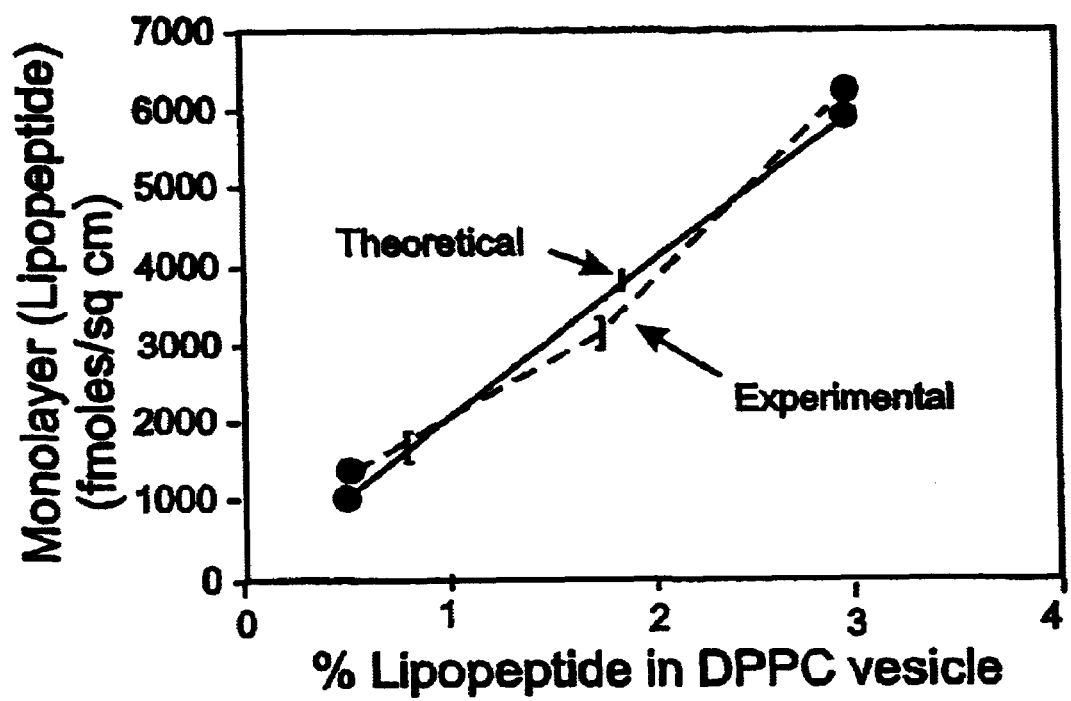
FIG. 6 shows the correlation between lipopeptide concentration in vesicle formation and on a surface membrane.

Synthesis and characterization of supported membrane-mimetic surfaces with multiple lipopeptide constituents. Correlative investigations using radiochemical titration and atomic force microscopy. Supramolecular membrane complexes on solid supports create useful systems for probing and controlling clinically adverse processes at the host-material interface. The initial scientific motivation for studying lipid assembly on solid supports was the development of a reproducible method for the preparation of stable, immobilized membrane-mimetic monolayers to be used in the characterization of cell- and protein-membrane interactions. In order to create a peptide functionalized surface supported membrane; mixed lipopeptide/dipalmitoylphosphatidylcholine (DPPC) liposomes were prepared (Winger, T. M. and Chaikof, E. L. [1998] Langmuir 14:4148; Winger, T. M. and Chaikof, E. L. [1998] In: Materials Science of the Cell, Vogel, V., ed., Pittsburgh: MRS Publications; Winger, T. M. et al. [1999] Langmuir 15:3866). Prior to vesicle formation, lipopeptides were radioiodinated and known amounts of lipopeptide and DPPC were then mixed in a solution of 20 mM sodium phosphate (pH 7.4) with 1% (w/v) octyl-β-D-glucoside (OG). Samples were dialyzed against 4 exchanges of OG-free buffer followed by fusion of the vesicle solution onto an alkylated (octadecyltricholorosilane, 0TS) glass surface. Experiments confirmed monolayer formation with 1:1 correspondence between the concentration of lipopeptide in the vesicle and that found on planar substrates following fusion (FIG. 6). Correlative wet AFM studies have been reported in greater detail elsewhere. (Winger, T. M. and Chaikof, E. L. [1998] Langmuir 14:4148; Winger, T. M. and Chaikof, E. L. [1998] In: Plant A, Materials Science of the Cell, Pittsburgh: MRS Publications; Winger, T. M. et al. [1999] Langmuir 15:3866.)

Figure 7:
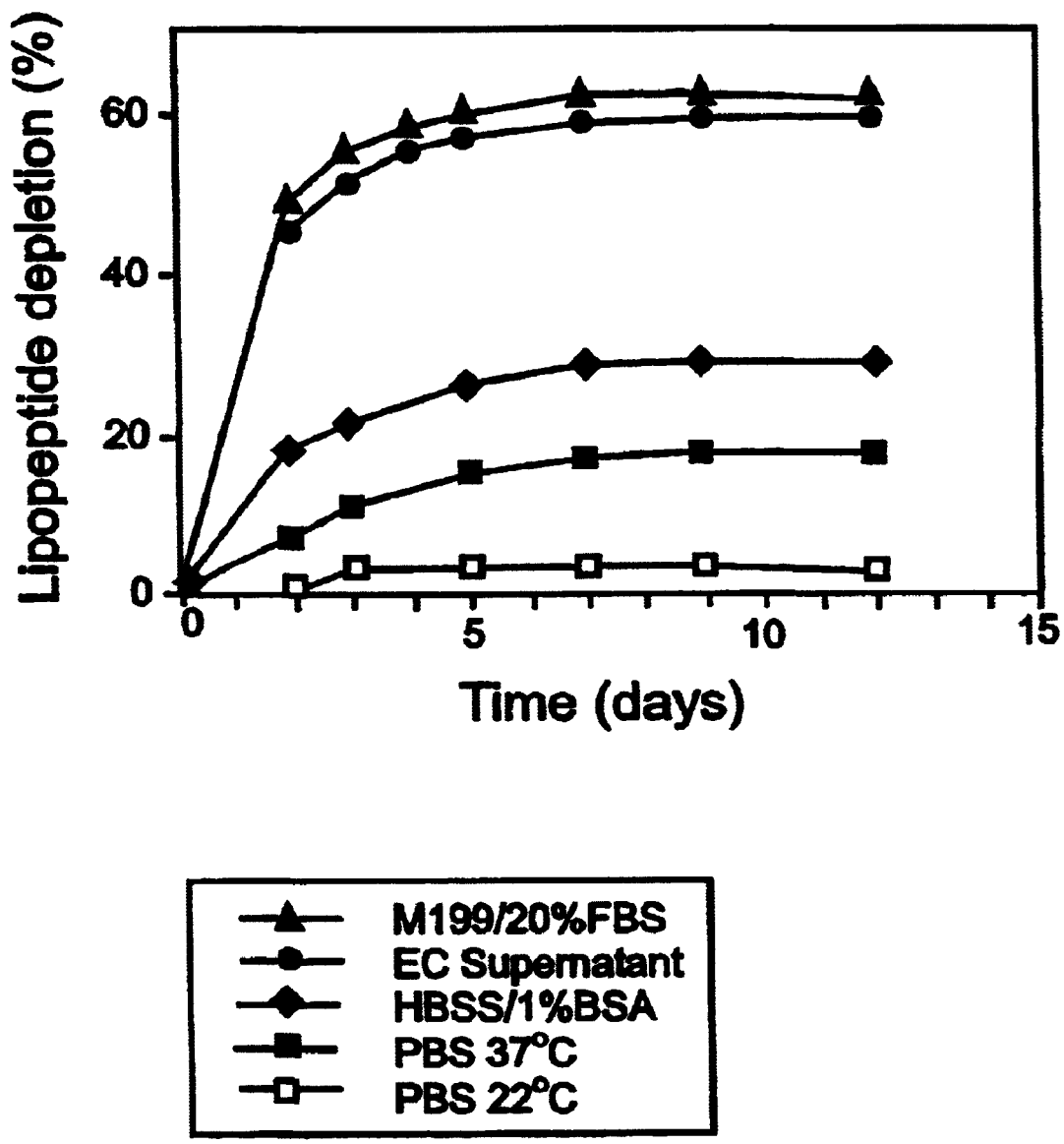
FIG. 7 shows the equilibration of surface lipopeptide concentration as a function of time and environment.

Membrane stability was characterized by measuring surface radioactivity as a fiction of time in diverse biochemical environments. Surfaces were composed of DPPC with 3 mole % of an RGD-derivatized lipopeptide. FIG. 7 demonstrates that when incubated in phosphate buffered saline (PBS) at 22° C. there was a loss of less than 3% of total surface lipopeptide concentration over a 12 day period. At 37° C., lipopeptide loss after an 8 day period approached 18% and was stable thereafter. In the presence of 20% PBS or a supernatant harvested from endothelial cells, only 40% of the initial surface concentration of lipopeptide was present after a 7 day exposure period. Notably, surface composition remained unchanged during an additional 5 days of observation. The plateauing of surface concentration over time in combination with additional HPLC analysis of the constituents suggests that these changes do not represent conjugate degradation per se. Changes in membrane composition may reflect the establishment of new surface equilibrium concentrations as a function of membrane fluidity (i.e. temperature changes), as well as protein binding and exchange reactions at the membrane-liquid interface The effect of membrane-associated cholesterol and lipid chain length have been examined in detail, however, improvement in membrane stability was limited. (Winger, T. M. et al. [1999] *Langmuir* 15:3866.) This work suggests that non-covalently associated assemblies, in and of themselves, are insufficiently robust for medical implant applications. (Winger, T. M. and Chaikof, E. L. [1998] *Langmuir* 14:4148; Mauk, A. et al. [1998] *Langmuir* 14:5255; Winger, T. M. et al. [1999] *Langmuir* 15:3866.)

Example 3

Figure 8:
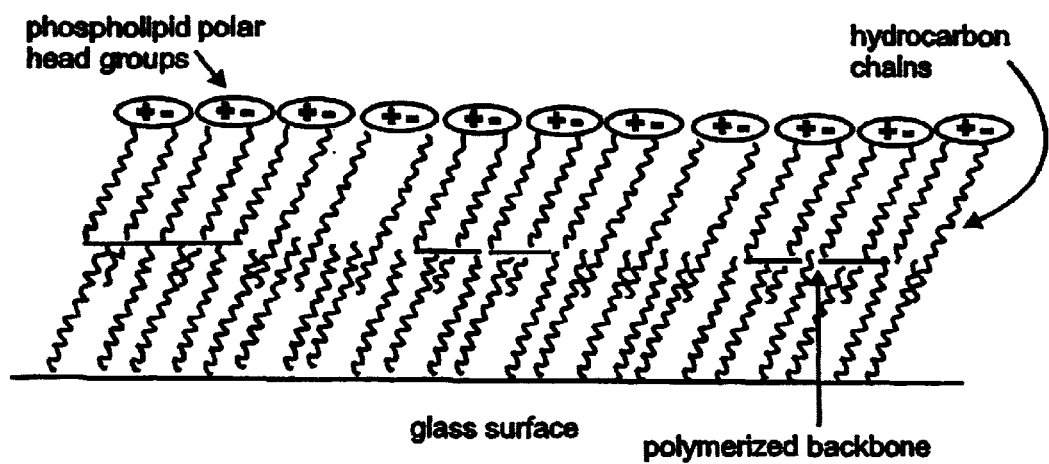
FIG. 8 shows the in situ polymerization of a supported lipid monolayer.

Stabilization of Membrane-mimetic Biomaterials: Polymerization of Lipid Macro-assemblies and Characterization of Blood Contacting Properties In situ polymerization of phospholipids on an alkylated surface. An in situ polymerization strategy was developed using monoacrylate phospholipids as a means of stabilizing a self-assembled lipid monolayer at a solid-liquid interface (FIG. 8). (Marra, K. G. et al. [1997] *Macromolecules* 30:6483-6487.) Phospholipid monomer, 1-palmitoyl-2-(12-(acryloyloxy)dodecanoyl)-sn-glycero-3-phosphorylcholine, was synthesized, prepared as unilamellar vesicles, and fused onto alkylated (OTS) glass. Free-radical polymerization was carried out in aqueous solution at 70° C. using the water-soluble initiator, 2,2'-azobis(2-methylpropionamidine) dihydrochloride (AAPD) (Scheme 2). Under optimized conditions, the supported monolayer displayed advancing and receding water contact angles of 65° and 44°, respectively. Angle-dependent ESCA results confirmed the presence of phosphorus and nitrogen and was consistent with theoretical predictions for close-packed monolayer formation with near-normal alignment of lipid chains. In the absence of network formation, polymeric films demonstrated acceptable stability under static conditions in water and air, as well as in the presence of a high shear flow environment (200 dyn/cm$^2$). This approach provides a route to the generation of stabilized, heterogeneous, biologically active slice structures, which closely mimic the surface of living cells.

Figure 9:
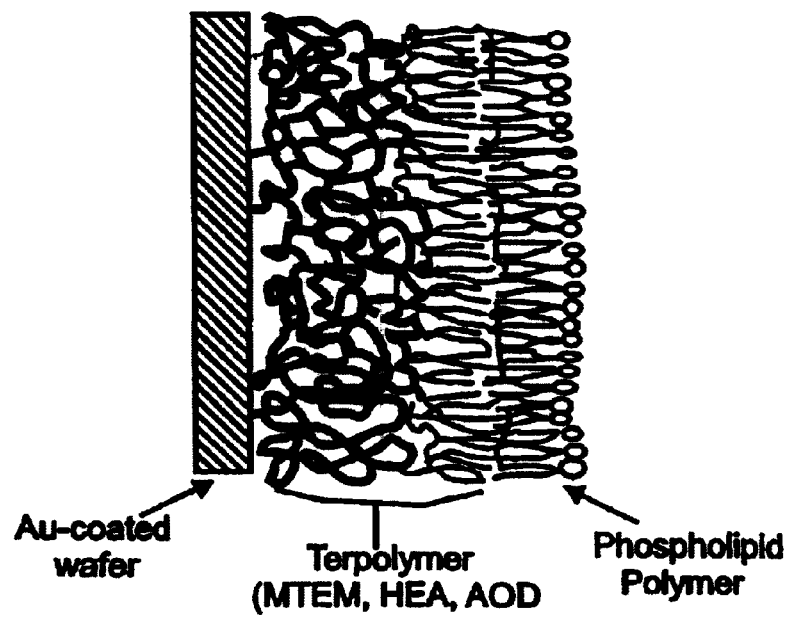
FIG. 9 shows a schematic of a polymerized lipid monolayer on a "mobile" alkylated terpolymer.

In situ polymerization of phospholipids on an alkylated surface supported by a hydrophilic polymeric cushion. Enhancement of 2-D polymerization and film stability. Vesicle fusion and in situ polymerization proceed more efficiently on a molecularly mobile alkylated surface. (Marra, K. C. et al. [1997]*Langmuir* 13:5697-5701.) A terpolymer was synthesized consisting of the monomers 2-hydroxymethyl acrylate (HEA), 3-acryloyl-3-oxapropyl-3-(N,N-dioctadecylcarbamoyl)propionate (AOD), and (methylthio)ethyl methacrylate (MTEM) in a statistical composition of 6:3:1, HEA:AOD:MTEM. The sulfur-containing methacrylate monomer binds to gold as an anchor, whereas the hydrophilic HEA component acts as a "cushion" upon which the hydrophobic dialkylated monomer AOD self-assembles, exposing an ordered layer of C18 chains for vesicle fusion. Formation of a hydrophobic surface on gold-coated silicon wafers was verified by advancing and receding contact angle measurements of 102° and 82°, respectively. As described above, the monoacrylate phospholipid monomer was prepared as unilamellar vesicles, fused onto the terpolymer coated surface, and polymerized (FIG. 9). The supported monolayer displayed advancing and receding water contact angles of 58° and 31°, respectively. Angle-dependent ESCA results confirmed the presence of phosphorus and nitrogen and was consistent with theoretical predictions for a close-packed monolayer. Significantly, contact angle measurements remained unchanged over a several week observation period in water, indicative of a high level of intrinsic film stability. For comparative analysis, the phospholipid was also fused and polymerized onto a relatively "rigid" self-assembled monolayer of octadecyl mercaptan (ODT) bound to gold. ESCA data was consistent with a close packed monolayer, however, contact angle measurements demonstrated that the polymerized He exhibited a higher level of instability over time than that supported by the amphiphilic terpolymer. Therefore, the terpolymer in providing a more flexible surface enhances vesicle fusion and/or the efficiency of in-situ polymerization.

Figure 10:
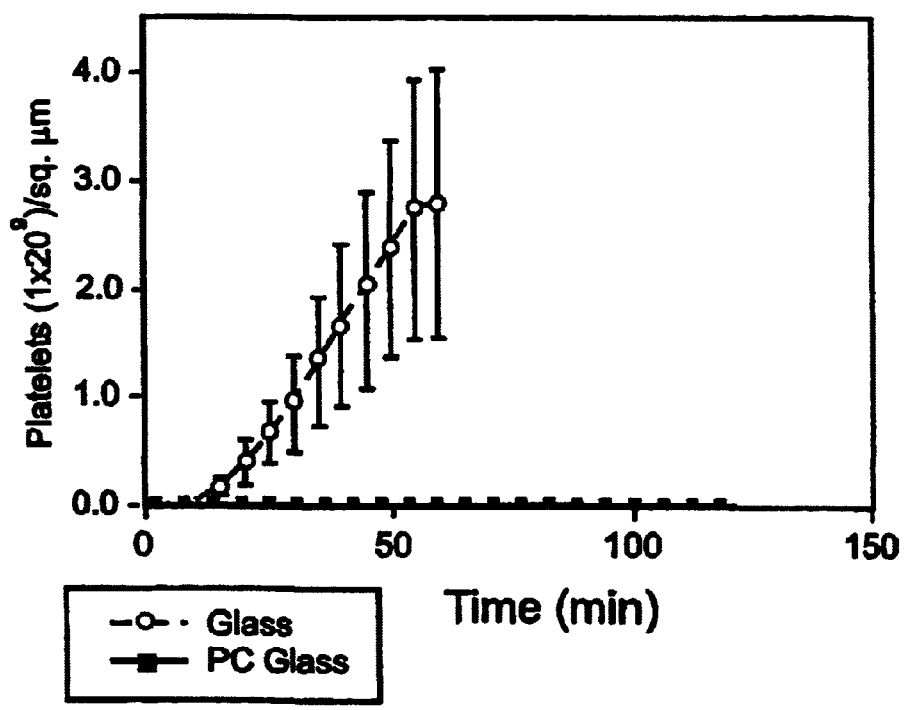
FIG. 10 shows platelet deposition on untreated and PC functionalized glass surfaces in a baboon ex vivo shunt model.

Blood contacting properties of polymerized membrane-mimetic surfaces. Blood compatibility of membrane-mimetic surfaces was assessed in a baboon (*Papio anubis*) arteriovenous shunt model (Marra, K. G. et al. [1997] *Macromolecules* 30:6483-6487.) Glass tubes (4 mm i.d.×3 cm) were alkylated and in-situ phospholipid polymerization performed, as described above. 111-Indium labeled platelet uptake on test surfaces was monitored over a 120-minute period at a flow rate of 100 mL/min using scintillation camera imaging. In contrast to untreated glass surfaces, there was minimal platelet deposition on the PC functionalized surfaces over a two hour period (FIG. 10).

Example 4

Characterization of Endothelial Cell Behavior on Native and Molecularly Engineered Surfaces A functional hybrid vascular bioprosthesis is achievable by identifying and incorporating into a prosthetic scaffold those molecular features which induce selective regenerative responses in preferentially targeted endothelial cells. In this regard, material-induced effects on cell locomotion were a critical determinant in the design process. The data presented in this section demonstrate: (a) EC matrix binding receptors differentially regulate cell adhesion and movement; (b) FGF-2 enhances endothelial random motility by a direct effect on cell speed; and (c) endothelial cell adhesion, migration, and proliferation are supported on substrate bound RGD lipopeptides.

EC matrix binding receptors differentially regulate cell adhesion and movement. To explain how the endothelium regenerates, collaterals form, or the atherosclerotic plaque is neovascularized, recent emphasis has been placed on the extracellular matrix and its ability to control cell adhesion and locomotion. The significance of these investigations with respect to biomaterial design lies in the ability of specific cell surface receptors to ligate distinct peptide sequences in the ECM and, thereby, mediate selective cellular responses. For example, studies have demonstrated that receptors which mediate cell adhesion, may not necessarily be the same as those that control cell movement. (Chon, J. H. et al. [1998*/ Ann. Biomed. Eng.* 26:1091-1101.) In observing the behavior of human aortic endothelial cells on fibronectin coated surfaces, the integrins $\alpha_4\beta_1$, $\alpha_5\beta_1$, and $\alpha_v\beta_3$ all effectively mediated cell adhesion. As anticipated, blockade of $\alpha_4\beta_1$ reduced both absolute cell speed, as well as the proportion of moving cells. However, inhibiting the $\alpha_5\beta_1$ receptor did not effect cell speed but did selectively regulate the commitment of stationary cells to a motile phenotype. Surprisingly, blockade of $\alpha_v\beta_3$ had no effect in limiting cell motility. These findings are of particular interest in the context of Hubbell's observation that $\alpha_4\beta_1$ selectively binds to the fibronectin-derived peptide sequence REDV which appears to mediate the adhesion of endothelial cells, but not platelet, SMCs, or fibroblasts (Massia, S. P. and Hubbell, J. A. [1992] *J. Biol. Chem.* 267:14019-14026; Hubbel, J. A. et al. [1991] *Bio/Technology* 9:568-572.). Data suggests that in addition to its role in modulating cell/substrate adhesive interactions, any matrix, whether natural or synthetic, also establishes a mechanochemical switch which by ligation of specific integrin receptors commits endothelial cells to either a motile or stationary phenotype. A more detailed accounting of EC behavior on native substrates, including SMC monolayers, and their implication for biomaterial design can be found elsewhere. (Chon, J. H. et al. [1998] *Ann. Biomed. Eng.* 26:1091-1101; Chon, J. H. et al. [1997] *J. Surg. Res.* 72:53-59.)

Basic fibroblast growth factor (FGF-2) enhances the chemokinetic responses of human endothelial cells by a direct effect on cell speed. Cyotokines, such as FGF-2, as a component of membrane- or heparan sulfate-mimetic structure enhance EC migration and, as a consequence, facilitate endothelial regeneration. While most reports have demonstrated that FGF-2 increases EC migration in vitro and accelerates re-endothelialization in vivo (Biro, S. et al. [1994] *Circ. Res.* 74:485-494; Lindner, V. et al. [1990] *J. Clin. Invest.* 85:2004-2008; Rifkin, D. B. and Moscatelli, D. [1989] *J. Cell. Biol.* 109:1-6; Sato, Y. and Rifkin, D. B. [1988] *J. Cell. Biol.* 107:1199-1205), others have disputed the ability of FGF-2 to stimulate EC migration (Rosen, E. M. et al. [1991] *J. Cell Physiol.* 146:325-35; Wall, R. T. et al. [1978] *Lab Invest.* 39:523-9; Terranova, V. P. et al. [1985] *Cell Biol.* 101:2330-4). Many of the migration assays used in these investigations, such as in vitro or in vivo wounding, do not easily distinguish between FGF-2 effects on proliferation and migration, which contributes to the conflicting nature of these data. In order to determine, unambiguously, the effect of a uniform concentration of FGF-2 on cell motility single cell video tracking combined with mathematical analysis was performed. Examining the effects of FGF-2 at a single concentration (10 ng/mL), the cell speed increased by 50% (31.9±4.9 vs 19.3±0.7 µm/hr; $p<0.005$) with a corresponding decrease in persistence time (1.46±0.4 vs 1.72±0.27 hr. $p<0.05$). Overall, the random motility coefficient ($\mu$) doubled (742±356 vs 318±69 µm$^2$/hr; $p<0.05$). Thus, even in the absence of a concentration gradient FGF-2 directly augments cell motility in vitro.

Figure 11A:
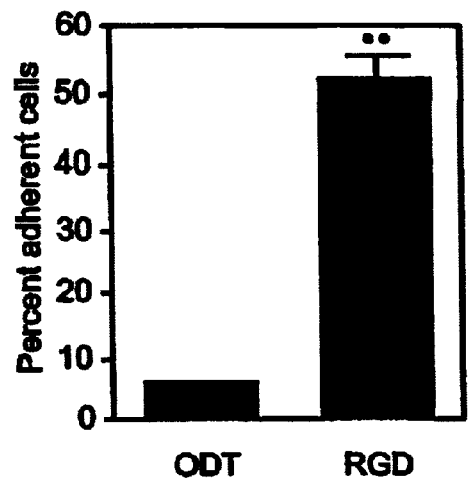
FIG. 11 shows human umbilical vein endothelial cell adhesion (A), migration (B), and proliferation (C) increases on membrane-mimetic substrates.
Figure 11B:
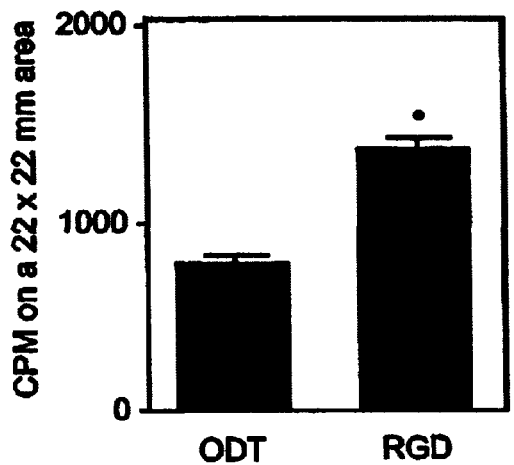
Figure 11C:
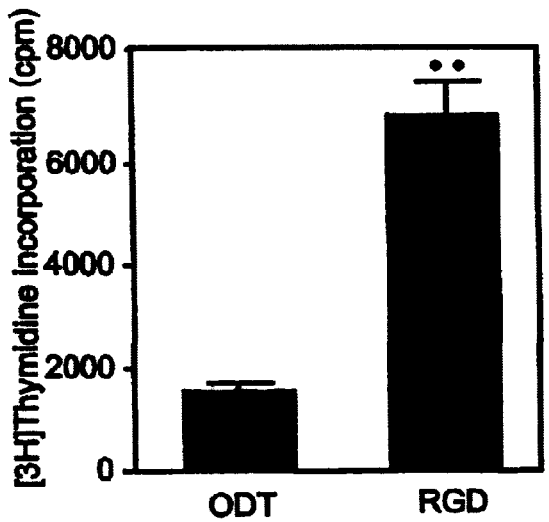

Endothelial cell growth is enhanced on self-assembled RGD lipopeptide bilayers. Endothelial cell adhesion and migration is enhanced on appropriately functionalized lipid surface assemblies (FIG. 11). (Chaikof, E. L. [1996] *Chemtech.* 26:17-24.) Since the RGD peptide sequence is a known ligand for many members of the integrin family of receptors, an RGD lipopeptide conjugate was synthesized, characterized, and substrate supported bilayers formed. To reduce nonspecific effects, all surfaces were blocked by overnight incubation with 1% bovine serum albumin at 4° C. EC adhesion was evaluated after a 2 hour in on period with $^{51}$Cr labeled ECs and migration characterized using a microcarrier assay. In addition, $^3$H-thymidine uptake was used to characterize EC proliferation after 2 days in culture. Cell adhesion, migration, and mitogenesis were significantly greater on RGD containing lipid bilayers when compared with those on alkylated (ODT) gold surfaces. In addition, responses on RGD lipopeptide surfaces were abrogated in the presence of free peptide.

In summary, a variety of lipopeptide and glycolipid conjugates have been synthesized, purified, and characterized. Receptor-specific bioactivity is retained, and molecular assemblies can be formed at both air-water and solid-liquid interfaces. Furthermore, stabilized membrane-like structures are produced with the proper choice of conditions. Such model systems facilitate the study of the structural and dynamic principles involved in the design of biomembrane-mimicking surfaces and identify critical determinants of a membrane-based "on-demand" anticoagulant system.

Example 5

Stabilization of Lipid Assemblies by Visible Light Mediated Photopolymerization

In order to stabilize a planar lipid assembly, a scheme based upon the polymerization of monoacrylate functionalized lipid monomers m the presence of either, AIBN or AAPD, as a free radical initiator is used. Acknowledged limitations of this approach include a requirement to carry out this reaction at 70° C. for periods exceeding 8 hours. Thus, the ability to effectively incorporate proteins or carbohydrate structures into these systems can be limited by their thermal degradation during the polymerization reaction with a consequent reduction in bioactivity. In order to functionalize lipid films with thrombomodulin or other elements that are required for aching an effective membrane-based anticoagulant system, a visible light mediated photopolymer on scheme carried out at room temperature was developed. (Orban, J. and Chaikof, E. L. [2000] *Macromolecules*.) Following the fusion of lipid vesicles with an alkylated substrate, eosin Y and triethanolamine are added as free radical initiator and accelerator, respectively. The molecular assembly is polymerized at room temperature following a 30-minute exposure to a quartz halogen lamp. Average advancing/receding contact angles were 58/420 and are comparable to values obtained by the thermally initiated approach, previously described. Angle-dependent ESCA measurements were carried out to further define atomic level surface properties. In addition, perpendicular and parallel reflectance-absorbance IR spectra were acquired and revealed-that the molecular orientation of hydrocarbon chains in acrylate-PC films was 46.5° relative to the surface normal. Details of these results including stability studies and the use of vibrational spectroscopy to characterize lipid packing and orientation are described in Orban, J. and Chaikof, E. L. (2000) *Macromolecules*. Of note, this strategy increases film stability over that observed using a thermally initiated process through a mechanism related to an increase in molecular chain length, which is achieved when polymerization occurs at a temperature below the transition temperature of the lipid species.

Example 6

Formation of a Membrane-mimetic Lipid Film on Hydrated, Biologically-derived Substrates In situ polymerization of phospholipids on an alkylated hydro gel. The luminal surface of a small diameter vascular graft is functionalized with a membrane-mimetic thin film. Commercially available vascular grafts, fabricated from expanded PIPE or Dacron fibers, are porous textile structures. As such, coating these prostheses is facilitated by their initial impregnation with a substrate amenable to subsequent alkylation and lipid film formation. For example, candidate substrates for graft impregnation include gelatin and/or alginate. In a model study designed to investigate the ability to form a stabilized lipid film on a hydrated substrate, an alginate solution was layered onto a glass slide and gelled following the addition of calcium chloride. (Chon, J. H. et al. [1999] *J. Biomater. Sci. Polymer Ed.* 10:95-108.) A copolymer was synthesized consisting of the monomers 2-hydroxymethyl acrylate (HEA) and 3-acryloyl-3-oxapropyl-3-(N,N-diocta-decylcarbamoyl)propionate (AOD) in a statistical composition of 1:1, HEA:AOD. The alginate was exposed to the copolymer solution, dried, and rehydrated. It was postulated that in the process of water desorption from the gel surface, the hydrophilic HEA component would become entangled within the alginate chains, anchoring the copolymer, and allowing the hydrophobic dialkylated monomers to self-assemble at the solid-air interface. Formation of a hydrophobic surface on the rehydrated polysaccharide gel was verified by advancing and receding contact angle measurements of 94±5° and 63±7°, respectively. Unilamellar vesicles consisting of the monoacrylate phospholipid monomer were prepared and fused onto the copolymer coated surface. Free-radical polymerization was carried out in aqueous solution using AAPD. The supported lipid monolayer displayed advancing and receding water contact angles of 47±8° and 26±7°, respectively. ESCA results confirmed the presence of a lipid film. Contact angle measurements remained unchanged over a several week observation period under static conditions in water indicative of a high level of intrinsic film stability.

Figure 12:
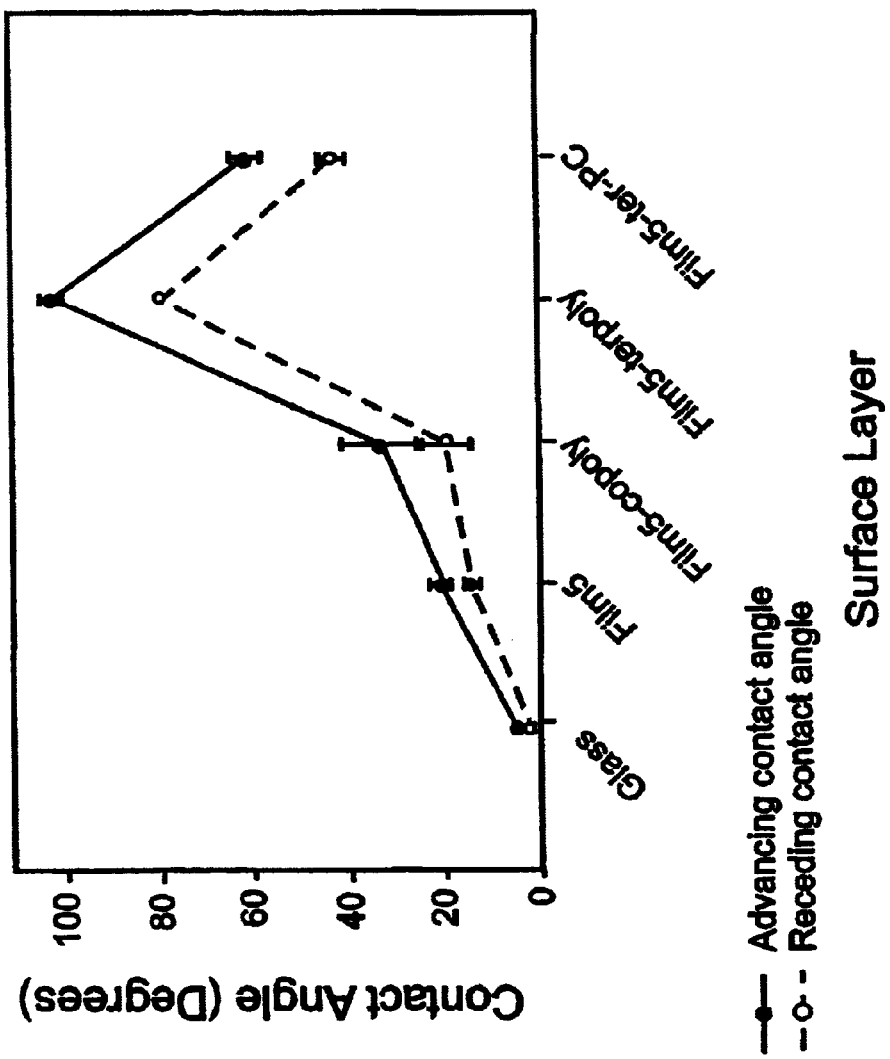
FIG. 12 shows contact angles for serial coating of glass slides: (alginate/PLL)$_5$ (Film 5); (alginate/PLL)$_5$/terpolymer (Film5-terpoly); (alginate/PLL)$_5$/terpolymer/PC (Film5-terpoly-PC). "Copoly" designates HEA:AOD copolymer without sulfonate anchors and demonstrates inability of the polymer to adsorb to PLL.

While coating alginate with an HEA:AOD amphiphilic polymer yielded promising results, several limitations were noted including, reliance on an organic solvent, THF, and vacuum drying to mediate alkylation of the hydrogel. As a consequence, styrene sulfonate was used as a monomer in this copolymer system. The resulting novel alkylated polyelectrolyte is composed of HEA, AOD, and styrene sulfonate in a molar ratio of 6:3:1. This terpolymer carries negatively charged sulfonate ($SO_3$) groups that serve to anchor this polymer to positively charged substrates; such as poly-L-lysine (PLL) (Scheme 3). The capacity to form membrane-mimetic films without the requirement for organic solvents or prolonged vacuum drying was demonstrated using substrates consisting of alginate/PLL multilayers. A multi-layer of alginate Kelco; 0.15% w/v in PBS) and PLL (459 kD; 0.1% w/v in PBS) was generated on glass slides by submerging test surfaces for 30 seconds of contact time in each solution. (PLL-alg)n-PLL films were subsequently incubated with a solution of the polyelectrolyte terpolymer in tri(ethylene glycol) (TEG) at a concentration of 1 mM of sulfonate for 4 to 6 h. Vesicle fusion and visible light mediated photopolymerization were performed as described above. Surface analysis including, contact angle goniometry, ESCA, ellipsometry, and high resolution scanning electron microscopy have been performed and confirmed lipid film formation (FIG. 12). Stability of these systems following incubation in PBS for periods exceeding one month has also been confirmed. Of note, stable multilayers of alginate and poly-L-lysine can be produced on a variety of hydrated biologically derived substrates including gelatin, which carries a net positive charge at physiologic Ph.

Formation of a membrane-mimetic lipid film on the luminal surface of an ePTFE vascular graft. The techniques described above have been utilized to coat the luminal surface of PTFE grafts (4 mm id) with a polymerized monoacryl PC membrane-mimetic thin film. PTFE grafts were initially impregnated with an aqueous solution of gelatin (6 wt %) followed by the coating of the luminal surface with a series of five alternating layers of alginate (0.15 wt % in PBS) and poly-L-lysine (0.10 wt % in PBS). Coating was performed by serial perfusion of the prosthesis at a flow rate of 1 mL/min for 30 seconds. After each perfusion, the prosthesis was with deionized water at 1 mL/min. The luminal surface was then perfused with a 1 mM solution of the HEA:AOD:SS terpolymer in TEG at a flow rate of 1 mL/h for 1 hour followed by a 1 hour perfusion of the surface with TEG at 1 mL/h. A 1.2 mM solution of 600 nm monoacrylPC vesicles was prepared in 20 mM sodium phosphate buffer (pH 7.4), containing 150 mM NaCl and a 10:1 molar ratio of monoacrylPC to Eosin Y. The vesicle solution was perfused through the prosthesis at a flow rate of 1 mL/h for 3 hours and then irradiated for 30 minutes using a quartz halogen lamp. High resolution SEM images were obtained in all cases after vacuum drying and coating with chromium. Vesicle fusion and polymerization generates a stable uniform membrane-mimetic coating on the graft surface. At high magnification, fused vesicles are noted on the luminal surface.

In summary, modification of a gelatin-alginate/PLL)n coacervate with a membrane-mimetic thin film has been successfully performed by the design of an amphiphilic polymer with dialkyl side chains, flexible spacer groups, and anionic substituents which anchor the polymer to a cationic surface. After lipid vesicle fusion to the alkylated hydrogel, the lipid assembly is stabilized via in situ photopolymerization. Film structure and morphology has been characterized using a variety of surface sensitive techniques. Film stability for up to four weeks in PBS has been confirmed.

Example 7

Reconstitution of Thrombomodulin into Membrane-mimetic Lipid Assemblies

Rabbit TM was reconstituted into unilamellar phospholipid vesicles vying in mole ratio of POPC to monoacrylPC (AcPC). The incorporation efficiency of TM exceeded 95% as determined by sucrose gradient. Vesicles were exposed to visible light for varying periods of time in the presence of eosin Y/triethanolamine. Previous studies have demonstrated that total TM concentration, as determined by measuring Gla-domainless protein C (GD-PC) activity after detergent solubilization of lipid vesicles, is in excellent agreement with those values obtained by use of 125-I labeled TM: (Galvin, J. B. et al. [1987] *J. Biol. Chem.* 262(5):2199-2205.) Gla-domainless protein C is obtained by the proteolytic cleavage of the y-carboxyglutamic acid (Gla) containing domain localized to residues 1-41. (Esmon, N. L. et al. [1983] *J. Biol. Chem.* 258[9]:5548-5553.) This domain is responsible for optimal protein C activation by providing an anchor for protein C binding to cell membranes. (Kalafatis, M. et al. [1996] *Critical Reviews in Eukaryotic Gene Expression* 6[1]:87-101.) It has also been demonstrated that Gla-domainless protein C activity can be used to assess the concentration of functionally active TM, appropriately oriented such that the catalytic site is positioned above the outer surface of the lipid vesicle. (Galvin, J. B. et al. [1987] *J. Biol. Chem.* 262(5): 2199-2205.) Reported vesicle concentrations of TM are based upon the measurement of the GD-PC activation rate.

Figure 13:
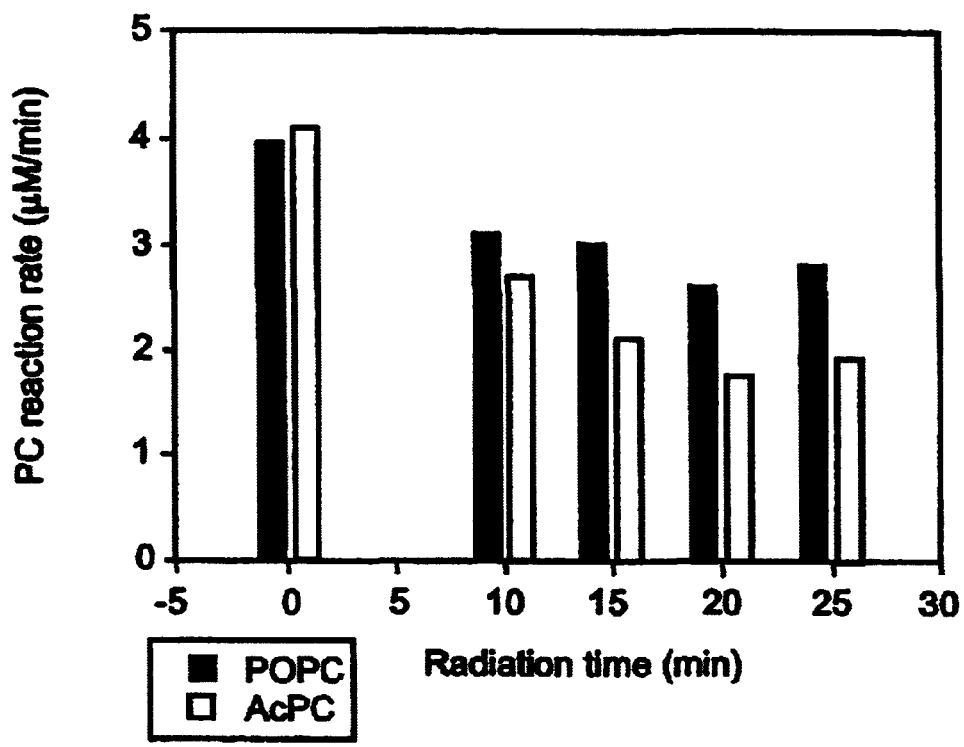
FIG. 13 shows the effect of photopolymerization time on protein C activation rate. TM was incorporated at a surface concentration of 1 nM into either POPC or AcPC vesicles. This represents a molar ration of TM:PC of 1:800,000.
Figure 14:
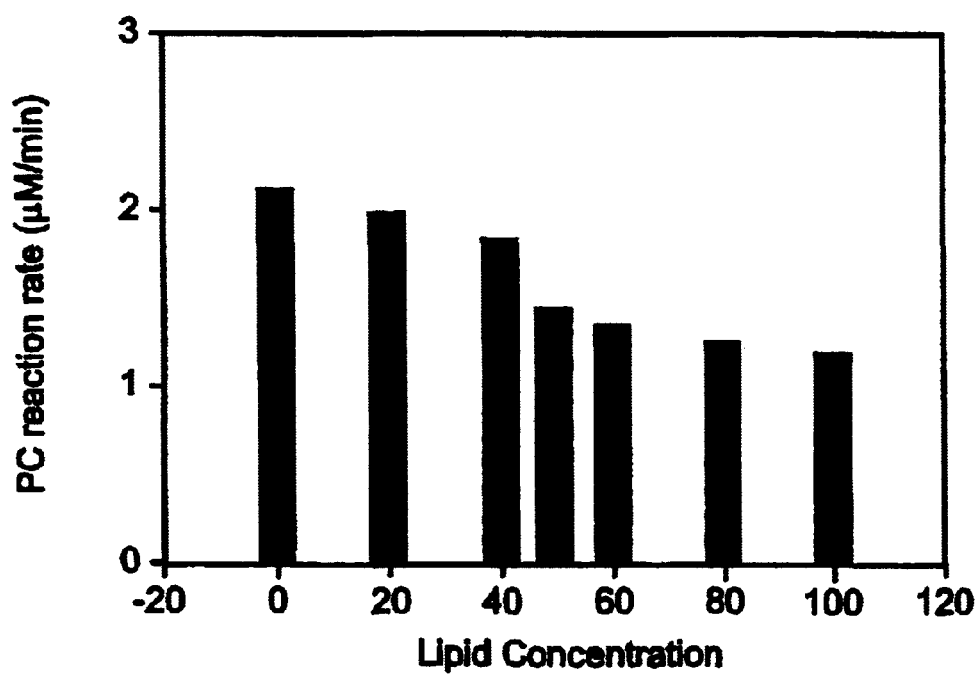
FIG. 14 shows the effect of lipid composition on the APC rate. TM was incorporated at a surface concentration of 1 nM into mixed POPC/AcPC vesicles. The photopolymerization period was 30 minutes.

All vesicle systems, irrespective of lipid composition (POPC vs AcPC), exhibited similar rates of protein C activation prior to polymerization. However, following photopolymerization a modest reduction in the PC activation rate was noted (FIG. 13). This effect may be attributed to two factors. In part, a reduction of TM activity was probably related to direct inactivation of a proportion of TM molecules by free radicals generated during the polymerization process. In addition, the catalytic efficiency was also diminished as a consequence of reduced lipid mobility within the membrane complex. This is supported by the observation that the reduction of catalytic activity was greater when TM was incorporated into vesicles composed of increasing concentration of polymerizable lipids (FIG. 14).

Kinetic parameters, $k_{cat}$ and Km, were obtained by non-linear regression analysis of observed rates of APC production as a function of protein C concentration (Table 1). As anticipated, free TM has a significantly higher Km value compared to TM incorporated into POPC or non-polymerized AcPC vesicles. However, the Km value for TM in polymerized AcPC is much higher than that observed prior to polymerization, indicating that the mobility of TM in the lipid bilayer influences the formation of the protein C activating complex. The $k_{cat}$ values for all four forms are similar and indicate, as anticipated, that the catalytic reaction mechanism remains unchanged. The $k_{cat}$/Km values reveals that protein C activation is catalytically efficient in polymeric vesicles, despite a modest increase in Km.

Example 8

Membrane-mimetic Films Containing TM in an Appropriate Transmembrane Orientation can be Produced by a Process of Molecular Self-assembly and In situ Polymerization Model membrane-mimetic surfaces containing TM can be produced on planar alkylated substrates formed on glass, gold, or silicon substrates depending upon assay requirements. The formation of membrane-mimetic surfaces involve surface fusion of unilamellar phospholipid vesicles followed by in situ photopolymerization and has been described in detail. Recent studies suggest that protein C prefers binding onto lipid membranes that contain both phosphatidylcholine and phosphatidylethanolamine. (Smirnov, M. D. et al. [1999] *Biochemistry* 38[12]:3591-3598; Smirnov, M. D. and Esmon, C. T. [1994] *J. Biol. Chem.* 269[2]:816-819.) Moreover, the PE headgroup may also contribute to the catalytic efficiency of APC, particularly with respect to factor Va inactivation. Therefore, one can analyze the effect of adding TM at different molar concentrations to a baseline DPPC surface (1:10^4-1:10^6) and, secondly, characterize surfaces composed of different molar ratios of phosphatidylcholine and phosphatidylethanolamine phospholipids (0-50 mol %) at a single TM concentration. Finally, the ability to generate stable surface microdomains with locally enhanced membrane dynamics is examined by utilizing mixed assemblies comprised of both polymerizable (e.g., mono-acrylate DPPC) and nonpolymerizable lipids (e.g., DPPC). This allows determination of the effect of generated "molecularly-mobile" microdomains on membrane anticoagulant properties.

Morphological, structural, and chemical properties of substrate supported films are investigated by techniques including contact angle goniometry, ESCA, external reflectance IR and Raman spectroscopy, as well as by high resolution SEM and AFM. Membrane dynamics are studied using fluorescence recovery after photobleaching (FRAP) techniques coupled with confocal fluorescence microscopy. In the process, the molecular diffusivities of fluorescently tagged lipids and TM as a function of alkylated substrate type (HEA:AOD: MTEM vs HEA.AOD.SS), lipid microenvironment (PC vs PE), and extent of 2-D polymerization (% AcPC) are determined. Effective TM surface concentration is determined by measuring Gla domainless-protein C (GD-PC) activation. Surface concentrations are compared to those determined for TM containing lipid vesicles in order to assess reorientation of TM within planar lipid films upon vesicle fusion to alkylated test substrates,

Example 9

Although lipid membranes composed of phosphatidylcholine head groups reportedly do not initiate contact activation, most artificial surfaces, including heparinized material do activate the intrinsic pathway of the coagulation system. (Blezer, R. et al. [1998] *Thromb. Hematosis* 79[2]:296-301.) In order to determine if TM containing membrane-mimetic films initiate blood coagulation, two test systems are utilized—supported lipid films and polymeric lipid vesicles.

Supported lipid films are produced on circular glass cover slips (d 20 mm), placed in multiwell plates, and exposed to citrated platelet-free human plasma Clotting is initiated by the addition of calcium to a total concentration of 4 mM. Samples are taken from the reaction mixture over a 90 minute interval and assayed for factor XIa, IXa, Xa, and thrombin production, as well as the generation of APC. The effect of surface induced protein C activation is determined by selectively repeating these investigations using protein C-depleted plasma (George King Biomedical, Overland Park, Kans.). As a second experimental system various concentrations of polymeric lipid vesicles are substituted for planar glass coated surfaces in order to maximize test surface area. Factor XIa, IXa, Xa, and thrombin activity, as well as APC levels are measured after recalcification of citrated platelet-free human plasma. Given vesicle dimensions, as determined by quasi-elastic light scattering, total phospholipid concentration, and published dimensions for head group surface area, the total vesicle concentration and exposed membrane surface area are determined.

The role of antithrombin III in limiting the activation of blood coagulation by TM-containing membrane-mimetic assemblies is determined by pretreating selective test surfaces with chondroitinase in order to remove TM-associated chondroitin sulfate chains. In an initial series of experiments ATIII-binding capacity is defined by exposing test surfaces to a 500 nM solution of I125-labeled ATIII, as described in detail elsewhere. (Blezer, R. et al. [1997] *J. Biomed. Mater. Res.* 37[1]:108-113.) Polymeric lipid vesicles are used to maximize test surface area and a sucrose gradient is used to determine the association of I125-labeled ATIII with test vesicles. A second series of experiments defines the catalytic activity of surface-bound chondroitin sulfate chains with regards to thrombin neutralization. Test samples are exposed to Hepes buffer containing 15 nM of thrombin and 20 nM of antithrombin. At timed intervals, samples are removed and assayed for residual thrombin activity and thrombin-antithrombin III (TAT) complex formation. TAT formation is determined by ELISA (Enzygnost TAT, Behring, Marburg, Germany).

Example 10

In order to determine the role of TM containing lipid assemblies in limiting the propagation phase of blood coagulation, test surfaces are exposed to citrated platelet free human plasma spiked with 20/LM unilamellar vesicles composed of 25 mol % DOPS/75 mol % DOPC. (Blezer, R. et al. [1997] *J. Biomed. Mater. Res.* 37[1]:108-113.) These vesicles are utilized to mimic the lipid composition of procoagulant platelet phospholipid membranes, thereby facilitating the assembly of the factor X activating complex (tenase). Clotting is initiated by the addition of calcium to a total concentration of 4 mM, samples are taken from the reaction mixture over a 90 minute interval and assayed for factor Xa, activated protein C, and thrombin production. The approximate proportion of thrombin accessible to the procoagulant pathway is determined by measuring fibrinopeptide A formation. Test samples include polymeric lipid vesicles and/or supported planar polymeric lipid films, as described above.

Example 11

The films described above have sufficient biostability for both in vitro and in vivo use. For example, even in non-polymerized forms, liposomes persist for days or even weeks at the site of subcutaneous injection. (Mauk, M. R. et al. [1980] *Science* 207:309-311.) Other studies have also determined that surfaces modified with a variety of biomacromolecules retain molecule specific bioactivity for prolonged periods in vitro and in vivo. (Imanshi, Y. [1992] "Synthesis of biocomposite materials: Chemical and biological modifications of natural polymers," Boca Raton, Fla., CRC Press; Nojiri, C. et al. [1996] *ASAIO Journal* 42[5]-M468-475.) Nonetheless, phospholipids, proteins, and carbohydrates will inevitably degrade as a consequence of the action of endogenous peptidases, glycosidases, and hydrolases. Thus, in vitro experiments are used to define the biostability of TM-functionalized polymeric lipid membranes. Specifically, biological and physiochemical film stability is evaluated in two sets of experiments:

The Effect of Physical Factors on Membrane Stability. Film stability is initially assessed by incubation of samples in PBS and citrated human plasma at 23 and 37° C. In all cases, changes in TM surface concentration is determined by measuring the GD-PC activation rate. The use of additional surface sensitive techniques to assess changes in film physical and chemical properties are performed on a selective basis. These studies determine if there is significant loss of TM activity through direct desorption or due to the effect of binding interactions with serum proteins or naturally occurring surfactant molecules. Finally, in most clinical applications, blood contacting surfaces will be subjected to wall shear rates of 20 dyn/cm$^2$ or less. Therefore, films are also analyzed after PBS exposure to a continuous shear stress (20 and 200 dyn/cm$^2$) for up to 120 minutes in a parallel plate flow chamber.

The effect of biochemical factors on membrane stability. Test surfaces are incubated in the presence of endothelial cells using a dual chamber culture system (Falcon, Inc.) consisting of a 24-well plate fitted with porous inserts (0.45 µm pore size). Endothelial cells are cultured in the insert and test substrates placed in the underlying well. Replacement of the well insert with newly cultured endothelial cells may be required depending on the duration of the experiment. At various time intervals (0, 24 h, 48 h, 96 h, 1 wk, 2 wk and 4 wk), test substrates are removed and changes in TM surface concentration determined by measuring the GD-PC activation rate. Incubation of the samples in PBS alone or PBS with phospholipase C at a weight ratio of lipase to lipid of 1:20, 1:100, and 1:1000, serves as negative and positive controls, respectively. The use of additional surface sensitive techniques to assess changes in film physical and chemical properties are performed on a selective basis.

Example 12

The investigations in this section seek to: (i) define a kinetically limited regime for APC production at venous (50 sec$^{-1}$) and arterial flow rates (500 sec$^{-1}$); (ii) determine the intrinsic kinetic parameters for APC production and the effect on these parameters of shear rate, lipid head group composition, and membrane dynamics; and (iii) identify whether the rate of formation of the protein C-activating complex is a diffusion or reaction controlled process. The methodological approach is based on the use of a capillary tube flow reactor system, as detailed elsewhere. (Blezer, R. et al. [1998] *Thromb. Haemostasis* 79[2]:296-301; Billy, D. et al. [1995] *J. Biol. Chem.* 270[3]:1029-1034; Contino, P. B. et al. [1994] *Biophys. J.* 67[3]:1113-1116.) This technique has been used extensively in studying the effect of flow rates on lipid membrane based processes. A glass capillary tube (0.65 mm id and 127 mm length) is coated with a membrane-mimetic film and attached to a Hamilton syringe. The flow rate of the test solution is controlled by a syringe pump and timed samples collected from the tip of the flow reactor. All studies are conducted at 37° C. In addition to photopolymerized lipid films, TM is incorporated into vesicles comprised of non-acrylate containing lipid molecules (e.g. POPC, DL2PE, etc.) for fusion onto the inner wall of glass capillary tubes. The reconstitution of TM into a lipid coating comprised of native phospholipids serves as a reference point for all studies outlined below. The data generated using this reference system most closely mimics the true microenvironment of the cell membrane.

Experiments to define a kinetically limited regime for APC production involve the perfusion of coated capillaries with activation buffer (20 mM Tris-HCl pH 5.5) containing 100 mM NaCl, 5 mg/mL BSA, 5 mM Ca$^{2+}$, protein C (0.1/LM), and thrombin (10 nM). APC production is determined as a function of TM surface density at venous and arterial shear rates. Transport limitations have a significant impact on the behavior of these systems. Therefore, these experiments help define, for a given flow regime, a TM surface density above which APC production becomes independent of TM concentration due to mass transfer limitations.

The intrinsic kinetic parameters for APC production are assessed in a kinetically limited regime by perfusion of coated capillary tubes with activation buffer containing thrombin (10 nM) with varying concentrations of protein C (0.01-4 µM). In all cases, capillary tubes are preperfused with thrombin alone for 10 min. Rates of APC production are determined from the steady state levels of APC measured at the outlet of the flow reactor. Kinetic parameters, $k_{cat}$ and Km, are obtained by non-linear regression analysis of observed rates of APC production as a function of protein C concentration in the perfusion solution. The effect on these parameters of shear rates (50 sec$^{-1}$ vs. 500 sec$^{-1}$) and lipid head group composition (i.e. varying molar ratios of phosphatidylcholine to phosphatidylethanolaxnine) is determined. In addition, kinetic parameters are defined for mixed membrane-mimetic assemblies comprised of polymeric and non-polymeric lipids if these systems are sufficiently stable. Finally, kinetic parameters are compared to those values reported for TM complexes inserted into POPC vesicles, as well as to those derived for TM complexes inserted into lipid vesicles composed all, or in part, of polymeric lipids.

The rate of formation of the protein C-activating complex (i.e., TM:thrombin) is estimated under arterial and venous flow conditions and defined as a diffusion or reaction controlled process. Membrane coated capillary tubes are perfused with activation buffer containing protein C (0.1 µM) and varying amounts of thrombin (0.1-10 nM) and APC production measured at the reactor outlet. The time to reach steady state levels of APC production decreases with increasing amounts of thrombin in the perfusion solution. The initial part of the APC generation curve, therefore, reflects the rate of formation of APC generating activity at the membrane-mimetic surface, and this rate increases with increasing amounts of thrombin in the perfusion mixture. The experimental rate of APC production is compared to the calculated rate of thrombin mass transfer to the catalytic surface in order to determine whether the formation of the protein C activating complex is a transport or kinetically limited process.

Example 13

These experiments examine the antithrombogenic properties of TM containing membrane-mimetic films under arterial (500 sec$^{-1}$) and venous (50 sec$^{-1}$) flow conditions. In the process, the capacity of test films to limit thrombin formation, if initiated by either activation of the intrinsic or extrinsic pathways of the coagulation cascade, is defined. In addition, the extent to which thrombin is either inactivated or directed into the protein C pathway is determined. As described above, the methodological approach in all of these studies utilize a capillary tube flow reactor system. Recalcification of citrated-platelet free human plasma or the addition of other initiators of the coagulation cascade, such as thrombin or tissue factor, occur by mixing these factors into the perfusate just before entrance into the flow reactor. All studies are conducted at 37° C.

Experiments to define the ability of membrane-mimetic films to limit the propagation of blood coagulation when initiated via the intrinsic pathway involve the perfusion of coated capillaries with recalcified platelet free human plasma. Samples are collected from the outlet of the flow reactor and assayed for factor XIa, IXa, Xa, APC, and thrombin production. The effect of surface-induced protein C activation in this process is determined by measuring clotting factor activation in the presence of TM-free membrane systems. In order to potentiate the propagation of blood coagulation, experiments are selectively repeated with recalcified platelet-free human plasma spiked with 20 µM of unilamellar vesicles composed of 25 mol % DOPS/75 mol % DOPC. These vesicles mimic the lipid composition of procoagulant platelet phospholipid membranes and facilitate the assembly of the factor X activating complex (tenase).

In the second phase of these studies, experiments are conducted to define the ability of membrane-mimetic films to limit blood coagulation when initiated via the extrinsic pathway. These investigations involve the perfusion of coated capillaries with recalcified platelet free plasma spiked with varying concentrations of tissue factor (1-100 pM) reconstituted into unilamellar vesicles composed of 25 mol % DOPS/ 75 mol % DOPC. Samples at the flow reactor outlet are collected and assayed for factor Xa, APC, and thrombin production. The approximate proportion of thrombin accessible to the procoagulant pathway is determined by measuring fibrinopeptide A formation. The effect of surface-induced protein C activation is determined by measuring clotting factor activation in the presence of TM-free membrane systems.

In order to estimate the rate of formation of direct thrombin inactivation complexes (TM:ATIII), coated capillary tubes are perfused with Hepes buffer containing 15 nM of thrombin and 20 nM of antithrombin. At timed intervals samples are collected and assayed for residual thrombin activity and thrombin-antithrombin III (TAT) complex formation. Thrombin inactivation activity is compared to the known ATIII binding capacity of the membrane as previously determined.

Another series of experiments is directed at examining antithrombogenic film properties in the presence of thrombin-containing human plasma. Coated capillaries are perfused with recalcified platelet free plasma spiked with varying concentrations of thrombin (10-100 nM). Samples at the flow reactor outlet are collected and assayed for factor Xa, APC, thrombin, and fibrinopeptide A formation.

Example 14

Composite prostheses are fabricated by first impregnating the graft wall (6 mm id ePTFE) with gelatin followed by coating of the luminal surface of the prosthesis with alternating polyelectrolyte layers of alginate and poly-L-lysine. Subsequent formation of an alkylated layer on the luminal surface of the prosthesis is achieved using an amphiphilic terpolymer. The prosthesis is then be incubated with an aqueous mixture of lipid vesicles followed by in situ polymerization of the self-assembled lipid membrane. Surface characterization is performed using ESCA, contact angle goniometry, high resolution SEM, and surface TM concentration measured by the GD-PC activation assay. Uniformity of film coating is determined using chromophore labeled lipid probes combined with epifluorescent microscopy.

The limitations of short-term blood contacting studies in predicting the risk of surface-induced thrombosis are well known. Nonetheless, characterization of the performance of these materials using acute blood-contacting assays provides a convenient screening mechanism for a large array of surface compositions. A baboon ex vivo Lame femoral arteriovenous shunt model is used to evaluate acute platelet and fibrinogen deposition in well-defined flow regimes. A test sample is placed in the shunt and exposed to $^{111}$In labeled platelets for up to 120 minutes at a wall shear rate of either 50 sec$^{-1}$ or 500 sec$^{-1}$. Platelet deposition is monitored by scintillation camera imaging. Adsorption of injected $^{125}$I labeled fibrinogen is determined at the end of the blood exposure period by gamma counting. Using $^{125}$I labeled fibrinogen, as a marker of plasma protein adsorption, investigates whether platelets adhere to and are activated by the primary surface or via an adsorbed plasma protein\fibrin film. Several in vivo plasma assays of markers, which are elevated upon activation of platelets and coagulation enzymes, are also utilized during the course of these studies. Specifically, consumption of fibrinogen and its cleavage by thrombin is assessed by measurements of plasma clottable fibrinogen and fibrinopeptide A (FPA) levels. Activation of platelets is judged from the change in circulating platelet count and by plasma levels of the releasable platelet α-granule proteins, β-thromboglobulin and platelet factor 4. Fibrinolysis is estimated by measurement of circulating levels of fibrin D-dimer fragment. Activated partial thromboplastin time (APTT) measurements are also performed using citrated plasma samples. Significantly, the degree of surface-induced thrombin formation is determined by measuring levels of thrombin-antithrombin III complexes. The utilization of these assays by in a baboon shunt model have been described in detail elsewhere. (Hanson, S. R. et al. [1993] *J. Clin. Invest.* 92[4]:2003-2012.) Finally, use of radiolabeled or chromophore-labeled conjugates within the lipid film allows characterization of short-term biostability in a blood-contacting environment. The requirement for a membrane-mimetic film lining the luminal surface of a small caliber graft is tested by assessing platelet and protein deposition on uncoated grafts, as well as those coated with alginate/PLL or alginate/ PLliter polymer alone.

Associated methodologies with this animal model have been described in further detail. (Marra, K. C. [1997] *Macromolecules* 30:6483-6487; Golden, M. A. [1990] *J. Vascular Surgery* 11[6]:838-844; Hanson, S. R. [1993] *J. Clin. Invest.* 92[4]:2003-2012; Hanson, S. R. et al. [1985] *Arteriosclerosis* 5:595-603; Clowes, A. W. et al. [1985] *Am. J. Pathol.* 118[1]: 43-54.) Multiple ex vivo shunts may be performed in a single animal, as many as 10-15 shunt studies can be tolerated in a given baboon. By thorough use of prior in vitro studies, the number of animals required is minimized without compromising the validity of the results. All studies are conducted with human TM and protein C. To date, a high degree of sequence homology (>98%) has been determined between human and baboon cDNA species encoding for a variety proteins. (Hayzer, D. et al. [1993] *Gene* 127:271-271; Shoji, M. et al. [1993] *Gene* 133:307-308; Hayzer, D. et al. [1999] *Thromb. Res.*) Moreover, recombinant human soluble TM is capable of activating protein C and limiting thrombin generation when injected into baboons. (Harker, L. A. et al. [2000] *Circulation.*) Thus, membrane-mimetic films functionalized with human TM are able to activate the endogenous protein C pathway in baboons.

Example 15

For studies conducted under arterial shear rate conditions, prostheses are deployed in the carotid and iliac arteries of a primate model. Using both iliac and carotid arteries for these studies, at least 40 arterial sites (10 animals) are available for concurrent, parallel investigations in selected specimens. Two film compositions are the focus of these investigations: (i) a simple phosphorylcholine phospholipid membrane-like assembly, and (ii) a membrane-mimetic film which contains TM. These different graft formulations are assessed along with an untreated set. The total number arterial sites allows implantation of at least replicates in each group with data analysis using ANOVA and t-tests.

Following a graft implantation, patency is established initially and prior to ice at 30 days or 6 months by Duplex imaging with associated arterial volume flow measurements. These time points are based upon prior studies, which have carefully analyzed ePTFE graft healing in a baboon model. (Golden, M. A. et al. [1990] *J. Vascular Surgery* 11[6]:838-844; Clowes, A. W. et al. [1985] *Am. J. Pathol.* 118[1]:43-54; Clowes, A W et al. [1986] *J. Vasc. Surg.* 3:877-884.) By one month, ingrowth extends approximately 1 cm and a significant anastomatic neointimal lesion is present obstructing about 10% of the graft lumen. These findings have been reproducible; hence, the one-month time point is appropriate for assessing early healing events. Intimal area and the extent of pannus ingrowth increase progressively between 1 and 6 months, with little further change by 12 months. Similarly, the fraction of intima comprised of SMC vs. matrix components decreases out to 6 months, remaining stable thereafter. Therefore, the 6-month time point was chosen for the evaluation of late healing outcome.

Prior to graft harvesting, animals receive intravenous injections of Evans Blue, which enters the graft wall where endothelium is absent and bromodeoxyuridine (BrdU) for measurements of cell proliferation. At the time of explantation, grafts are opened longitudinally and photographed for measurements of thrombus-free surface and overall pannus tissue ingrowth, which in control studies with ePTFE grafts averages about 1 cm/month. Then serial sections are obtained from the adjacent artery and along the entire graft taken at approximately 5-mm intervals for examination by scanning electron microscopy and light microscopy. This approach permits histological reconstruction of healing events over the entire graft length, as previously described. (Hanson, S. R. et al. [1991] *Hypertension* 18[4 Supp]:II70-6.) Staining is performed to examine endothelial and smooth muscle cell coverage, as well as associated arterial wall cellular and matrix responses. For example, immunohistochemical studies include stain with endothelial factor VIII/von Willebrand factor to identify endothelial cells, smooth muscle α-actin to identify smooth muscle cells, and Ham 56 to identify macrophages. Neointimal hyperplasia (i.e. the inner capsule of the graft) is assessed by established quantitative computerized morphometic techniques.

Example 16

Modulation of Molecular Transport by a Membrane-mimetic Surface

Figure 15:
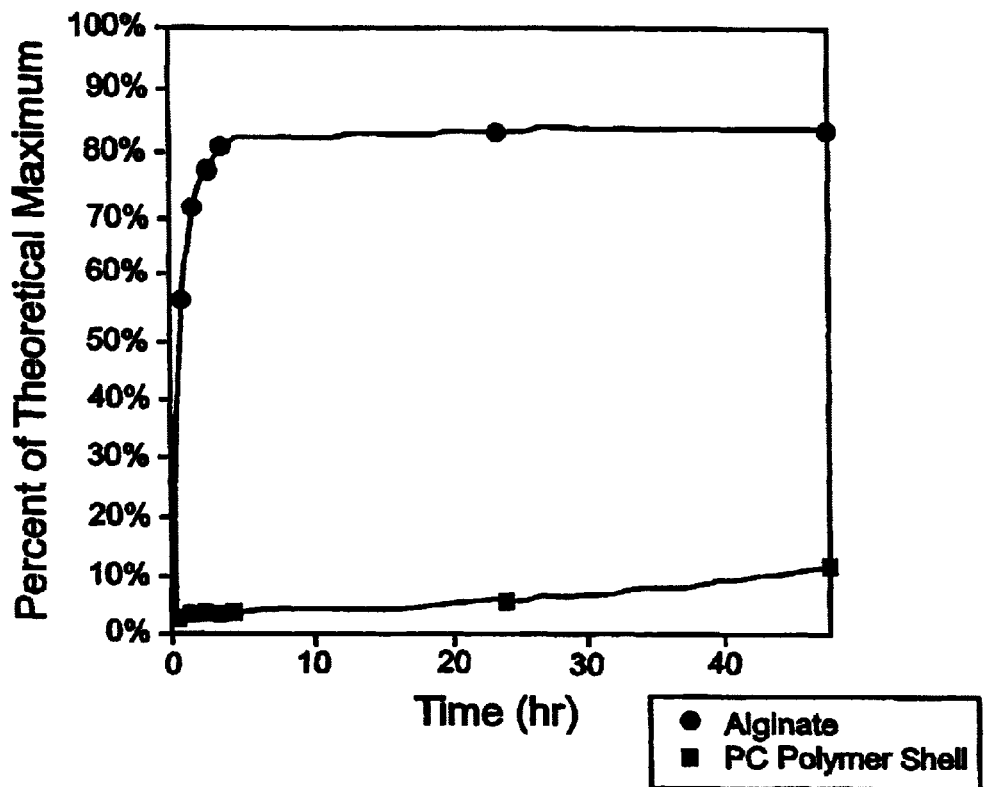
FIG. 15 shows the diffusivity of albumin (MW $6.9 \times 10^4$) from alginate beads prepared with (alginate/(4)/PC) or without (alginate) polymeric membrane-mimetic coating Ct=concentration of BSA in the elution medium at any time, while Ce=concentration of the BSA calculated by mass balance. Ct/Ce is expressed as a percent.

Alteration of mass transport properties at the hydrogel-water interface by a membrane-mimetic coating. Alginate beads (average diameter 2.32 mm) loaded with $^{125}$I bovine serum albumin (10:1 alginate/BSA solution) were coated with a copolymer supported lipid membrane. The beads were incubated at 37° C., samples were taken at regular intervals, and the radioactivity counted to measure the amount of BSA which diffused into the solution. The unsteady-state diffusion of the BSA from a sphere was analyzed as described by Skelland (Skelland, A. H. P. [1974) Diffusional Mass Transfer, New York: John Wiley & Sons) and the overall mass transfer coefficient determined by a procedure similar to that utilized by Crooks et al. (Crooks, C. A. et al. [1990] *J. Biomed. Mater. Res.* 24:1241-1262). BSA transport behavior is presented in FIG. 15. As demonstrated, the presence of a polymerized lipid membrane significantly reduced BSA diffusivity. After 24 hours over 80% of the albumin had been released from uncoated alginate beads. In contrast, approximately 95% of the albumin was retained in coated beads. Specifically, diffusivity of BSA through the alginate/aqueous interface was reduced from $3.42\times10^{-4}$ cm$^2$/hr to $225\times10^{-16}$ cm$^2$/hr by the addition of a membrane-mimetic coating with an assumed film thickness of 125 Å. Similarly, the overall mass transfer coefficient for BSA through polymer coated alginate beads was $4.71\times10^{-9}$ cm/min which was significantly less than that demonstrated by either Matthew et al. (Matthew, H. W. et al. [1993] *Biotechnol. Prog.* 9:510-519) for standard poly-L-lysine-alginate capsules ($1.5\times10^{-4}$ cm/min) or by Crooks et al. (Crooks, C. A. et al. [1990] *J. Biomed. Mater. Res.* 24:1241-1262) for microcapsules composed of a hydroxyethylmethacrylate-methyl methacrylate copolymer ($4.21\times10^{-6}$ cm/min). In the design of an immunoisolation barrier an accepted standard for MWCO does not currently exist. However, these studies demonstrate that an ultra-thin, polymeric membrane-mimetic coating can yield an interface which is impermeable to immunoglobulins.

Interaction of 2nd generation PEO dendrimers with a self-assembled lipid monolayer at an air-water interface. Second generation PEO dendrimers were synthesized as illustrated in Scheme 4 (Mn=52,000 g/mol, Mw=71,000 g/mol, PD=1.3). In order to characterize the mixing properties of PEO dendrimers in a phospholipid monolayer, sure area-pressure isotherms of PEO dendrimer/lipid mixtures at an air/water interface were acquired on a circular LangmuirBlodgett trough (Type 2000, Nima Technology, Coventry, England) at 25° C. PEO dendrimers and dipalmitoyl phosphatidylglycerol (DPPG) were dissolved in choloroform:methanol (4:1 v/v) and spread using an air-tight Hamilton syringe onto an aqueous subphase of 150 mM NaCl solution. (Heroguez, V. et al. [1997] *Macromolecules* 30:4791-98.) Molar ratios of PEO:DPPG ranged from 1:10$^3$ to 1:10$^7$ with pure DPPG included as a reference standard.

Figure 16:
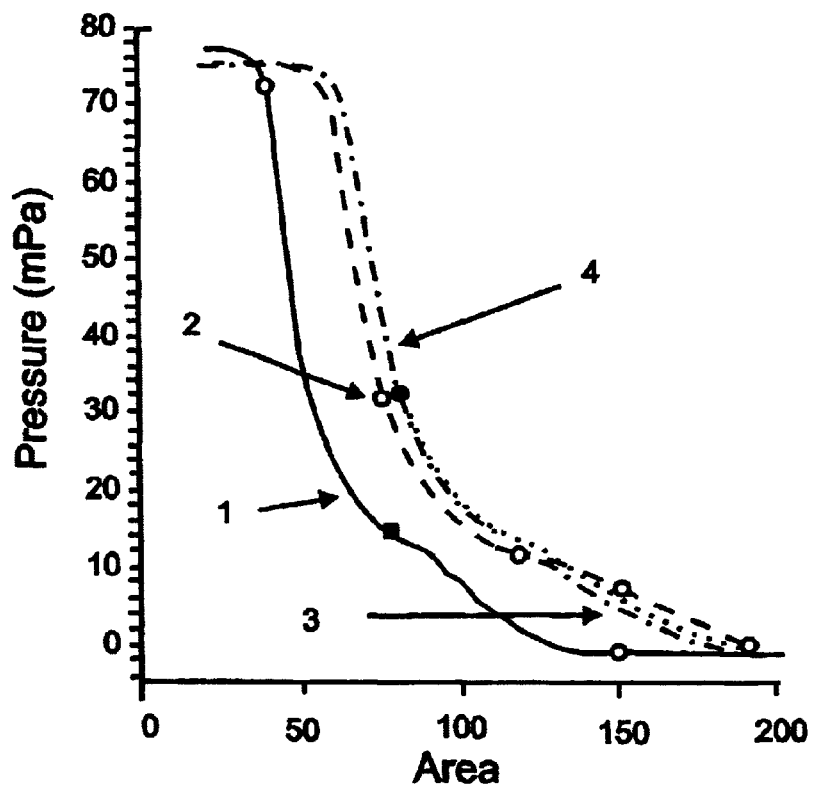
FIG. 16 shows the surface area-pressure isotherms of pure DPPG (1) and of mixed PEO dendrimer/DPPG monolayers: (2) PEO:DPPG $1:10^3$; (3) $1:10^5$; (4) $1:10^7$.

Surface area-pressure isotherms for both mixed systems and DPPG alone featured well-defined expanded and condensed phases (FIG. 16). Compression curves clearly indicate surface incorporation of PEO dendrimers into lipid monolayers with a significant increase in the area per molecule at even relatively low molar concentrations of dendrimer. The transition region between liquid expanded and liquid condensed phases is shifted toward a higher area per molecule due to PEG incorporation in the monolayer. Collapse pressures for both pure DPPG and mixed systems did not differ significantly (75 mN/m), although the area at collapse was larger for dendrimer containing mixtures (70 Å$^2$/molecule vs. 40 Å$^2$/molecule). Of note, the collapse area for DPPG is comparable to the expected value for a dialkyl amphiphile. These data show that PEO dendrimers will readily associate with self-assembled lipid monolayers with relatively little depletion of the dendrimer even at highest surface pressures.

Visualization of individual PEO dendrimer molecules by cryoelectron microscopy. Aqueous PEO dendrimers (Star 594, Shearwater Polymers, Inc, Alabaster, Ala.) with reported relative molecular mass of 405,000, representative of 54 arms of PEO, were characterized by cryoelectron microscopy. The PDI for the PEO dendrimer is greater than 2 with an aqueous phase diameter in the range of 29 nm. (Gnanou, Y et al. [1998] *Makromol. Chem.* 189:2885-2892; Cima, L. G. and Lopin, S. T. [1995] *Macromolecules* 28:6787-6794.) The dendrimer was dissolved in distilled water to a concentration of about 0.2 mg/mL. For cryo-EM experiments in the STEM and SEM modes, two sample preparation methods were utilized. Samples (5 µL) were applied either to: (i) a 3 mm gold specimen carrier with a flat surface (BUOI2 128-T), followed by submersion into liquid ethane (–186° C.), and freeze fracturing; or (ii) a commercially available lacy carbon membrane on 300-mesh copper grid, blotted to a thin film width filter paper, and immediately plunged into liquid ethane in a Reichert KF-80 cryo-station. Samples were kept under liquid nitrogen before transferring to an Oxford CT-3500 cryoholder and surface coated with chromium at $1 \times 10^{-5}$ Pa and –160° C. The grid or carrier containing the vitrified suspension was transferred into a Topcon DS130F Schottky field emission scanning transmission and high resolution secondary electron-I microscope modified to accept an Oxford CT-3500 TEM-type cryostage. Crystalline ice was removed by sublimation at approximately –105° C. Imaging was performed at 25 kV to minimize beam damage and at magnifications of up to 200,000×.

Cryo-SEM images demonstrate the 3-D spherical nature of this particular PEO star in vitrified water. Diameters range from 17 to 50 nm with an average diameter of approximately 30 nm. This size range reflects the polydispersity of this commercially prepared sample, although the possibility that two dendrimers have aggregated cannot be excluded. Nonetheless, the mean dendrimer diameter compares remarkably with the anticipated diameter of 29 nm. The use of cryo-TEM presented similar images. These studies demonstrate that dendrimers in the frozen hydrated state are circular in projection and under appropriate circumstances can be uniformly distributed in a plane. Significantly these investigations confirm the capability to characterize individual PEO dendrimers in a near native hydrated environment.

Example 17

Figure 17:
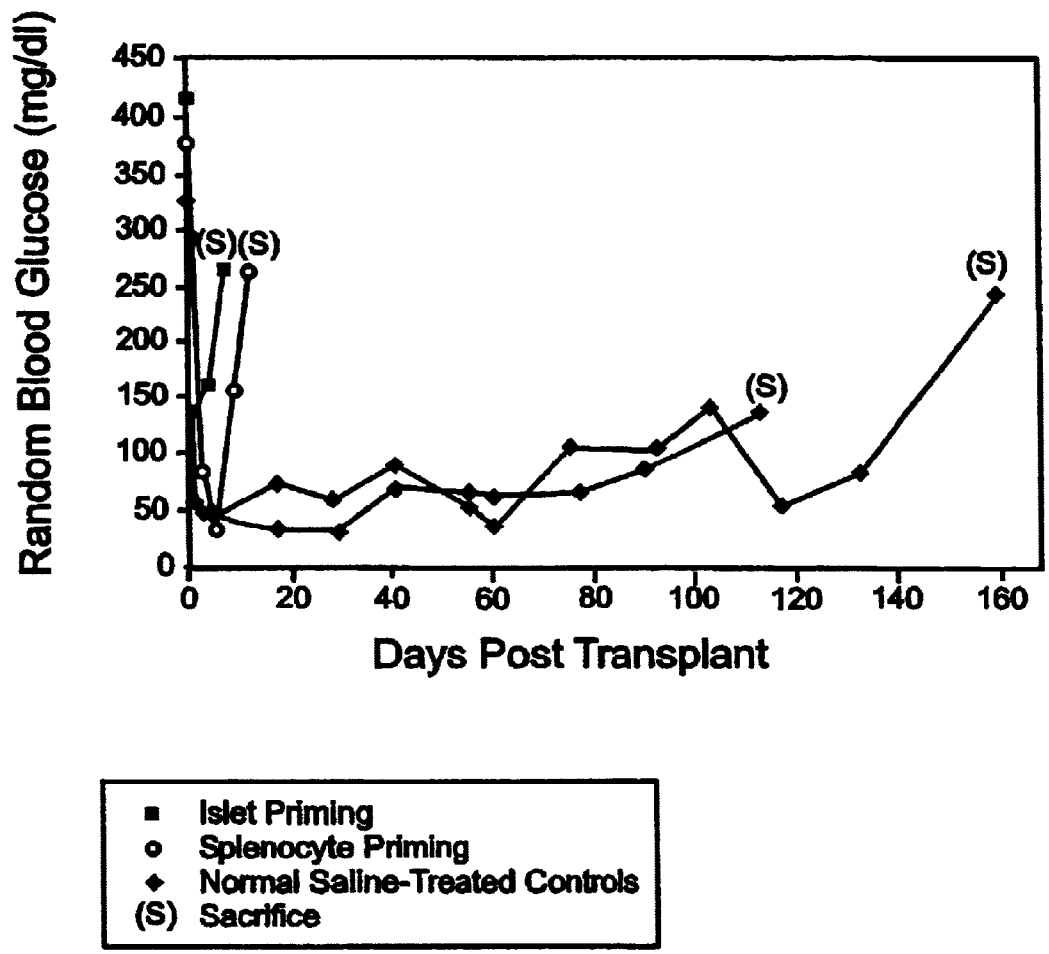
FIG. 17 shows the effect of Lewis rat islet priming on Lewis rat-to-NOD encapsulated islet xenograft survival.

Elucidation of Immunological Pathways Active in the Destruction of Encapsulated Xenogeneic Islets Microcapsules reduce host sensitization by liming the release of islet associated antigens. Microencapsulation prolongs the functional survival of islet xenografts in diabetic NOD mice when compared to the survival of unencapsulated islets injected into the spleen. The same is true for islet allo- and isografts transplanted into NOD mice. (Weber, C. J. et al. [1995] *Transplantation Proceedings* 27:3308-3311; Weber, C. J. et al. [1997] *Cell Transplantation* 6:505-508; Weber, C. J. et al. [1994] *Transplantation Proceedings* 26:1116-1119, and Table 1.) To clarify the mechanisms of long-term microcapsule protection of xenogeneic rat islets, paired diabetic NOD mice were injected intraperitoneally with either 200 Lewis rat islets (presensitized NOD) or Hank's balanced salt solution (HBSS; control NOD). Encapsulated Lewis rat islets were subsequently grafted into presensitized and control NOD mice 14 days later. Islet pretreatment resulted in rapid graft rejection (10±7 days; n=4) while non-sensitized NOD mice showed prolonged survival of encapsulated xenogeneic islets (116±37 days; n=5) (FIG. 17). Similar results were observed if NOD mice were pre-treated with an i.p. injection of $10^6$ Lewis rat splenocytes. These data show that a major function of microcapsules is to reduce recipient sensitization rather than to solely protect grafts from the effector arm of the host response. Thus, maneuvers which reduce the release of islet associated antigens by enhancing the permselectivity of the encapsulating barrier will enhance islet survivability.

A Th2 T cell response is responsible for the rejection of encapsulated islet xeno grafts. To elucidate the pathogenesis of encapsulated islet cell destruction, xenogeneic rat, dog, and rabbit islets were grafted intraperitoneally into NOD mice. mRNA was extracted from NOD peritoneal cells harvested at the time of graft rejection and the expression of IL-2, IL-4, and IL-10 was studied by RT-PCR. (Weber, C. J. et al. [1995] *Transplantation Proceedings* 27:3308-3311.) Integrity of RNA samples was assessed by inspection of Northern blots that were hybridized with the probe for the 3' untranslated region of β-actin. IL-4 was detected in the majority of encapsulated islet xenografts undergoing rejection. IL10 expression was variable, and IL-2 was detected during the autoimmune destruction of NOD isografts but rarely in rejecting xenografts. These data show that the primary T cell response in rejecting encapsulated islet xenografts is "Th-2"-like and differs from the T cell response to allogeneic islets. O'Connell and colleagues (Nickerson, P. et al. [1993] *Transplantation Proceedings* 25:984-985; O'Connell, P. J. et al. [1993] *J. Immunol.* 150:1093-1104) have also demonstrated that IL-2 messenger RNA is detected in biopsies of rejected allogeneic islets. Increased 'Th2' relative to 'Th1' activity is distinct from the known NOD "Th1" anti-islet immune response. (Kaufman, D. et al. [1993] *Nature* 365:69-72; Janeway, C. and Bottomly, K. [1994] *Cell* 76:275-285.) The "Th2" response is characteristic of evoked antibody responses to foreign antigens, and suggests that humoral reactions may be important to rejection of encapsulated islet xenografts. (Takeuchi, T. et al. [1992] *Transplantation* 53:1281-1294.) Therefore, strategies designed to abrogate 'Th2' responses prolong encapsulated islet xenograft survival.

A pericapsular cellular response is observed at the time of xenograft rejection and dominated by macrophages. Biopsies were performed on both functioning and rejected encapsulated islet xenografts from peritoneal graft sites of diabetic NOD nice at various times post-transplantation. The total number of peritoneal (pericapsular and free) cells were not significantly different when harvested either from untreated mice or from NODs treated with empty capsules or capsules with functioning islet xenografts ($<14 \times 10^5$ cells). However peritoneal cell numbers increased dramatically at rejection ($613 \times 10^5$ cells).

Analysis of the pericapsular infiltrate was performed by flow cytometry (FACS). Adherent cells were freed by gently pipetting biopsied capsules in Hank's solution. FACS analysis revealed that 20-50% of the nonadherent peritoneal cell population were B220$^+$ (B cells) and that the percentages of CW4$^+$ and CD8$^+$ cells were low (4-9%). The majority of free peritoneal cells, as well as those cells adherent to microcapsules were characterized as Mac 1$^+$ (macrophages). By FACS analysis, the phenotype of peritoneal Mac1$^+$ cells shifted from predominantly Gran $^-$1 to Gran 1$^+$ (i.e. "activated" macrophages) during rejection of xenogeneic islets. These findings were confirmed by immunocytochemistry, where Mac1$^+$ cells comprise approximately 80% of the cellular infiltrate. In addition, immunocytochemical staining has documented the presence of IgG and IgM around microcapsules and both IL-1 and TNFα in pericapsular cells and within microcapsules.

Example 18

Figure 18:
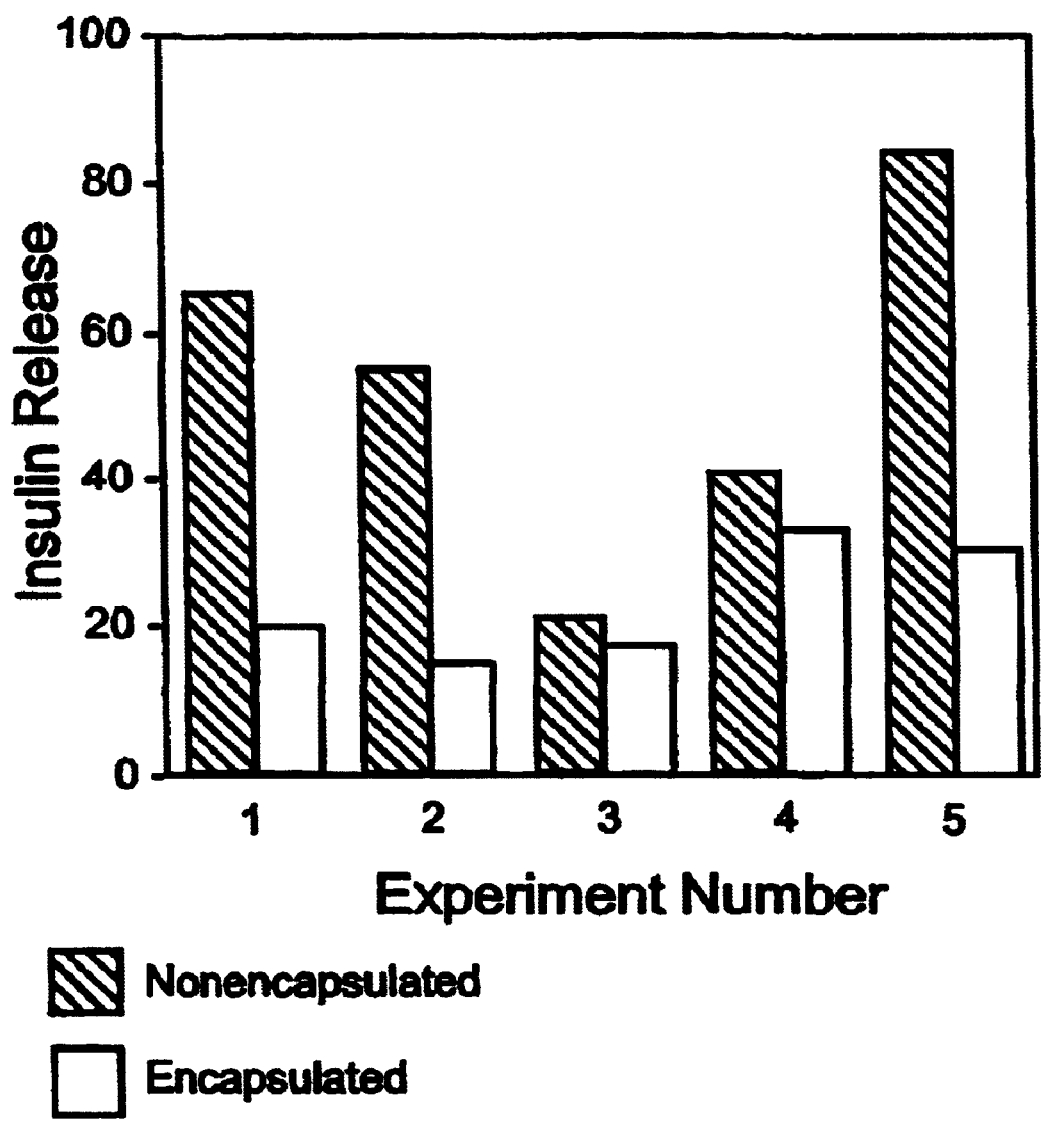
FIG. 18 shows in vitro insulin release from non-encapsulated (N) and encapsulated (E) neonatal porcine islets (μU/1000 islets/24 hr).

Characterization of Neonatal Pig Islet Cell Function In Vitro and as an Encapsulated Xenograft In Vivo Neonatal pig islets continue to release insulin in vitro after microencapsulation. Xenogeneic islets, including those from pig, bovine, rabbit, and subhuman primates have all been capable of maintaining normoglycemia in diabetic rodents until transplant rejection occurs. Nonetheless, the recent development of techniques for large-scale isolation of islets from neonatal pigs and increased success in generating transgenic porcine strains has made pig donors the most promising xenogeneic source for use in human diabetes. Based upon prior reports, a reproducible method for isolation of large numbers of functionally viable islets from neonatal pig donors was developed. (Korbutt, G. S. et al. [1995] *Transplantation Proceedings* 27:3212; Weber, C. J. et al. [1997] *Cell Transplantation* 6:505-508; Korbutt, G. S. et al. [1996] *J. Clin. Invest.* 97:2119-2129; Korbutt, G. S. et al. [1995] *Transplantation Proceedings* 28:821-823.) With this technique 30,000-100,000 islets may be obtained from each donor pin. Neonatal pig islet cells continue to secrete insulin in vitro after microencapsulation (FIG. 18). (Weber, C. J. et al. [1997] *Cell Transplantation* 6:505-508; Janeway, C. and Bottomly, K. [1994] *Cell* 76:275-285.) These neonatal pig islets are actually dispersed neonatal pig pancreatic cells which re-aggregate to form "islet"-like spheroids and are composed of approximately 5-10% beta cells; a proportion significantly higher than the 1-2% beta cell concentration in the adult pig pancreas.

Figure 19:
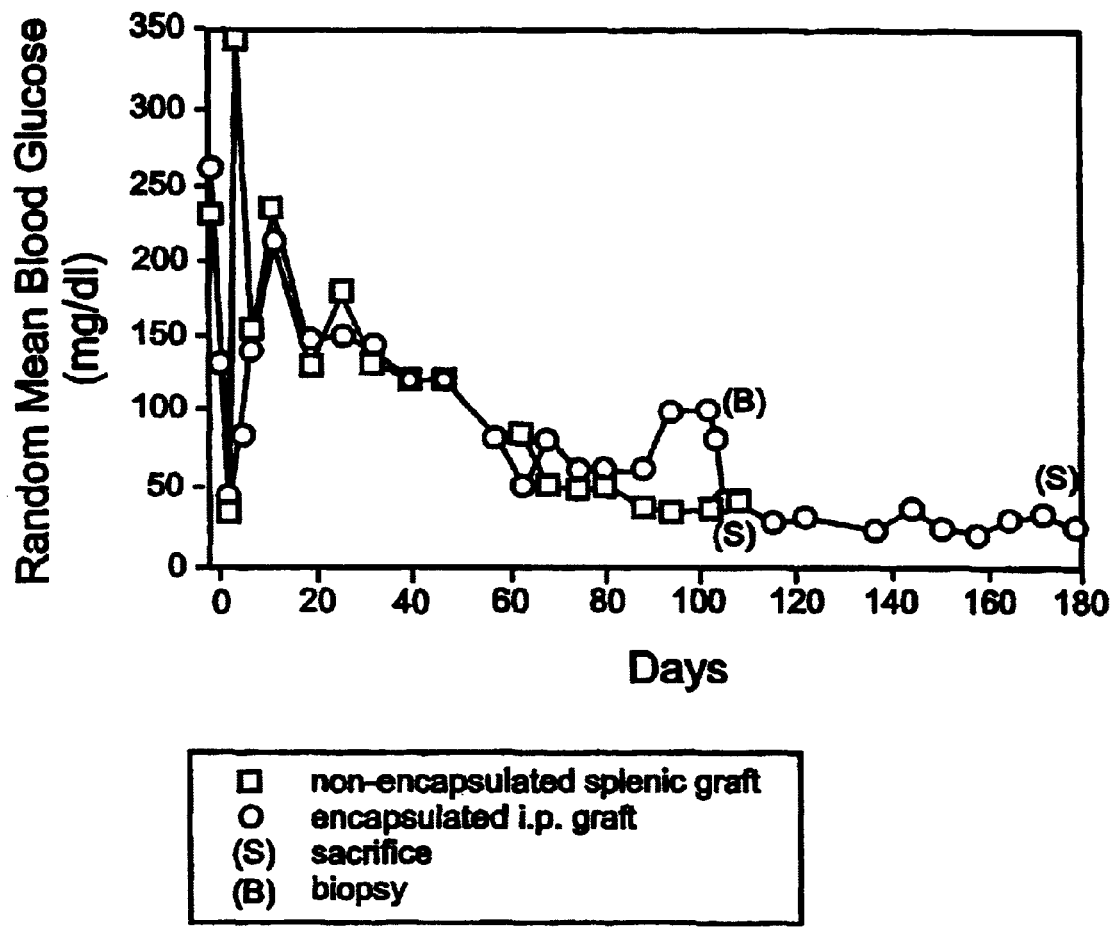
FIG. 19 shows neonatal pig islet xenografts in streptozotocin diabetic NOD-Scid mice. □=nonencapsulated splenic graft; ○=encapsulated i.p. graft; S=sacrifice; B=biopsy.
Figure 20A:
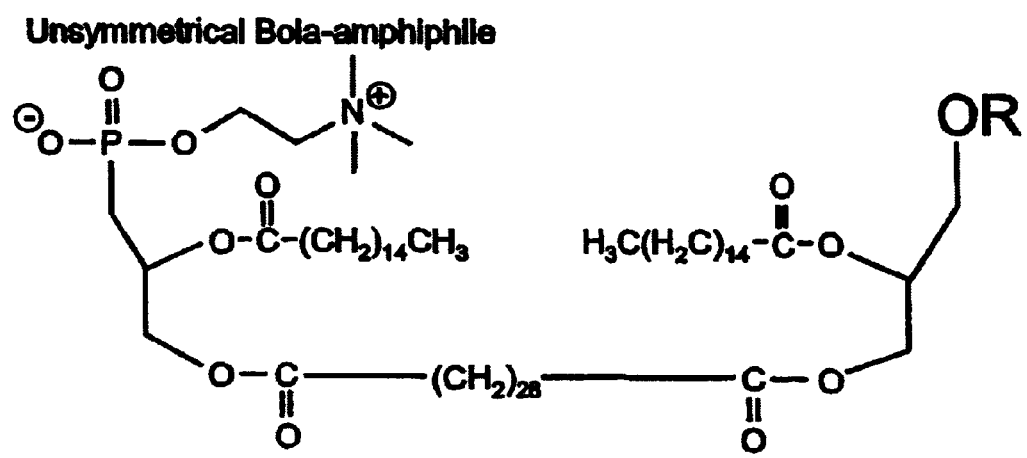
FIG. 20 shows construction of a membrane-mimetic surface from a boloamphiphile fabricated directly on a polyelectrolyte covering a substrate.
Figure 20B:
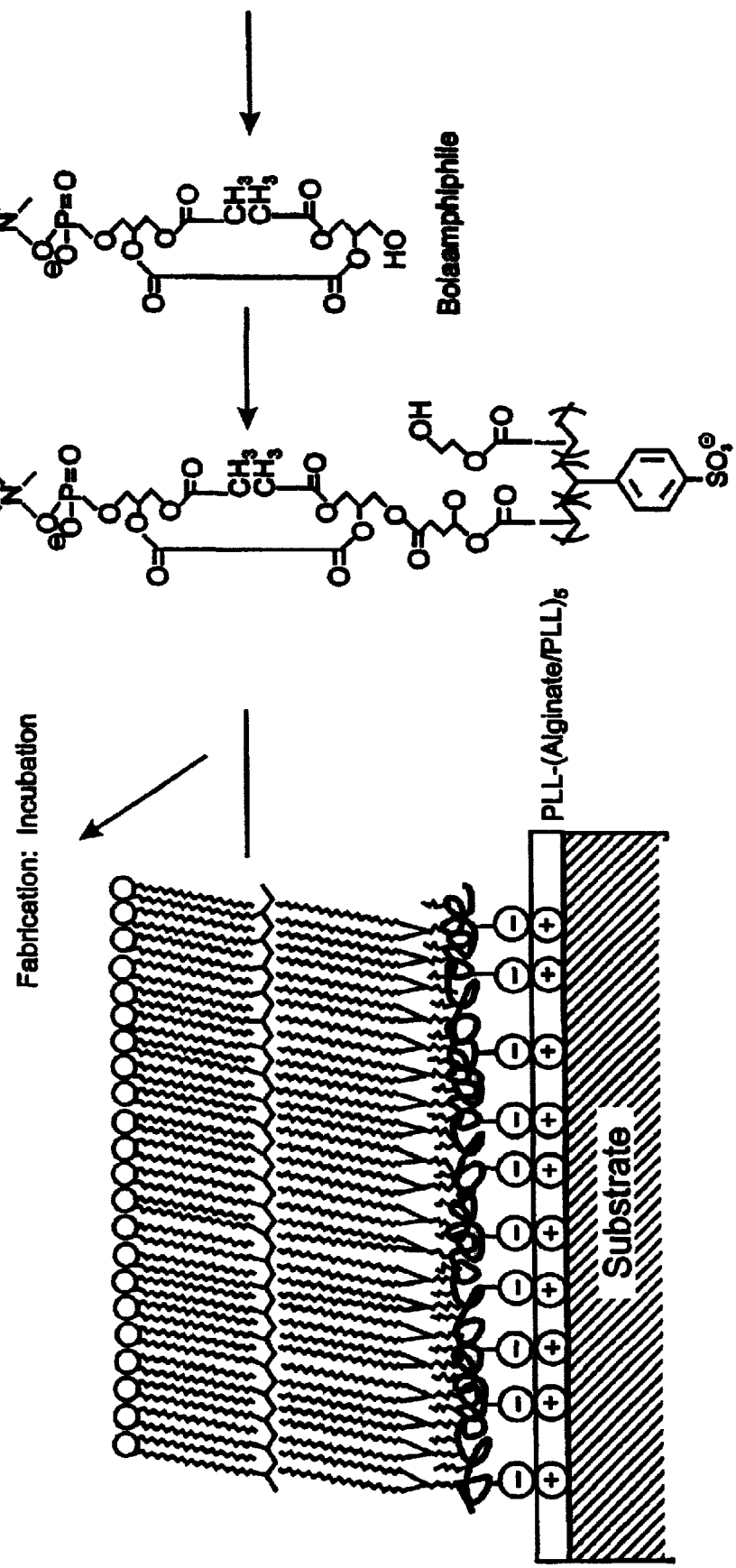
Figure 20C:
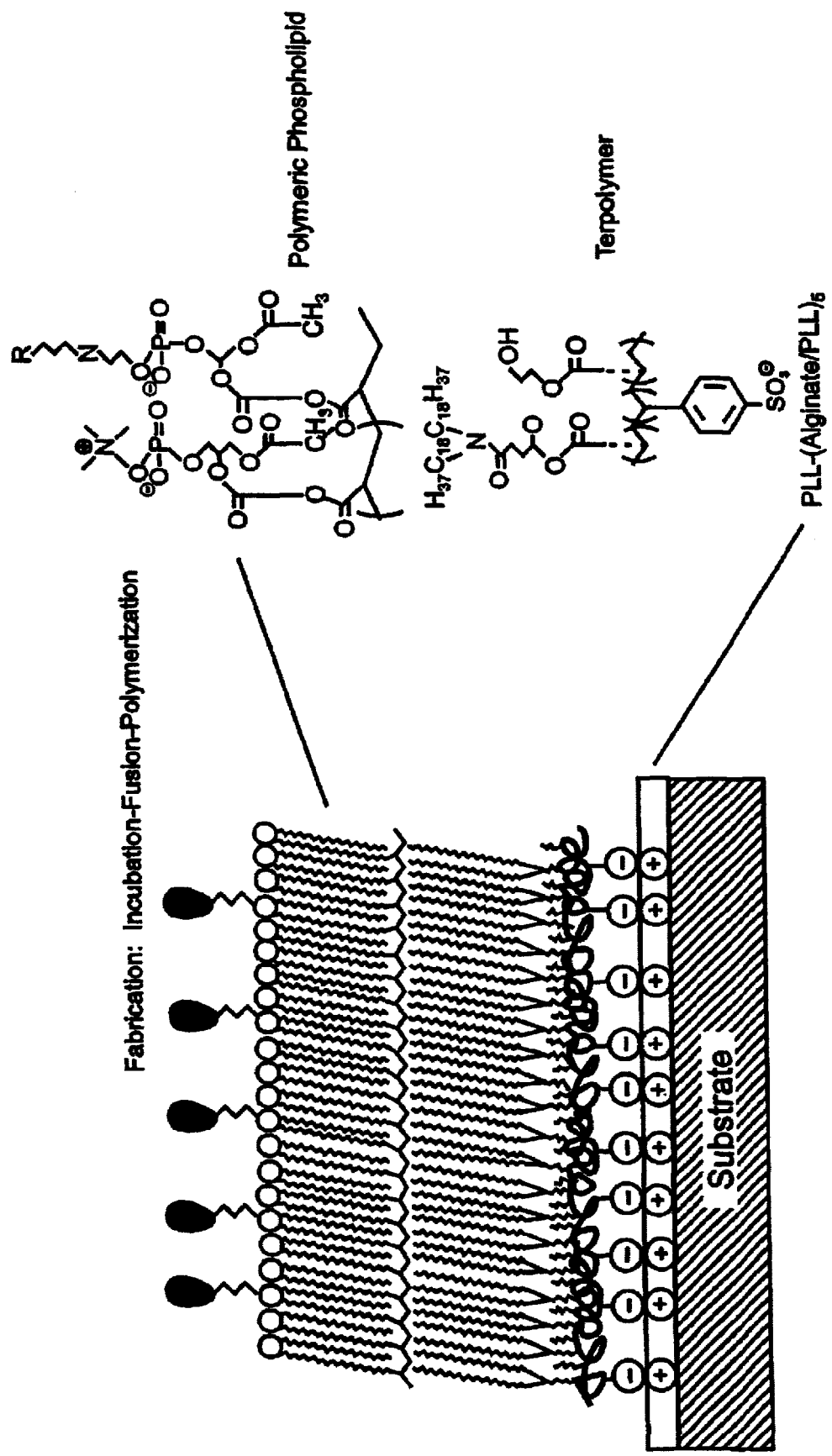

Euglycemia is achieved in NOD mice after transplantation of neonatal pig islets. Spontaneously diabetic NOD mice reject islet xenografts soon after transplantation. For example, unencapsulated neonatal pig islets placed beneath the splenic capsule are rejected in 6±1 days. While encapsulation in alginate-poly-L-lysine significantly prolongs islet Oval to 27±13 days, assessment of long-term islet function in xenogeneic recipients is limited Recently, the Scid mutation has been back-crossed onto the NOD background, resulting in immunodeficient NOD-Scid mice. (Shultz, L. et al. [1995] *J. Immunology* 154:180-191; Gerling, I. et al. [1994] *Diabetes* 43:433-440; Christianson, S. et al [1993] *Diabetes* 42:44-45.) These mice are homozygous for the Scid mutation which results in an inability to rearrange T-cell receptor and immunoglobulin genes. Consequently, these mice lack T and B-lymphocytes. NOD-Scid mice do not develop diabetes spontaneously; but they can be rendered diabetic after treatment with multiple low-dose streptozotocin. (Gerling, I. et al. [1994] *Diabetes* 43:433-440.) To document the long-term functional activity of neonatal pig islets, grafts were placed into NOD-Scid mice rendered diabetic with streptozotocin. Both non-encapsulated intra-splenic and encapsulated (alginate-poly-L-lysine) intraperitoneal islets restored a euglycemic state for more than 100 days (FIG. 19). This data demonstrates that neonatal pig islets survive and function physiologically in xenogeneic recipients for prolonged periods, in the absence of an immunological attack.

Example 19

A Synthetic Glycocalyx can Selectively Inhibit Complement-dependent Cytotoxicity Through the Appropriate Choice of Constituent Glycolipid In order to assess the capacity of synthesized membrane-mimetic materials to directly activate the complement pathway, generation of C3a, C4a, and C5a are measured using the Amersham human complement $^{125}$I radioimmunoassay (RIA) system. (Chaikof, E. L. et al. [1992] *J. Biomed. Mater. Res.* 26:1163-1168.) Nonencapsulated and encapsulated porcine islets of varying test membrane composition are incubated with human serum diluted 1:4 in veronal buffered saline (VHS) as a source of xenoreactive antibodies and complement. Complement activation in the fluid phase are assessed in a time-dependent fashion (0-48 h) by measuring the total complement activity (CR50) and the release of C3a/C3ades Arg, C4a, C5a antigen by radioimmunoassay (Amersham human complement RIA kit). Deposition of iC3b, C5 antigen, and C5b-9 are also be defined by immunohistochemical staining and quantitative radioimmunoassay with antibodies against iC3b neoantigen, C5, and C5b-9.

Example 20

Increasing the Surface Ratio of Membrane Bound Chondroitin to Heparan Sulfate will Reduce Macrophage Adhesion While Maintaining Barrier Associated Anti-complement Activity Model membranes are produced with varying GAG mole ratios of HS:CS. Macrophages harvested from peritoneal cavity of NOD nice, are labeled with $^{51}Cr$ and their adhesion to test substrates defined by a differential centrifugation assay. The ability of resident (non-activated) and activated peritoneal macrophages to adhere to test surfaces is determined by using macrophages harvested either from the peritoneal cavity of normal mice or from those stimulated with an intraperitoneal injection of thioglycolate. (Qui, Z. H. et al. [1994]) *J. Biol. Chem.* 269:19480-19487.) The proportion of non-activated to activated macrophages harvested under these conditions is characterized by FACS analyses of Mac-$1^+$/Gran $1^-$ (non-activated) and Mac-$1^+$/Gran $1^-$ (activated) cells.

Example 21

Dendrimers with Macromolecular Generations Produce Well-defined Transmembrane Channels with a Narrow Distribution or Pore Size in the Subnanometer Range Characteristically, following beta cell secretion, insulin circulates as a dimer which can be modeled as a sphere with an effective radius of 23 Å. (Dodson, G. G. et al. [1993] *Biochem. Soc. Trans.* 21:609-614; Blundell, T. et al. [1972] Advances in Protein Chemistry, Vol. 26, New York: Academic Press.) The construction of an "ideal" pore facilitates the relatively free passage of insulin and glucose. Therefore, given the known dimensions of the insulin dimer, unhindered transport requires an effective pore size in the range of 25-30 Å.

The effective pore size is determined by dendrimer size, generation arm length, and the event of internal branching. For an effective pore size of 30 Å, the PEO dendrimer will require three macromolecular generations with an average molecular weight of 5,000 to 10,000 g/mol for each arm (Scheme 5). Dendrimers are end-functionalized at each terminal branch point with a Cl 8 dialkyl moiety in order to facilitate their stable incorporation.

In order to firer define the effect of PEO dendrimers on transmembrane mass transport, candidate PEG "channels" are inserted into membrane-mimetic films as follows. Lipid vesicles, composed of polymerizable phospholipids are produced by a freeze-thaw and serial extrusion process. Vesicle solutions are incubated with varying concentrations of the test dendrimer. The upper concentration of dendrimer beyond which liposome disruption is observed is determined by light scattering. Subsequently, dendrimer containing vesicles are fused onto alkylated substrates and polymerized in situ, as described elsewhere. (Marra, K. C. et al. [1997] *Langmuir* 13:5697-5701; Marra, K. C. et al. [1997] *Macromolecules* 30:6483-6487.) The choice of alkylated substrate is determined by s c physiochemical or biological parameters to be defined:

(i) Morphological and structural characterization by AFM, ESCA, and contact angle goniometry require vesicle fusion onto self-assembled monolayers of octadecyl trichlorosilane (OTS) glass. Serial contact angle measurements over time allows characterization of overall film stability under aqueous conditions in vitro.

(ii) Analysis of dendrimer ("artificial" pore size) distribution, and segregation within membrane-mimetic films is performed by cryoelectron microscopy on both model capsules and planar membranes formed on alginate coated glass slides. Techniques utilize both cryo-emission scanning transmission and high resolution secondary electron-I microscopy (STEM/HRSEM). Significantly, this approach permits near-native structure to be observed with control of environmental variables such as buffer, pH and ionic strength and without dehydration or staining. Resolution of 4 nm is well within the range of these techniques.

(iii) Transport characteristics of biomimetic and standard poly-L-lysine/alginate microcapsules is determined by calculating mass transfer and permeability coefficients for diffusing species ranging in molecular weight from $10^2$ to $10^5$. Capsules are loaded with $^{125}$I-labeled markers of varying size (e.g., glucose 180 MW, vitamin B 12 1300 MW, insulin 11 kD MW, carbonic anhydrase 29 kD MW, bovine serum albumin 66 kD MW, IgG 150 kD MW). Test samples are incubated in phosphate buffered saline (PBS) at 37° C. and the release of radioactivity measured at regular intervals. The unsteady-state diffusion of the marker from a sphere is analyzed.

(iv) Once the formation of a dendrimer containing membrane-mimetic film is optimize, function and viability of encapsulated pancreatic islets are evaluated in vitro, as described above.

Example 22

A Membrane-mimetic Immunoisolation Barrier Incorporating Both GAG-lipid Conjugates and Dendritic Polymers, as Transmembrane Channels Does Not Elicit Non-specific Inflammatory Responses Empty "biomimetic" (i.e., membrane mimetic coated), as well as standard poly-L-lysine/alginate capsules are grafted intraperitoneally into NOD mice. Capsules are retrieved at 2, 4, 8, 16, and 24 weeks and the peritoneal inflammatory response investigated using light microscopy. If a cellular infiltrate is observed, immunohistochemistry, FACS, and PCR analysis is also performed, as outlined below.

The development of an inflammatory response may be related to impaired capsule stability in a biological environment. Membrane-mimetic surfaces are produced on capsules formulated with a "double-wall" of alginate. Double-wall poly-L-lysine-alginate capsules are more durable than conventional microcapsules, due to, at least in part, a reduction in islet protrusion through the capsule wall. Nonetheless, in order to characterize the biostability of empty biomimetic capsules in vivo, FITC conjugated murine IgG is loaded into empty capsules as a marker of barrier integrity. Capsules are retrieved at 2, 4, 8, 16, and 24 weeks and fluorescence intensity per capsule measured by quantitative fluorescence microscopy. Capsules containing FITC-IgG and incubated in PBS at 37° C. are used as a parallel negative control group.

Example 23

Both Th1 and Th2 Responses are Blocked and Graft Survival Enhanced when Donor Islets are Encapsulated in a Biomimetic Barrier NOD and neonatal porcine (White Landrace pig) islets are isolated and cultured in vitro. Approximately, 8000 islets are encapsulated in double wall, alginate microcapsules either functionalized with a biomimetic membrane or in the standard poly-L-lysine/alginate formulation and grafted intraperitoneally in NOD mice. Controls receive 8000 unencapsulated islets grafted beneath the splenic capsule. Graft function is monitored daily by measurement of random blood glucose for 2 weeks and then weekly. Graft rejection has been defined as random blood glucose>250 mg/dL for 2 consecutive days. The peritoneal inflammatory response to encapsulated islets is analyzed at weekly intervals by immunohistochemistry, FACS, and PCR analysis.

Impaired capsule stability in a biological environment is potentiated by the presence of encapsulated islet cells. Specifically, the initiation of a low grade inflammatory response, as a consequence of antigen release or other factors, may lead to capsule degradation with further loss of barrier integrity. In order to characterize the biostability of islet containing capsules in vivo, FITC conjugated murine IgG is loaded into capsules as a marker of barrier integrity. Capsules will be retrieved at 2, 4, 8, 16, and 24 weeks and fluorescence intensity per capsule measured. The effect of both isogeneic and xenogeneic (porcine-NOD) islets on capsule integrity is characterized. Alginate-poly-L-lysine capsules containing F1TC- IgG and incubated in PBS at 37° C. is used as a parallel control group. Good stability is found.

This invention is illustrated by various specific examples but is not limited to any specific components or process steps for which equivalents are known to the art.

TABLE 1

Thin film thickness as determined by ellipsometry

| Film | Thickness (Å) |
|---|---|
| Si-(PLL-Alg)$_5$-PLL | 154 ± 7.5 |
| PLL-Alg bilayer | 28 ± 7.5 |
| Si-(PLL-Alg)$_5$-PLL-Ter | 206 ± 7.1 |
| Terpolymer layer | 52 ± 7.1 |
| Si-(PLL-Alg)$_5$-PLL-Ter-PC | 229 ± 4.5 |
| PC layer | 23 ± 4.5 |

TABLE 2

Angled-dependent XPS analysis of multilayer assembly during the formation of a supported membrane-mimetic thin film

| Film | Atom | 15° | 45° | 90° | Predicted† |
|---|---|---|---|---|---|
| (PLL-Alg)$_5$-PLL | C | 65.8 ± 1.7 | 60.8 ± 0.8 | 59.5 ± 2.9 | 62.0 |
| | N | 9.2 ± 1.4 | 10.4 ± 1.6 | 9.9 ± 0.3 | 24.2 |
| | O | 24.2 ± 1.6 | 27.6 ± 1.1 | 28.0 ± 1.8 | 13.8 |
| | C | 77.7 ± 9.5 | 78.3 ± 1.5 | 75.9 ± 3.8 | 76.2 |

TABLE 2-continued

Angled-dependent XPS analysis of multilayer assembly during the formation of a supported membrane-mimetic thin film

| Film | Atom | 15° | 45° | 90° | Predicted† |
|---|---|---|---|---|---|
| (PLL-Alg)$_5$-PLL-Ter | N | 2.6 ± 1.4 | 3.8 ± 1.3 | 3.2 ± 1.4 | 1.6 |
| | O | 15.3 ± 6.4 | 16.2 ± 0.9 | 18.0 ± 1.8 | 21.1 |
| | S | 0.27 ± 0.05 | 0.8 ± 0.3 | 1.0 ± 0.6 | 1.1 |
| (PLL-Alg)$_5$-PLL-Ter-PC | C | 75.6 ± 12.7 | 74.2 ± 7.8 | 72.9 ± 5.4 | 76.5 |
| | N | 0.13 ± 0.7 | 2.1 ± 0.46 | 1.9 ± 1.6 | 2.0 |
| | O | 17.3 ± 5.8 | 19.0 ± 4.3 | 19.7 ± 3.2 | 19.6 |
| | S | 0 | 0 | 0 | 0 |
| | P | 3.7 ± 0.2 | 0.97 ± 0.5 | 0.87 ± 0.2 | 1.85 |

†Approximate estimate as determined by simple atom counting.

TABLE 3

Infrared band assignments for successive assembly of a supported membrane-mimetic thin film

| Absorption mode | (PLL/alginate)$_5$-PLL (Frequency cm$^{-1}$) | | (PLL/alginate)$_5$-PLL-Terpolymer (Frequency cm$^{-1}$) | | (PLL/alginate)$_5$-PLL-Terpolymer-AcrylatePC (Frequency cm$^{-1}$) | |
|---|---|---|---|---|---|---|
| | $R_s$ | $R_p$ | $R_s$ | $R_p$ | $R_s$ | $R_p$ |
| —OH stretch | 3500–3000 | 3500–3000 | 3500–3000 | 3500–3000 | 3500–3000 | 3500–3000 |
| —CH stretch | 2934.0 | 2930.0 | | | | |
| —CH$_2$ stretch (antisymmetric) | | | 2925.3 | 2928.5 | 2924.3 | 2920.2 |
| —CH$_3$ stretch (symmetric) | | | | 2872.9 | | |
| —CH$_2$ stretch (symmetric) | | | 2154.7 | 2155.3 | 2154.1 | 2153.7 |
| —C=O stretch (ester) | | | 1735.2 | 1739.4 | 1739.4 | 1741.5 |
| —C=O—NH stretch (amide I) | 1650.3 | 1650.1 | 1647.9 | 1652.4 | 1647.3 | 1652.2 |
| N—H bend of NH$_3^+$ | ~1620–1610 | ~1620–1610 | ~1620–1610 | ~1620–1610 | ~1620–1610 | ~1620–1610 |
| —COO$^-$ antisymm stretch | | 1550.0 | | 1549.0 (sh) | | 1548.0 |
| —CH$_2$ bend (scissoring) | 1466.7 | 1456.4 | 1467.4 | 1461.1 | | |
| —COO$^-$ symm stretch | | 1409.2 | | 1408.0 | 1402.8 | |
| —PO$_2^{31}$ symm + CO—O—C | | | | | 1262.6 | |
| —CO—O—C antisymm stretch | | | 1172.2 | | 1164.6 | |
| —CO—O—C symm stretch | | | 1104.9 | | 1101.1 | |
| —C—O stretch | 1110.7 | | | | | |
| | 1031.5 | | 1030.0 (weak) | (weak) | 1026.3 | |

TABLE 4

Determination of Km and kcat for TM as a function of local lipid microenvironment†

| | Free TM | TM in POPC vesicles | TM in AcPC vesicles | TM in polymerized AcPC vesicles |
|---|---|---|---|---|
| Km (μM) | 3.6 ± 1.1 | 0.66 ± 0.14 | 0.86 ± 0.10 | 4.5 ± 0.9 |
| kcat (min$^{-1}$) | 7.0 ± 1.0 | 4.6 ± 0.2 | 2.6 ± 0.1 | 5.7 ± 0.6 |

TABLE 4-continued

Determination of Km and kcat for TM as a function of local lipid microenvironment†

|  | Free TM | TM in POPC vesicles | TM in AcPC vesicles | TM in polymerized AcPC vesicles |
|---|---|---|---|---|
| kcat/Km ($min^{-1} \cdot \mu M^{-1}$) | 1.94 | 6.97 | 3.02 | 1.27 |
| Km (µM) (ref. 60) | 7.5 | 0.7 | NA | NA |

†Rabbit TM, human protein C, and human thrombin were utilized in all experiments

TABLE 5

Beneficial Effect of Microencapsulation on Survival of Iso-, Alle-, and Xenografts in NOD Mice

| Donor-Reciepient | Technique | N | Survival (days: x ± SE) |
|---|---|---|---|
| NOD-NOD | CAP/I.P. | 4 | 44 ± 7* |
| NOD.NOD | Splenic | 3 | 7 ± 1 |
| Lewis rat-HOD | CAP/I.P. | 8 | |
| Lewis rat-NOD | Splenic | 9 | 19 ± 3 |
| Neonatal pig-NOD | CAP/I.P. | 8 | 27 ± 13 |
| Neonatal pig-NOD | Splenic | 3 | 6 ± 1 |

*p < 0.01
CAP/I.P. = microencapsulated islet graft to peritoneal cavity
Splenic = nonencapsulated islets grafted beneath the splenic capsule

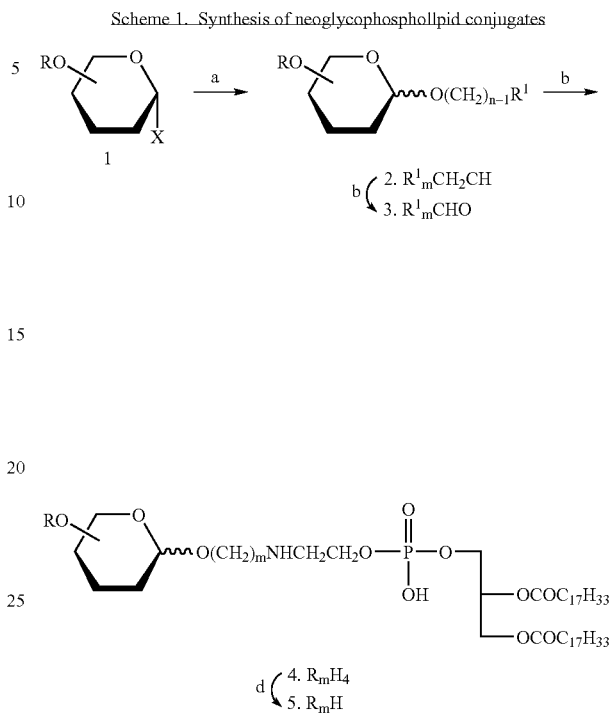

Scheme 3. Synthesis of HEA:AOD (2:1) and HEA:AOD:styrene sulfonate (6:3:1).
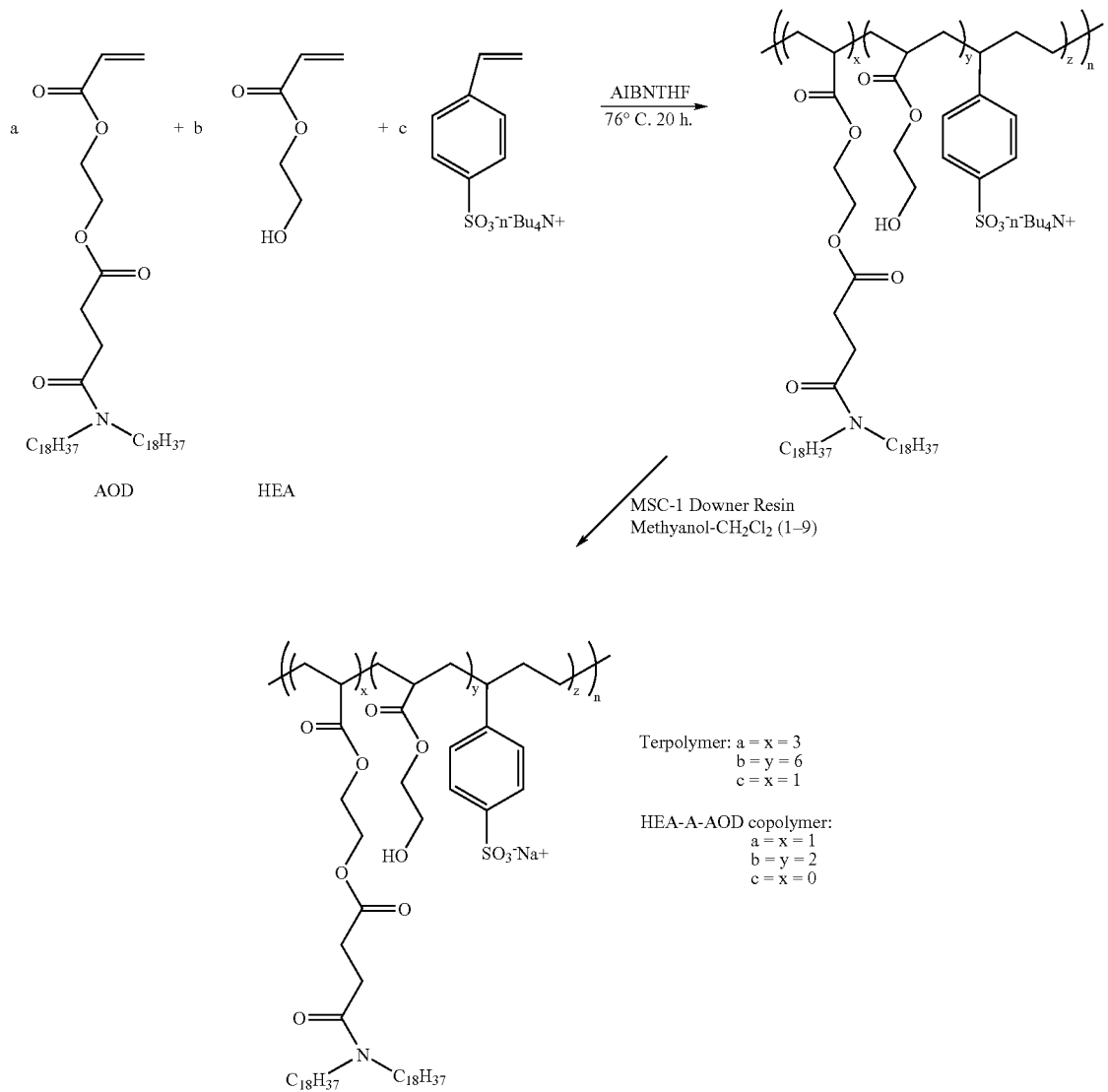
Scheme 4.
Synthesis of a second generation nine-arm PEO dendrimer. Mn of first (a) and second (b) generation arms are 2300 and 7500, respectively.
A: POLYMERIZATION
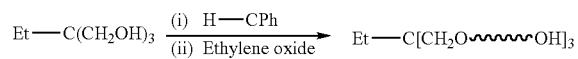
B: ARBORIZATION
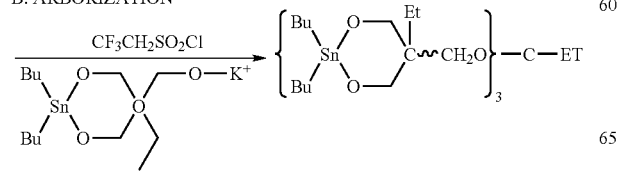
C: DEPROTECTION
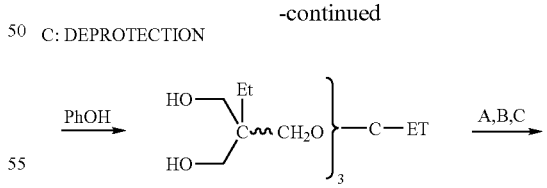
SECOND GENERATION PEO DENDRIMER Scheme 5. Synthesis of PEO dendrimers end-functionalized with C18 dialkyl units fitted with a vinyl unsaturation (methyl atropate).

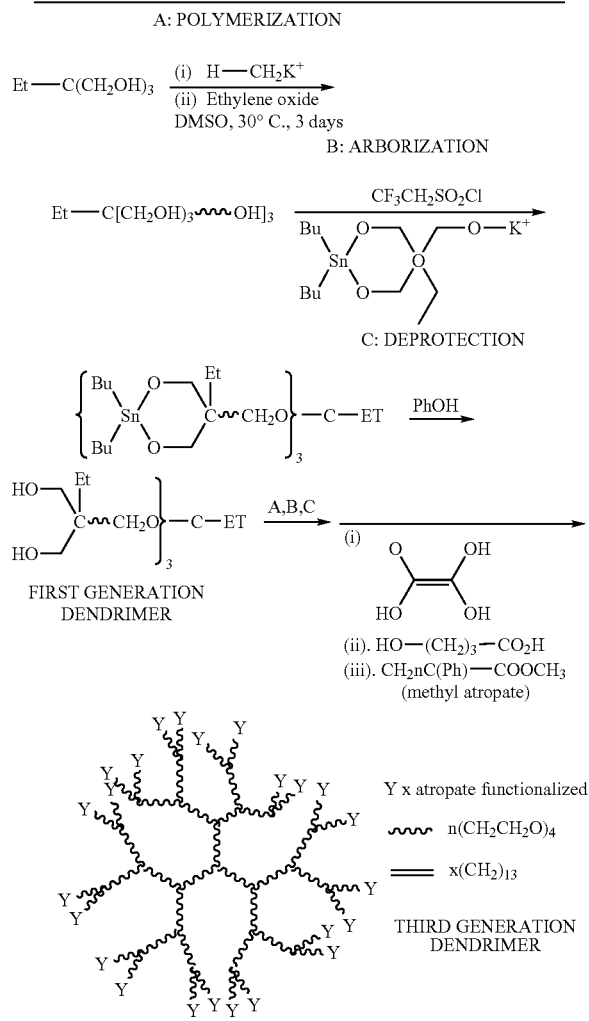

The invention claimed is:

1. A biological component comprising an artificial membrane and a substrate, wherein said artificial membrane is in a form other than vesicular form, and a polyelectrolyte cushion layer comprising a PLL/alginate bilayer between said artificial membrane and substrate; wherein said artificial membrane is a membrane mimetic film comprising a terpolymer layer adjacent to said multilayer cushion and a polymerizable phospholipid layer adjacent to said terpolymer layer, wherein said terpolymer layer is between said phospholipid layer and said multilayer cushion.

2. The biological component of claim 1 wherein said phospholipid is selected from the group consisting of phosphatidylcholine, phosphatidylethanolamine, phosphatidylglycerol, ether-based phospholipids, peptide conjugates of phospholipids and gylocolipid conjugates of phospholipids.

3. The biological component of claim 1 wherein said substrate is selected from the group consisting of implantable prostheses, artificial organs, cells, and drug delivery devices.

4. The biological component of claim 1 wherein said substrate is a hydrated substrate.

5. The biological component of claim 1 wherein said substrate is selected from the group consisting of gelatin, collagen, alginate, and chitosan and comprises a bioactive substance, wherein said bioactive substance is a drug for administration to a patient to correct a pathological defect.

6. The biological component of claim 5 wherein said substrate is an alginate comprising a bioactive substance, wherein said bioactive substance is a drug for administration to a patient to correct a pathological defect.

7. The biological component of claim 1 wherein said membrane-mimetic film comprises pores of a selected size.

8. The biological component of claim 1 wherein said membrane-mimetic film has been functionalized to modulate interactions between a cell, tissue, blood, organ or other living material and said membrane mimetic film, or the substrate on which said membrane mimetic film has been placed.

9. The biological component of claim 8 where such modulated interactions are selected from the group consisting of reduction of thrombogenicity, reduction of inflammatory response, selective transport of molecules through said membrane, and sequestering of particles from the host into which the biological component has been placed.

10. A biological component comprising a hydrated substrate coated with a stable, alkylated surface by the steps of:
complexing a polyelectrolyte onto the hydrated substrate,
coating the surface of the polyelectrolyte with an oppositely charged amphiphilic polymer containing long-chain alkanes; wherein said amphiphilic polymer comprises a terpolymer; and
coating the amphiphilic polymer with a polymerizable phospholipid.

11. The biological component of claim 10 wherein a membrane-mimetic surface is formed on the alkylated surface.

12. The biological component of claim 10 wherein said substrate comprises one or more materials selected from the group consisting of cells, and natural or synthetic polysaccharides and proteins which complex with a polyelectrolyte.

13. The biological component of claim 12 wherein said material comprises a natural or synthetic collagen, gelatin, alginate, recombinant collagen protein or protein-mimetic polypeptide polymer.

14. The biological component of claim 10 wherein said hydrated substrate comprises a bioactive molecule.

15. The biological component of claim 14 wherein said bioactive molecule enhances cell viability or function, or minimizes local host inflammatory responses.

16. The biological component of claim 10 wherein said hydrated substrate is comprised within openings in a device for implantation into a patient.

17. The biological component of claim 10 wherein said hydrated substrate is coated onto a surface of a device for implantation into a patient.

18. The biological component of claim 17 wherein said device is selected from the group consisting of, hollow fibers, membrane oxygenators, artificial blood vessels, artificial heart valves, left ventricular assist devices, artificial hearts, artificial lungs, artificial kidneys, artificial livers, vascular grafts, artificial heart valves, artificial joints, catheters, intraocular lenses, electrodes, artificial cartilage, ligaments, tendons, bone grafts, tissue reinforcements, tissue scaffolds, cell-containing capsules, intraluminal stents for use within blood vessels, biliary system, and hollow organs.

19. The biological component of claim 10 wherein said hydrated substance is coated onto the lumenal surface of a porous or nonporous conduit.

20. The biological component of claim 10 wherein said polyelectrolyte is alginate or poly-L-lysine.

21. The biological component of claim 10 wherein alternating layers of oppositely-charged polyelectrolytes are complexed onto said hydrated substrate.

22. The biological component of claim 11 wherein said membrane-mimetic surface comprises a phospholipid.

23. The biological component of claim 11 wherein said phospholipid is selected from the group consisting of phosphatidylcholine, phosphatidylethanolamine, phosphatidylglycerol, ether-based phospholipids, lipopeptide conjugates, and glycolipid conjugates.

24. The biological component of claim 22 wherein said phospholipid contains at least one polymerizable group.

25. The biological component of claim 22 wherein said phospholipid contains only one polymerizable group.

26. The biological component of claim 11 wherein said membrane-mimetic surface comprises a polymerized phosphatidylcholine phospholipid.

27. The biological component of claim 11 wherein said membrane-mimetic surface is formed by in situ polymerization of a phospholipid on said alkylated surface.

28. The biological component of claim 27 wherein said polymerization is performed by fusion of said phospholipid followed by photopolymerization.

29. The biological component of claim 11 wherein said membrane-mimetic surface is formed by photocrosslinking of lipid molecules to functionalities on said alkylated surface.

30. The biological component of claim 11 comprising between said membrane-mimetic surface and said substrate a synthetic self-assembling amphiphile selected from the group consisting of polymers comprising an anchoring component and a hydrophilic spacer component.

31. The biological component of claim 30 wherein said self-assembling amphiphile also comprises a self-assembling hydrophobic component.

32. The biological component of claim 31 wherein said amphiphile comprises a copolymer comprising of 2-hydroxymethyl acrylate (HEA) and 3-acryloyl-3-oxapropyl-3-(N,N-dioctadecylcarbamoyl)-propionate (AOD) in a 1:1 molar ratio.

33. The biological component of claim 32 wherein said copolymer is applied directly to an alginate substrate.

34. The biological component of claim 1 wherein said membrane-mimetic surface comprises a polymerized phosphatidylcholine phospholipid.

35. The biological component of claim 11 wherein an antithrombogenic membrane-mimetic surface is formed by incorporating an antithrombogenic moiety into said surface in an amount sufficient to minimize thrombogenesis.

36. The biological component of claim 11 wherein said antithrombogenic moiety is a moiety of an antithrombotic, antiplatelet, or profibrinolytic agent.

37. The biological component of claim 36 wherein said antithrombogenic moiety is comprised in a molecule selected from the group consisting of thrombomodulin, endothelial cell protein C receptor, vascular ATP diphosphohydrolase, hirudin, and lysine.

38. The biological component of claim 36 wherein said antithrombogenic moiety is added to a phospholipid prior to polymerization in situ.

39. The biological component of claim 36 wherein a lipid-modified thrombomodulin mutant is added to said phospholipid.

40. The biological component of claim 39 wherein said antithrombogenic moiety comprises extracytoplasmic domains of thrombomodulin.

41. The biological component of claim 39 wherein said lipid-modified thrombomodulin mutant is selected from the group consisting of a thrombomodulin fragment generated enzymatically, or by recombinant methods, containing any or all of the extracellular domain which includes EGF repeats 4-6.

42. A biological component comprising a membrane-mimetic surface of claim 11 designed to minimize a host inflammatory response comprising a neoglycocalyx formed on said membrane-mimetic surface using a synthetic or natural glycosaminoglycan.

43. The biological component of claim 42 wherein said synthetic or natural glycosaminoglycan is selected from the group consisting of heparin, heparan sulfate, chondroitin sulfate, dermatan sulfate, keratan sulfate, and hyaluronan and anti inflammatory analogs thereof, linked to said membrane-mimetic surface in an amount effective to minimize a host inflammatory response.

44. The biological component of claim 43 wherein said amount of surface area coverage of between about 10 and about 100%.

45. The biological component comprising a membrane-mimetic surface of claim 11 designed to minimize a host inflammatory response comprising a synthetic hydrophilic polymer selected from the group consisting of polyethylene oxide, polyacrylamide, poly(hydroxymethyl acrylate) (poly(HEA)), poly(hydroxymethyl methacrylate) (poly(HEMA)), and poly(vinylpyrollidone) linked to said membrane-mimetic surface in an amount effective to minimize a host inflammatory response.

46. The biological component of claim 11 wherein said membrane-mimetic surface comprises a targeting moiety linked thereto.

47. The biological component of claim 46 wherein said targeting moiety is selected from the group consisting of Avidin, Streptavidin, thiol-containing proteins, polypeptides, peptides, polysaccharides, lectin, enzymes, and antibodies.

48. A method of forming an alkylated surface on a hydrated substrate comprising:
complexing polyelectrolyte onto the hydrated substrate,
coating the surface of the polyelectrolyte with an oppositely charged amphiphilic polymer containing long-chain alkanes; wherein said amphiphilic polymer comprises a terpolymer, and
coating the amphiphilic polymer with a polymerizable phospholipid.

49. A method of forming a biological component comprising polymerizing a membrane-mimetic lipid onto the amphiphilic polymer of claim 48.

50. The method of claim 49, wherein said biological component has a membrane mimetic surface, said method further comprising forming pores in said membrane-mimetic surface.

51. The method of claim 50 comprising incorporating particles selected from the group consisting of albumin, nanospheres and dendrimers, of a selected size and shape, into said membrane-mimetic surface.

52. A method for delivering a drug comprising incorporating said drug into a biological component of claim 1.

53. The method of claim 52 wherein said drug is incorporated into said substrate.

54. A method of minimizing or abrogating a host inflammatory response to an implanted substrate of claim 1 comprising:

incorporating into the artificial membrane of claim 1 a moiety having anti-inflammatory effect.

55. The method of claim 54 wherein said moiety is that of a molecule selected from the group consisting of thrombomodulin, endothelial cell protein C receptor, vascular ATP diphosphohydrolase, hirudin, annexin, HLA-G, IL-10, hyaluronan, heparan sulfate, heparin, chondroitin sulfate, keratan sulfate, dermatan sulfate and anti-inflammatory analogs of the foregoing.

56. The method of claim 54 wherein said anti-inflammatory moiety is incorporated into said membrane-mimetic surface.

57. The biological component of claim 1, wherein said polymerizable phospholipid comprises mono-acrylated phospholipid.

58. The biological component of claim 1, wherein said terpolymer comprises 2-hydroxymethyl acrylate:N,N-dioctadecylcarbamoyl-propionic acid:styrene sulfonate or HEA:DOD:SS in a molar ratio of 6:3:1.

59. The biological component of claim 1, wherein said polyelectrolyte cushion layer comprises (PLL/alginate)$_5$.

* * * * *